(12) United States Patent
Njar et al.

(10) Patent No.: US 9,884,067 B2
(45) Date of Patent: Feb. 6, 2018

(54) ANDROGEN RECEPTOR DOWN-REGULATING AGENTS AND USES THEREOF

(71) Applicants: UNIVERSITY OF MARYLAND EASTERN SHORE, Princess Anne, MD (US); THOMAS JEFFERSON UNIVERSITY, Philadelphia, PA (US); UNIVERSITY OF MARYLAND, BALTIMORE, Baltimore, MD (US)

(72) Inventors: Vincent C. O. Njar, Glen Burnie, MD (US); Lalji K. Gediya, Gaithersburg, MD (US); Puranik Purushottamachar, Gaithersburg, MD (US); Abhijit Godbole, Macungie, PA (US); Andrew Kwegyir-Afful, Severn, MD (US); Tadas Vasaitis, Salisbury, MD (US)

(73) Assignees: University of Maryland, Baltimore, Baltimore, MD (US); University of Maryland Eastern Shore, Princess Anne, MD (US); Thomas Jefferson University, Philadelphia, PA (US)

( * ) Notice: Subject to any disclaimer, the term of this patent is extended or adjusted under 35 U.S.C. 154(b) by 0 days.

(21) Appl. No.: 14/759,555

(22) PCT Filed: Mar. 14, 2014

(86) PCT No.: PCT/US2014/029667
§ 371 (c)(1),
(2) Date: Jul. 7, 2015

(87) PCT Pub. No.: WO2014/153215
PCT Pub. Date: Sep. 25, 2014

(65) Prior Publication Data
US 2015/0361126 A1    Dec. 17, 2015

Related U.S. Application Data

(60) Provisional application No. 61/782,383, filed on Mar. 14, 2013.

(51) Int. Cl.
*A61K 31/56* (2006.01)
*A61K 31/58* (2006.01)
(Continued)

(52) U.S. Cl.
CPC .............. *A61K 31/58* (2013.01); *A61K 45/06* (2013.01); *A61N 5/10* (2013.01); *C07J 43/003* (2013.01)

(58) Field of Classification Search
CPC ....... A61K 31/58; A61K 45/06; C07J 43/003; A61N 5/10
(Continued)

(56) References Cited

U.S. PATENT DOCUMENTS 2,664,423 A    12/1953    Rorig
3,060,174 A    10/1962    Albert et al.
(Continued)

FOREIGN PATENT DOCUMENTS

CA    2721506 A1    10/2009
CN    101023349 A    8/2007
(Continued)

OTHER PUBLICATIONS

Li et al, Androgen Receptor Splice Variants Mediate Enzalutamide Resistance in Castration-Resistant Prostate Cancer Cell lines, Cancer Research ,73(2), Jan. 15, 2013, p. 483-489.*
(Continued)

*Primary Examiner* — T. Victor Oh
(74) *Attorney, Agent, or Firm* — Westerman, Hattori, Daniels & Adrian, LLP

(57) ABSTRACT

The present disclosure provides the design and synthesis of novel steroidal compounds that cause down-regulation of
(Continued)

the androgen receptor (AR), both full length and splice variant. The compounds are potential agents for the treatment of all forms of prostate cancer and other diseases that depend on functional AR.

13 Claims, 12 Drawing Sheets

(51) Int. Cl.
    *A61K 45/06*     (2006.01)
    *C07J 43/00*     (2006.01)
    *A61N 5/10*     (2006.01)

(58) Field of Classification Search
    USPC .......................................................... 514/171
    See application file for complete search history.

(56) References Cited

U.S. PATENT DOCUMENTS

| | | |
|---|---|---|
| 3,313,809 A | 4/1967 | Clinton et al. |
| 3,317,520 A | 5/1967 | Clinton |
| 3,480,621 A | 11/1969 | Loken et al. |
| 3,539,687 A | 11/1970 | Kuhnen et al. |
| 4,000,125 A | 12/1976 | Casagrande et al. |
| 4,316,885 A | 2/1982 | Rakhit |
| 4,469,689 A | 9/1984 | Anderson et al. |
| 4,650,803 A | 3/1987 | Stella et al. |
| 4,816,567 A | 3/1989 | Cabilly et al. |
| 4,877,611 A | 10/1989 | Cantrell |
| 5,023,263 A | 6/1991 | Von Burg |
| 5,023,264 A | 6/1991 | Caufield et al. |
| 5,028,726 A | 7/1991 | Farrell |
| 5,100,883 A | 3/1992 | Schiehser |
| 5,104,895 A | 4/1992 | Spinelli et al. |
| 5,118,677 A | 6/1992 | Caufield |
| 5,118,678 A | 6/1992 | Kao et al. |
| 5,120,842 A | 6/1992 | Failli et al. |
| 5,151,413 A | 9/1992 | Caufield et al. |
| 5,162,333 A | 11/1992 | Failli et al. |
| 5,177,203 A | 1/1993 | Failli et al. |
| 5,221,670 A | 6/1993 | Caufield |
| 5,223,409 A | 6/1993 | Ladner et al. |
| 5,225,539 A | 7/1993 | Winter |
| 5,232,917 A | 8/1993 | Bolger et al. |
| 5,233,036 A | 8/1993 | Hughes |
| 5,237,064 A | 8/1993 | Bakshi et al. |
| 5,256,790 A | 10/1993 | Nelson |
| 5,258,389 A | 11/1993 | Goulet et al. |
| 5,260,300 A | 11/1993 | Hu |
| 5,262,423 A | 11/1993 | Kao |
| 5,264,427 A | 11/1993 | Brodie et al. |
| 5,264,428 A | 11/1993 | Streber |
| 5,270,163 A | 12/1993 | Gold et al. |
| 5,300,294 A | 4/1994 | Johnson |
| 5,302,584 A | 4/1994 | Kao et al. |
| 5,362,718 A | 11/1994 | Skotnicki et al. |
| 5,373,014 A | 12/1994 | Failli et al. |
| 5,378,836 A | 1/1995 | Kao et al. |
| 5,385,908 A | 1/1995 | Nelson et al. |
| 5,385,909 A | 1/1995 | Nelson et al. |
| 5,385,910 A | 1/1995 | Ocain et al. |
| 5,385,936 A | 1/1995 | Flack et al. |
| 5,389,639 A | 2/1995 | Failli et al. |
| 5,391,730 A | 2/1995 | Skotnicki et al. |
| 5,399,346 A | 3/1995 | Anderson et al. |
| 5,411,967 A | 5/1995 | Kao et al. |
| 5,434,260 A | 7/1995 | Skotnicki et al. |
| 5,456,923 A | 10/1995 | Nakamichi et al. |
| 5,463,048 A | 10/1995 | Skotnicki et al. |
| 5,475,096 A | 12/1995 | Gold et al. |
| 5,480,988 A | 1/1996 | Failli et al. |
| 5,480,989 A | 1/1996 | Kao et al. |
| 5,489,680 A | 2/1996 | Failli et al. |
| 5,491,231 A | 2/1996 | Nelson et al. |
| 5,496,556 A | 3/1996 | Johnson |
| 5,504,091 A | 4/1996 | Molnar-Kimber et al. |
| 5,512,570 A | 4/1996 | Dorn et al. |
| 5,530,101 A | 6/1996 | Queen et al. |
| 5,556,752 A | 9/1996 | Lockhart et al. |
| 5,563,145 A | 10/1996 | Failli et al. |
| 5,565,332 A | 10/1996 | Hoogenboom et al. |
| 5,567,588 A | 10/1996 | Gold et al. |
| 5,578,832 A | 11/1996 | Trulson et al. |
| 5,585,089 A | 12/1996 | Queen et al. |
| 5,593,839 A | 1/1997 | Hubbell et al. |
| 5,595,877 A | 1/1997 | Gold et al. |
| 5,599,695 A | 2/1997 | Pease et al. |
| 5,601,981 A | 2/1997 | Malins |
| 5,604,213 A | 2/1997 | Barrie et al. |
| 5,620,986 A | 4/1997 | Witzel et al. |
| 5,631,734 A | 5/1997 | Stern et al. |
| 5,637,310 A | 6/1997 | Johnson |
| 5,637,459 A | 6/1997 | Burke et al. |
| 5,660,985 A | 8/1997 | Pieken et al. |
| 5,665,772 A | 9/1997 | Cottens et al. |
| 5,670,637 A | 9/1997 | Gold et al. |
| 5,672,605 A | 9/1997 | Or et al. |
| 5,683,867 A | 11/1997 | Biesecker et al. |
| 5,693,762 A | 12/1997 | Queen et al. |
| 5,696,249 A | 12/1997 | Gold et al. |
| 5,707,796 A | 1/1998 | Gold et al. |
| 5,721,227 A | 2/1998 | Melloni et al. |
| 5,721,367 A | 2/1998 | Kay et al. |
| 5,741,795 A | 4/1998 | Aster et al. |
| 5,780,462 A | 7/1998 | Lee et al. |
| 5,837,243 A | 11/1998 | Deo et al. |
| 5,837,832 A | 11/1998 | Chee et al. |
| 5,843,708 A | 12/1998 | Hardman et al. |
| 5,859,205 A | 1/1999 | Adair et al. |
| 5,939,598 A | 8/1999 | Kucherlapati et al. |
| 5,994,334 A | 11/1999 | Brodie et al. |
| 5,994,335 A | 11/1999 | Brodie et al. |
| 6,011,020 A | 1/2000 | Gold et al. |
| 6,113,898 A | 9/2000 | Anderson et al. |
| 6,130,364 A | 10/2000 | Jakobovits et al. |
| 6,133,280 A | 10/2000 | Brodie et al. |
| 6,180,377 B1 | 1/2001 | Morgan et al. |
| 6,200,965 B1 | 3/2001 | Brodie et al. |
| 6,368,598 B1 | 4/2002 | D'Amico et al. |
| 6,423,511 B1 | 7/2002 | Nakamura et al. |
| 6,436,665 B1 | 8/2002 | Kuimelis |
| 6,444,649 B1 | 9/2002 | Inamori et al. |
| 6,444,683 B2 | 9/2002 | Brodie et al. |
| 6,458,592 B1 | 10/2002 | Jakobovits et al. |
| 6,548,555 B1 | 4/2003 | Curatolo et al. |
| 6,763,607 B2 | 7/2004 | Beyerinck et al. |
| 6,933,312 B2 | 8/2005 | Price et al. |
| 6,960,584 B2 | 11/2005 | Carling et al. |
| 6,973,741 B2 | 12/2005 | Beyerinck et al. |
| 6,982,258 B2 | 1/2006 | Posner et al. |
| 7,098,208 B2 | 8/2006 | Owens et al. |
| 7,192,974 B2 | 3/2007 | Gravestock et al. |
| 7,223,738 B2 | 5/2007 | Bilodeau et al. |
| 7,304,063 B2 | 12/2007 | Bilodeau et al. |
| 7,378,403 B2 | 5/2008 | Kozikowski et al. |
| 7,396,832 B2 | 7/2008 | Lindsley et al. |
| 7,399,764 B2 | 7/2008 | Duggan et al. |
| 7,414,055 B2 | 8/2008 | Duggan et al. |
| 7,544,677 B2 | 6/2009 | Bilodeau et al. |
| 7,576,209 B2 | 8/2009 | Kelly et al. |
| 7,579,355 B2 | 8/2009 | Bilodeau et al. |
| 7,589,068 B2 | 9/2009 | Cosford et al. |
| 7,604,947 B2 | 10/2009 | Gudas |
| 7,638,530 B2 | 12/2009 | Bilodeau et al. |
| 7,655,649 B2 | 2/2010 | Bilodeau et al. |
| 7,705,014 B2 | 4/2010 | Chen et al. |
| 7,750,151 B2 | 7/2010 | Bilodeau et al. |
| 7,780,988 B2 | 8/2010 | Beyerinck et al. |
| 7,807,393 B2 | 10/2010 | Thaxton et al. |
| 7,875,599 B2 | 1/2011 | Brodie et al. |
| 7,887,840 B2 | 2/2011 | Curatolo et al. |
| 7,943,732 B2 | 5/2011 | Reed |

(56) References Cited

U.S. PATENT DOCUMENTS

| | | |
|---|---|---|
| 7,960,435 B2 | 6/2011 | Njar et al. |
| 8,003,643 B2 | 8/2011 | Bilodeau et al. |
| 8,003,651 B2 | 8/2011 | Mitchell et al. |
| 8,008,317 B2 | 8/2011 | Armstrong et al. |
| 8,026,286 B2 | 9/2011 | Curatolo et al. |
| 8,034,381 B2 | 10/2011 | Moschwitzer |
| 8,110,550 B2 | 2/2012 | Brodie et al. |
| 8,129,184 B2 | 3/2012 | Yu |
| 8,133,724 B2 | 3/2012 | Qiu et al. |
| 8,168,652 B2 | 5/2012 | Sanderson et al. |
| 8,257,741 B2 | 9/2012 | Curatolo et al. |
| 8,263,357 B2 | 9/2012 | Reed |
| 8,273,782 B2 | 9/2012 | Seefeld et al. |
| 8,324,221 B2 | 12/2012 | Banka et al. |
| 8,785,423 B2 | 7/2014 | Njar et al. |
| 8,791,094 B2 | 7/2014 | Morrison et al. |
| 8,791,095 B2 | 7/2014 | Casebier |
| 8,822,438 B2 | 9/2014 | Auerbach et al. |
| 8,841,422 B2 | 9/2014 | Qiu et al. |
| 8,927,515 B2 | 1/2015 | Brown et al. |
| 9,018,198 B2 | 4/2015 | Njar et al. |
| 9,146,238 B2 | 9/2015 | Luo et al. |
| 9,156,878 B2 | 10/2015 | Morrison et al. |
| 9,295,679 B2 | 3/2016 | Njar et al. |
| 9,387,216 B2 | 7/2016 | Njar et al. |
| 9,439,912 B2 | 9/2016 | Njar et al. |
| 2001/0001099 A1 | 5/2001 | Brodie et al. |
| 2002/0009494 A1 | 1/2002 | Curatolo et al. |
| 2002/0165381 A1 | 11/2002 | Ahrens-Fath et al. |
| 2003/0054053 A1 | 3/2003 | Young et al. |
| 2003/0059471 A1 | 3/2003 | Compton et al. |
| 2004/0058896 A1 | 3/2004 | Dietrich et al. |
| 2006/0013873 A1 | 1/2006 | Yang et al. |
| 2006/0204588 A1 | 9/2006 | Liversidge et al. |
| 2007/0037887 A1 | 2/2007 | Santen et al. |
| 2007/0185152 A1 | 8/2007 | Yamashita et al. |
| 2007/0238647 A1 | 10/2007 | Bowen et al. |
| 2008/0058301 A1 | 3/2008 | Lardy et al. |
| 2008/0280864 A1 | 11/2008 | Brodie et al. |
| 2009/0012045 A1 | 1/2009 | Hitoshi et al. |
| 2009/0047252 A1 | 2/2009 | Cai et al. |
| 2009/0048149 A1 | 2/2009 | Ng et al. |
| 2009/0221672 A1 | 9/2009 | Zhang et al. |
| 2010/0009397 A1 | 1/2010 | Sebti et al. |
| 2010/0029667 A1 | 2/2010 | Ketner et al. |
| 2010/0047338 A1 | 2/2010 | Brodie et al. |
| 2010/0048524 A1 | 2/2010 | Brodie et al. |
| 2010/0048912 A1 | 2/2010 | Brodie et al. |
| 2010/0048913 A1 | 2/2010 | Brodie et al. |
| 2010/0048914 A1 | 2/2010 | Brodie et al. |
| 2010/0068802 A1 | 3/2010 | Qiu et al. |
| 2010/0137269 A1 | 6/2010 | Brodie et al. |
| 2010/0298383 A1 | 11/2010 | Ng et al. |
| 2011/0034428 A1* | 2/2011 | Morrison ............... C07J 43/003 514/176 |
| 2011/0105445 A1* | 5/2011 | Njar ....................... A61K 31/58 514/170 |
| 2011/0110926 A1 | 5/2011 | Luo et al. |
| 2011/0118219 A1 | 5/2011 | Njar et al. |
| 2011/0160170 A1 | 6/2011 | Njar et al. |
| 2011/0178070 A1 | 7/2011 | Gong et al. |
| 2011/0195966 A1 | 8/2011 | Garcia-Echeverria et al. |
| 2011/0224223 A1 | 9/2011 | Shokat et al. |
| 2011/0312916 A1 | 12/2011 | Casebier |
| 2011/0312924 A1 | 12/2011 | Casebier |
| 2011/0313229 A1 | 12/2011 | Sugaya et al. |
| 2011/0319369 A1 | 12/2011 | Casebier et al. |
| 2012/0028972 A1 | 2/2012 | Wong et al. |
| 2012/0282331 A1 | 11/2012 | Chappel et al. |
| 2012/0292797 A1 | 11/2012 | Curatolo et al. |
| 2013/0130241 A1 | 5/2013 | Dehm |
| 2013/0252930 A1 | 9/2013 | Chu et al. |
| 2014/0066423 A1 | 3/2014 | Becker et al. |
| 2014/0288036 A1 | 9/2014 | Brodie et al. |
| 2014/0288037 A1 | 9/2014 | Casebier et al. |
| 2014/0343024 A1 | 11/2014 | Morrison et al. |
| 2014/0371181 A1 | 12/2014 | Casebier |
| 2015/0005265 A1 | 1/2015 | Stewart |
| 2015/0051179 A1 | 2/2015 | Casebier |
| 2015/0166599 A1 | 6/2015 | Morrison et al. |
| 2015/0174143 A1 | 6/2015 | Njar et al. |
| 2015/0203528 A1 | 7/2015 | Morrison et al. |
| 2015/0233927 A1 | 8/2015 | Giannakakou et al. |
| 2015/0297615 A1 | 10/2015 | Njar et al. |
| 2015/0320770 A1 | 11/2015 | Casebier et al. |
| 2015/0344965 A1 | 12/2015 | Luo et al. |
| 2015/0374721 A1 | 12/2015 | Njar et al. |
| 2016/0000808 A1 | 1/2016 | Njar et al. |
| 2016/0002283 A1 | 1/2016 | Casebier et al. |
| 2016/0038511 A1 | 2/2016 | Njar et al. |
| 2017/0008920 A1 | 1/2017 | Chappel et al. |
| 2017/0157148 A1 | 6/2017 | Morrison et al. |

FOREIGN PATENT DOCUMENTS

| | | |
|---|---|---|
| CN | 101155823 A | 4/2008 |
| EP | 0469548 A2 | 2/1992 |
| EP | 0721016 A2 | 7/1996 |
| EP | 0728520 A1 | 8/1996 |
| EP | 0785280 A2 | 7/1997 |
| EP | 0799897 A1 | 10/1997 |
| EP | 1712222 A2 | 10/2006 |
| EP | 0901786 B1 | 6/2007 |
| EP | 1530457 B1 | 9/2009 |
| EP | 2300041 A2 | 3/2011 |
| GB | 972672 A | 10/1964 |
| GB | 2479337 A | 10/2011 |
| JP | 38-022578 | 10/1963 |
| JP | S51-41372 A | 4/1976 |
| JP | 56-003000 | 1/1981 |
| JP | 59-191000 A | 10/1984 |
| JP | H06-192287 A | 7/1994 |
| JP | H07-505377 A | 6/1995 |
| JP | H08-509617 A | 10/1996 |
| JP | 2002-517433 A | 6/2002 |
| JP | 2004-521963 A | 7/2004 |
| JP | 2005-206546 A | 8/2005 |
| JP | 2007-530582 A | 11/2007 |
| JP | 2008-536807 A | 9/2008 |
| JP | 2016-528252 A | 9/2016 |
| WO | WO-86/01533 A1 | 3/1986 |
| WO | WO-92/05179 A1 | 4/1992 |
| WO | WO-93/11130 A1 | 6/1993 |
| WO | WO-93/20097 A1 | 10/1993 |
| WO | WO-94/02136 A1 | 2/1994 |
| WO | WO-94/02485 A1 | 2/1994 |
| WO | WO-94/09010 A1 | 4/1994 |
| WO | WO-94/25626 A1 | 11/1994 |
| WO | WO-95/14023 A1 | 5/1995 |
| WO | WO-95/16691 A1 | 6/1995 |
| WO | WO-95/22058 A1 | 8/1995 |
| WO | WO-96/41807 A1 | 12/1996 |
| WO | WO-97/02357 A1 | 1/1997 |
| WO | WO-97/27317 A1 | 7/1997 |
| WO | WO-97/29212 A1 | 8/1997 |
| WO | WO-98/02441 A2 | 1/1998 |
| WO | WO-99/63974 A2 | 12/1999 |
| WO | WO-01/14387 A1 | 3/2001 |
| WO | WO-01/19828 A2 | 3/2001 |
| WO | WO-02/17904 A1 | 3/2002 |
| WO | WO-03/032950 A1 | 4/2003 |
| WO | WO-2005/009429 A1 | 2/2005 |
| WO | WO-2005/014023 A1 | 2/2005 |
| WO | WO-2005/047289 A1 | 5/2005 |
| WO | WO-2005/097107 A2 | 10/2005 |
| WO | WO-2005/097760 A1 | 10/2005 |
| WO | WO-2006/093993 A1 | 9/2006 |
| WO | WO-2007/061737 A2 | 5/2007 |
| WO | WO-2007/064993 A2 | 6/2007 |
| WO | WO-2007/087395 A2 | 8/2007 |
| WO | WO-2008/027855 A2 | 3/2008 |
| WO | WO-2008/109163 A1 | 9/2008 |
| WO | WO-2008/154382 A1 | 12/2008 |
| WO | WO-2009/114658 A2 | 9/2009 |

(56) References Cited

FOREIGN PATENT DOCUMENTS

| WO | WO-2009/120565 A2 | 10/2009 |
|----|-------------------|---------|
| WO | WO-2009/128936 A2 | 10/2009 |
| WO | WO-2010/028646 A1 | 3/2010 |
| WO | WO-2010/089763 A2 | 8/2010 |
| WO | WO-2010/091299 A2 | 8/2010 |
| WO | WO-2010/091306 A1 | 8/2010 |
| WO | WO-2010/111132 A2 | 9/2010 |
| WO | WO-2011/017534 A2 | 2/2011 |
| WO | WO-2011/116344 A2 | 9/2011 |
| WO | WO-2012/006241 A2 | 1/2012 |
| WO | WO-2012/129408 A2 | 9/2012 |
| WO | WO-2013/012959 A1 | 1/2013 |
| WO | WO-2013/079964 A1 | 6/2013 |
| WO | WO-2013/096907 A1 | 6/2013 |
| WO | WO-2014/018926 A1 | 1/2014 |
| WO | WO-2014/153215 A1 | 9/2014 |
| WO | WO-2015023710 A1 | 2/2015 |
| WO | WO-2016/033114 A1 | 3/2016 |
| WO | WO-2016/172517 A1 | 10/2016 |

OTHER PUBLICATIONS

Purushottamachar, P. et al., Exploitation of Multi-target Prostate Cancer Clinical Candidate VN/124-1 (TOK-001) to Develop a Novel Class of Androgen Receptor Down Regulating Agents for Prostate Cancer Therapy, Poster, 242nd ACS National Meeting, Aug. 28-Sep. 1, 2011, Paper ID: 11268, 1 page. (Aug. 28, 2011).
Anderson, B. D. et al., Strategies in the Design of Solution-Stable, Water-Soluble Prodrugs 1: A Physical-Organic Approach to Pro-Moiety Selection for 21-Esters of Corticosteroids, Journal of Pharmaceutical Sciences, 75(4): 365-374 (1985).
Author Not Known, FDA approves Zytiga for late-stage prostate cancer, FDA News Release, U.S. Food and Drug Administration, 3 pages (Apr. 28, 2011), retrieved from the internet on Feb. 7, 2016 <http://www.fda.gov/NewsEvents/Newsroom/PressAnnouncements/ucm253055.htm>.
Author Not Known, Highlights of Prescribing Information for Lupron Depot, AbbVie Inc., Chicago, IL, Takeda Pharmaceutical Company, Japan, 26 pages, initial U.S. Approval: 1989, most recent update: 2014.
Beaumont, K. et al., Design of Ester Prodrugs to Enhance Oral Absorption of Poorly Permeable Compounds: Challenges to the Discovery Scientist, Current Drug Metabolism, 4:461-485 (2003).
Carden, C.P. et al., Crossover pharmakokinetic (PK) study to assess oral administrative of abiraterone acetate capsule and tablet formulation in fasted and fed states in patients with prostate cancer, Journal of Clinical Oncology, 2008 ASCO Meeting Proceedings (Post-Meeting Edition) 26(15S):5168 (May 20 Supplement) (2008) [Abstract].
Castles, C.G. et al., Expression of a constitutively active estrogen receptor variant in the estrogen receptor-negative BT-20 human breast cancer cell line, Cancer Res., 53(24):5934-9 (1993).
Charvet, A-S. et al., Inhibition of Human Immunodeficiency Virus Type I Replication by Phosphonoformate- and Phosphonoacetate-2',3'-Dideoxy-3'-thiacytidine Conjugates, J. Med. Chem. 37:2216-2223 (1994).
Corbishley, T.P. et al., Androgen Receptor in Human Normal and Malignant Pancreatic Tissue and Cell Lines, Cancer, 57:1992-1995 (1986).
Declaration of Abdellah Sentissi under 37 C.F.R. 1.132 with exhibits, submitted in U.S. Appl. No. 14/233,335, 15 pages (Dec. 2, 2015).
Dehm, S.M. and Tindall, D.J., Alternatively spliced androgen receptor variants, Endocr. Relat. Cancer, 18(5):R183-96 (2011).
Dehm, S.M., et al., Splicing of a Novel Androgen Receptor Exon Generates a Constitutively Active Androgen Receptor that Mediates Prostate Cancer Therapy Resistance, Cancer Res., 68(13):5469-5477 (2008).

Duc, I. et al., In vitro and in vivo models for the evaluation of potent inhibitors of male rat 17alpha-hydroxylase/C17,20-lyase, J. Steroid. Biochem. Mol. Biol., 84(5):537-42 (2003).
Extended European Search Report for EP 15188218.0, 11 pages (dated Apr. 6, 2016).
Ferraldeschi et al, Agents that Target Androgen Synthesis in Castration-Resistant Prostate Cancer., The Cancer J. 19(1) (2013).
Guo, Z. et al., A Novel Androgen Receptor Splice Variant Is Up-regulated during Prostate Cancer Progression and Promotes Androgen Depletion-Resistant Growth, Cancer Res., 69(6):2305-2313 (2009).
Gupta, E. et al., Changing Paradigms in Management of Metastatic Castration Resistant Prostate Cancer (mCRPC), Boston Medical Center Urology, 14(55):1-8 (2014).
Gülsün et al., Nanocrystal Technology for Oral Delivery of Poorly Water-Soluble Drugs, Fabad J. Pharm. Sci., 34:55-65 (2009).
Hu, R. et al., Ligand-Independent Androgen Receptor Variants Derived from Splicing of Cryptic Exons Signify Hormone-Refractory Prostate Cancer, Cancer Res., 69(1):16-22 (2009).
International Search Report for PCT/US2016/028898, 3 pages (dated Jul. 12, 2016).
Jaworski, T., Degradation and beyond: control of androgen receptor activity by the proteasome system, Cell Mol. Biol. Lett., 11(1):109-31 (2006).
Junghanns, J.U. and Müller, R.H., Nanocrystal technology, drug delivery and clinical applications, Int. J. Nanomedicine., 3(3):295-309 (2008).
Kwegyir-Afful, A. K. et al., Clinical canidate galeterone (VN/124-1 or TOK-001) induces the degradation of full-length and splice variant androgen receptors in human prostate cancer cell lines via PI3K-Akt-M dm2 pathway: implications for prostate cancer therapy, Cancer Research, vol. 73, No. 8, suppl. 1, pp. 4PP (2013).
Li, T.H. et al., A promoting role of androgen receptor in androgen-sensitive and -insensitive prostate cancer cells, Nucleic Acids Res., 35(8):2767-76 (2007).
Libertini, S.J. et al., Evidence for Calpain-Mediated Androgen Receptor Cleavage as a Mechanism for Androgen Independence, Cancer Res, 67(19):9001-9005 (2007).
Moreira, V.M. et al., CYP17 inhibitors for prostate cancer treatment—an update, Curr. Med. Chem., 15(9):868-99 (2008) [Abstract Only].
Njar, V.C. and Brodie, A.M., Discovery and development of Galeterone (TOK-001 or VN/124-1) for the treatment of all stages of prostate cancer, J. Med. Chem., 58(5):2077-87 (2015).
Nnane, I.P. et al., Effects of some novel inhibitors of C17,20-lyase and 5alpha-reductase in vitro and in vivo and their potential role in the treatment of prostate cancer, Cancer Res., 58(17):3826-32 (1998).
Okudaira, N. et al., A study of the intestinal absorption of an ester-type prodrug, ME3229, in rats: active efflux transport as a cause of poor bioavailability of the active drug, J. Pharmacol. Exp. Ther., 294(2):580-7 (2000).
Purushottamachar Puranik et al., Systematic Structure Modifications of Multitarget Prostate Cancer Drug Candidate Galeterone to Produce Novel Androgen Receptor Down-Regulating Agents—as an Approach to Treatment of Advanced Prostate Cancer, Journal of Medicinal Chemistry, vol. 56, No. 12, 4880-4898 (2013).
Purushottamachar, P. et al., Systematic Structure Modifcations of Multi-target Prostate Cancer Drug Candidate Galeterone to Produce Novel Androgen Receptor Donw-regulating Agents as an Approach to Treatment of Advanced Prostate Cancer, Journal of Medicinal Chemistry, 79 pages (2013).
Ryan, C.J. et al., Phase I clinical trial of the CYP17 inhibitor abiraterone acetate demonstrating clinical activity in patients with castration-resistant prostate cancer who received prior ketoconazole therapy, J. Clin. Oncol., 28(9):1481-8 (2010).
Stanbrough, M. et al., Increased expression of genes converting adrenal androgens to testosterone in androgen-independent prostate cancer, Cancer Res., 66(5):2815-25 (2006).
Tepper, C.G. et al., Characterization of a Novel Androgen Receptor Mutation in a Relapsed CWR22 Prostate Cancer Xenograft and Cell Line, Cancer Research, 62:6606-6614 (2002).

(56) References Cited

OTHER PUBLICATIONS

Tran, C. et al., Development of a second-generation antiandrogen for treatment of advanced prostate cancer, Science, 324(5928):787-90 (2009).

Vasaitis T. S. et al., Novel, potent anti-androgens of therapeutic potential: recent advances and promising developments, Future Medicinal Chemistry, Future Science Ltd., GB, VI. 2, No. 3, 667-680 (2010).

Vasaitis, T.S. et al., CYP17 inhibitors for prostate cancer therapy, J. Steroid Biochem. Mol. Biol., 125(1-2):23-31 (2011).

Veldscholte, J. et al., The androgen receptor in LNCaP cells contains a mutation in the ligand binding domain which affects steroid binding characteristics and response to antiandrogens, J. Steroid. Biochem. Mol. Biol., 41(3-8):665-9 (1992).

Wicha, J. and Masnyk, M., Cardiotonic Steroids, Part 8., Synthesis of 17beta-(3'-Pyridyl)-14beta-androst-4-ene-3beta, 14-diol from 17-Oxandrostane Derivatives, Bulletin of the Polish Academy of Sciences, Chemistry, 33(1-2):19-27 (1985).

Written Opinion for PCT/US2016/028898, 5 pages (dated Jul. 12, 2016).

Zhao, Z. et al., Modified Taxols, 6.$_1$ Preparation of Water-Soluble Prodrugs of Taxol, Journal of Natural Products, 54(6): 1607-1611 (1991).

Zhou, Z.X. et al., the androgen receptor: an overview, Recent Prog. Horm. Res., 49:249-74 (1994).

Zhuang, Q.Y. et al., [Effects of rapamycin on prostate cancer PC-3 cells], Ai Zheng, 28(8):851-5 (2009) [English Abstract Only].

Abstract of NIH Grant Project Reference No. 2R01 CA27440-25A1, approximate submission date Feb. 18, 2004; approximate award date Sep. 23, 2004.

Abstract of NIH Grant Project Reference No. 3R01 CA27440-2351, approximate date May 3, 2002; approximate award date Jun. 21, 2002.

Abstract of NIH Grant Project Reference No. 5R01 CA27440-23, approximate date Jan. 21, 2002; approximate award date Apr. 29, 2002.

Abstract of NIH Grant Project Reference No. 5R01 CA27440-24, approximate date Feb. 20,2003; approximate award date Jun. 3, 2003.

Abstract of NIH Grant Project Reference No. 5R01 CA27440-2451, approximate date Apr. 1, 2003; approximate award date Jun. 3, 2003.

Abstract of NIH Grant Project Reference No. 5R01 CA27440-26, approximate submission date Jul. 1, 2005; approximate award date Aug. 2, 2005.

Abstract of NIH Grant Project Reference No. 5R01 CA27440-27, approximate submission date Apr. 26, 2006.

Abstract of Nih Grant Project Reference No. 3R01 CA27440-2251, approximate date Jun. 21, 2001; approximate award date Aug. 17, 2001.

Angelastro, M.R. et al., 17 beta-(cyclopropylamino)-androst-5-en-3 beta-ol, a selective mechanism-based inhibitor of cytochrome P450(17 alpha) (steroid 17 alpha-hydroxylase/C17-20 lyase), Biochemical and Biophysical Research Communications, 162(3):1571-1577 (1989).

Armstrong, A.J. et al., A pharmacodynamic study of rapamycin in men with intermediate to high risk localized prostate cancer: A Department of Defense Prosate Cancer Clinical Trials Consortium Trial, Clin. Cancer Res., 16(11):3057-66 (2010).

Auchus, R.J. et al., Use of Prednisone with Abiraterone Acetate in Metastatic Castration-Resistant Prostate Cancer, The Oncologist, 19: 1-10 (2014).

Author Not Known, Definition of Poloxamer, Wikipedia.org, 3 pages, retrieved in May 1, 2014. <http://en.wikipedia.org/wiki/Poloxamer>.

Author Not Known, Phase I Study of Palomid 529 a Dual TORC1/2 Inhibitor of the PI3K/Akt/mTOR Pathway for Advanced Neovascular Age-Related Macular Degeneration (P52901), ClinicalTrials.gov: A Service of the U.S. National Institutes of Health (2012), 3 pages, retrieved on Sep. 16, 2015 <https://clinicaltrials.gov/ct2/show/NCT01033721>.

Ayub, M. et al., Inhibition of testicular 17 alpha-hydroxylase and 17,20-lyase but not 3 beta-hydroxysteroid dehydrogenase-isomerase or 17 beta-hydroxysteroid oxidoreductase by ketoconazole and other imidazole drugs, Journal of Steroid Biochemistry, 28(5):521-531 (1987).

Baldo, P. et al., mTOR pathway and mTOR inhibitors as agents for cancer therapy, Curr. Cancer Drug Targets, 8(8):647-65 (2008). [Abstract Only].

Banks, P.K. et al., Regulation of ovarian steroid biosynthesis by estrogen during proestrus in the rat, Endocrinology, 129(3):1295-1304 (1991).

Barrie, S. E. et al., Pharmacology of novel steroidal inhibitors of cytochrome P450(17) alpha (17 alpha-hydroxylase/C17-20 lyase). J Steroid Biochem Mol Biol. 50:(5-6):267-273 (1994).

Barrie, S.E. et al., Inhibition of 17 alpha-hydroxylase/C17-020 lyase by bifluranol and its analogues, Journal of Steroid Biochemistry, 33(6):1191-1195 (1989).

Berge, et al. Pharmaceutical Salts. Journal of Pharmaceutical Sciences, 66 (1); 1977: 1-17.

Brodie, A.M.H. et al., Inactivation of aromatase in vitro by 4-hydroxy-4-androstene-3,17-dione and 4-acetoxy-4-androstene-3,17-dione and sustained effects in vivo, Steroids, 38(6):693-702 (1981).

Brodie, A.M.H. et al., Studies on the mechanism of estrogen biosynthesis in the rat ovary—I, Journal of Steroid Biochemistry, 7(10):787-793 (1976).

Brodie, A.M.H. Steroidogenesis Pathway Enzymes—Introduction, Design of Enzyme Inhibitors as Drugs vol. 2, M. Sandler and H.J. Smith, Oxford University Press, (Ch. 9):1-13 (1993).

Brodie, A.M.H., et al. Lack of evidence for aromatase in human prostatic tissues: effects of 4-hydroxyandrostenedione and other inhibitors on androgen metabolism, Cancer Research, 49(23):6551-6555 (1989).

Brodie, A.M.H., Inhibitors of Steroid Biosynthesis, Design of Enzyme Inhibitors as Drugs vol. 2, M. Sandler and H.J. Smith, Oxford University Press, (Ch.16):503-522 (1993).

Brodie, A.M.H., Steroidogenesis Pathway Enzymes—Aromatase Inhibitors, Design of Enzyme Inhibitors as Drugs vol. 2, M. Sandler and H.J. Smith, Oxford University Press, (Section 9B):424-438 (1993).

Bruchovsky, N and Wilson, J., The conversion of testosterone to 5-alpha-androstan-17-beta-ol-3-one by rat prostate in vivo and in vitro. J Biol Chem. 243(8):2012-2021 (1968).

Bruno, R. D. et al., 17.alpha.-Hydroxylase/17,20 Lyase Inhibitor VN/124-1 Inhibits Growth of Androgen-independent Prostate Cancer Cells via Induction of theEndoplasmic Reticulum Stress Response, Molecular Cancer Therapeutics, 7 (9), 2828-2836 (2008).

Bruno, R.D. et al., Synthesis and biological evaluations of putative metabolically stable analogs of VN/124-1 (TOK-001): head to head anti-tumor efficacy evaluation of VN/124-1 (TOK-001) and abiraterone in LAPC-4 human prostate cancer xenograft model, Steroids, 76(12):1268-79 (2011).

Bruno, R.D. et al., Targeting cytochrome P450 enzymes: a new approach in anti-cancer drug development, Bioorganic & Medicinal Chemistry, 15(15):5047-5060 (2007).

Bulun, S.E. et al., Use of tissue-specific promoters in the regulation of aromatase cytochrome P450 gene expression in human testicular and ovarian sex cord tumors, as well as in normal fetal and adult gonads, The Journal of Clinical Endocrinology & Metabolism, 77(6):1616-1621 (1993).

Burkhart, J. P. et al., Inhibition of steroid C17(20) lyase with C-17-heteroaryl steroids. Bioorg Med Chem. 4(9):1411-1420 (1996).

Bühler, Pharmaceutical Technology of BASF Excipient, 3rd revised edition, pp. 6-164 (2008).

Chang, S.S., Treatment options for hormone refractory prostate cancer, Rev. Urol., 9 (Suppl 2): S13-S18 (2007).

Chao, J. et al., A versatile synthesis of 17-heterosrylandrostenes via palladium-mediated Suzuki cross-coupling with heteroarylboronic acids, Steroids, 71(7):585-590 (2006).

(56) References Cited

OTHER PUBLICATIONS

Chaumeil, J. C., Micronization: A Method of Improving the Bioavailability of Poorly Soluble Drugs, Meth Find Exp Clin Pharmacol 20(3):211-215 (1998).
Chen, C. D. et al., Molecular determinants of resistance to antiandrogen therapy, Nat Med. 10(1):33-39 (2004).
Chengjie, R. et al., Syntheses and Pharmacological Activity of some 17-[2'substituted)-4'-pyrimidyl] androstene derivativies as inhibitors of human 17alpha-hydroxylase/C17,20-lyse., J. Chin. Pharm. Sci., 10(1): 3-8 (2001).
Chomczynski, P. and Sacchi, N., Single-step method of RNA isolation by acid guanidinium thiocyanate-phenol-chloroform extraction, Analytical Biochemistry, 162(1):156-159 (1987).
Choshi, T. et al., Total synthesis of grossularines-1 and -2. J. Org. Chem. 60:5899-5904 (1995).
Christensen, S.B. et al., Thapsigargin analogues for targeting programmed death of androgen-independent prostate cancer cells, Bioorganic & Medicinal Chemistry, 7(7):1273-1280 (1999).
Church, G.M. and Gilbert, W., Genomic sequencing, Proceedings of the National Academy of Sciences of the USA, 81(7):1991-1995 (1984).
Clement, O., et al., Three dimensional pharmacophore modeling of human CYP17 inhibitors. Potential agents for prostate cancer therapy, Journal of Medicinal Chemistry,46(12):2345-2351 (2003).
Coen, P. et al., An aromatase-producing sex-cord tumor resulting in prepubertal gynecomastia, The New England Journal of Medicine, 324(5):317-322 (1991).
Cohen, S.M. et al., Comparison of the effects of new specific azasteroid inhibitors of steroid 5 alpha-reductase on canine hyperplastic prostate: suppression of prostatic DHT correlated with prostate regression, The Prostate, 26(2):55-71 (1995).
Communication pursuant to Article 94(3) EPC for EP 10150763.0, 12 pages (Mar. 23, 2012).
Communication Pursuant to Article 94(3) EPC for EP 10704283.0, 9 pages (Nov. 6, 2012).
Coombes, R.C. et al., 4-Hydroxyandrostenedione treatment for postmenopausal patients with advanced breast cancer, Steroids, 50(1-3):245-252 (1987).
Covey, D.F. et al., 10 beta-propynyl-substituted steroids. Mechanism-based enzyme-activated irreversible inhibitors of estrogen biosynthesis, The Journal of Biological Chemistry, 256(3):1076-1079 (1980).
Crawford, E. D. et al., A controlled trial of leuprolide with and without flutamide in prostatic carcinoma, New Eng J Med. 321:419-424 (1989).
Crawford, E.D. et al., Treatment of newly diagnosed stage D2 prostate cancer with leuprolide and flutamide or leuprolide alone, phase III: prognostic significance of minimal disease, J. Urol., Abstract from AUA Eighty-Seventh Annual Meeting, May 10-14, 1992, 147:417A (1992).
De Souza, et al. Enhancement of paclitaxel activity against hormone-refractory prostate cancer cells in vitro and in vivo by quinacrine. Br J Cancer. 1997; 75 (11): 1593-600.
Denis, L., Role of maximal androgen blockade in advanced prostate cancer. The Prostate Supplement, 5:17-22 (1994).
Denmeade, et al. A history of prostate cancer treatmnt. Nat Rev Cancer. 2002; 2 (5): 389-96.
Denmeade, S.R. and Isaacs, J.T., A history of prostate cancer treatment. Nat Rev Cancer 2(5):389-396 (2002).
Denmeade, S.R. and Isaacs, J.T., The SERCA pump as a therapeutic target: making a "smart bomb" for prostate cancer, Cancer Biology & Therapy, 4(1):14-22 (2005).
Di Salle, E. et al., Effects of 5 alpha-reductase inhibitors on intraprostatic androgens in the rat, The Journal of Steroid Biochemistry and Molecular Biology, 53(1-6):381-385 (1995).
Dihrendra, K. et al, Solid dispersions: a review, Pak. J. Pharm. Sci., 22(2):234-246 (2009).

Doorenbos, N.J. and Milewich, L., 17-beta-isoxazolyl and 17-beta-pyrazolyl steroids from 3-beta-hydroxy-21-formylpregn-5-en-20-one. Structural assignments, The Journal of Organic Chemistry, 31(10):3193-3199 (1966).
Eisenhauer, et al. New response evaluation criteria in solid tumours: revises RECIST guideline (version 1.1), Eur. J. Cancer, 45 (2): 228-47 (2009).
Elliott, G.B et al. Latent carcinoma of the prostate in a 24-year-old man receiving cyclophosphamide and azathioprine, Can. Med. Assoc. J., 116 (6):651-2 (1977).
Evans, B. E. et al., Methods for drug discovery: development of potent, selective, orally effective cholecystokinin antagonists. J Med Chem, 31(12):2235-2246 (1988).
Extended European Search Report for EP 12859516.2, 8 pages (dated May 26, 2015).
Extended European Search Report for EP 06736460, 15 pages (dated Jul. 29, 2009).
Extended European Search Report for EP 10150763.0, 14 pages (dated Dec. 2, 2010).
Extended European Search Report for EP 10807167.1, 10 pages (dated Nov. 6, 2012).
Extended European Search Report for EP 10830591.3, 8 pages (dated Feb. 20, 2013).
Extended European Search Report for EP 12814940.8, 5 pages (May 18, 2015).
Fedorak, et al. A novel colon-specific steroid prodrug enhances sodium chloride absorption in rat colitis. Am J Physiol. Aug. 1995; 269 (2 Pt 1): G210-8.
Feldman, B.J. et al., The development of androgen-independent prostate cancer, Nature Reviews Cancer, 1(1):34-45 (2001).
Forti, G. et al., Three-month treatment with a long-acting gonadotropin-releasing hormone agonist of patients with benign prostatic hyperplasia: effects on tissue androgen concentration, 5 alpha-reductase activity and androgen receptor content, the Journal of Clinical Endocrinology & Metabolism, 68(2):461-468 (1989).
Frey, B.M. et al., Pharmacokinetics of 3 prednisolone prodrugs. Evidence of therapeutic inequivalence in renal transplant patients with rejection, Transplantation, 39(3):270-274 (1985).
Frye, S.V. et al., 6-Azasteroids: potent dual inhibitors of human type 1 and 2 steroid 5 alpha-reductase, The Journal of Medicinal Chemistry, 36(26):4313-4315 (1993).
Frye, S.V. et al., 6-Azasteroids: structure-activity relationships for inhibition of type 1 and 2 human 5 alpha-reductase and human adrenal 3 beta-hydroxy-delta 5-steroid dehydrogenase/3-keto-delta 5-steroid isomerase, The Journal of Medicinal Chemistry, 37(15):2352-2360 (1994).
Frye, S.V. et al., Structure-activity relationships for inhibition of type 1 and 2 human 5 alpha-reductase and human adrenal 3 beta-hydroxy-delta 5-steroid dehydrogenase/3-keto-delta 5-steroid isomerase by 6-azaandrost-4-en-3-ones: optimization of the C17 substituent, The Journal of Medicinal Chemistry, 38(14):2621-2627 (1995).
Funke, R. et al., A Phase Ib/II Study Testing the Safety and Efficacy of Combined Inhibition of the PI3K/Akt and Androgen Receptor Signaling Pathways in Castration-resistant Prostate Cancer: GDC-0068 or GDC-0980 with Abiraterone Acetate Versus Abiraterone Acetate, Array Biopharma, TPS2616, 1 page (2012), retrieved on Sep. 25, 2012 <http://www.arraybiopharma.com/_documents/Publication/PubAttachment524.pdf>.
Gaddipati, J.P. et al., Frequent detection of codon 877 mutation in the androgen receptor gene in advanced prostate cancers, Cancer Research, 54(11):2861-2864 (1994).
Garde, D., Tokai Pharmaceuticals' Reformulated Galeterone Demonstrates Robust PSA Reductions in Advanced Prostate Cancer Patients, FierceBiotech, 2 pages, Jan. 2, 2014. URL: http://www.fiercebiotech.com/node/349034/print (Retrieved from the Internet Jul. 28, 2015).
Garrett, R. H. et al. [Editors]. Chapter 8: Lipids. Biochemistry (Second Edition). Saunders College Publishing. pp. 238-258 (1999).

(56) References Cited

OTHER PUBLICATIONS

Geller, J. et al., Comparison of prostatic cancer tissue dihydrotestosterone levels at the time of relapse following orchiectomy or estrogen therapy, The Journal of Urology, 132(4):693-696 (1984).
Gold, R. et al., Detection of DNA fragmentation in apoptosis: application of in situ nick translation to cell culture systems and tissue sections, Journal of Histochemistry & Cytochemistry, 41(7):1023-1030 (1993).
Goldman, A.S. et al., Production of male pseudohermaphroditism in rats by two new inhibitors of steroid 17alpha-hydroxylase and C 17-20 lyase, Journal of Endocrinology, 71(3):289-297 (1976).
Gomez-Orellana, I., Strategies to improve oral drug bioavailability, Expert Opinion on Drug Delivery, 2(3):419-433 (2005).
Goodin, et al. Effect of docetaxel in patients with hormone-dependent prostate-specific antigen progression after local therapy for prostate cancer, J. Clin. Oncol., 23 (15): 3352-7 (2005).
Gormley, G.J., Role of 5 alpha-reductase inhibitors in the treatment of advanced prostatic carcinoma, Urologic Clinics of North America, 18(1):93-98 (1991).
Goss, P.E. et al., Treatment of advanced postmenopausal breast cancer with an aromatase inhibitor, 4-hydroxyandrostenedione: phase II report, Cancer Research, 46(9):4823-4826 (1986).
Goya, S. et al., Studies on cardiotonic steroid analogs, V. : synthesis of 17β(or α)-isoxazolyl and pyrazolyl-16-methyl-14β(or α)-androst-5-enes, Yakugaku Zasshi, 90(5):537-543 (1970) [English Abstract Only].
Gravina, G.L. et al., The TORC1/TORC2 inhibitor, Palomid 529, reduces tumor growth and sensitizes to docetaxel and cisplatin in aggressive and hormone-refractory prostate cancer cells, Endocr. Relat. Cancer, 18(4):385-400 (2011).
Griengl, H. et al. Phosphonoformate and phosphonoacetate derivatives of 5-substituted 2'-deoxyuridines: synthesis and antiviral activity, J. Med. Chem., 31(9):1831-9 (1988).
Grigoryev, D. N. et al., Cytochrome P450c17-expressing *Escherichia coli* as a first-step screening system for 17alpha-hydroxylase-C17,20-lyase inhibitors, Analytical Biochem. 267(2):319-30 (1999).
Grigoryev, D. N. et al., Effects of new 17alpha-hydroxylase/C(17,20)-lyase inhibitors on LNCaP prostate cancer cell growth in vitro and in vivo. Br J Cancer. 81(4):622-630 (1999).
Guarna, A. et al., A concise route to 19-nor-10-azasteroids, a new class of steroid 5α-reductase inhibitors. 3.1 synthesis of (+)-19-nor-10-azatestosterone and (+)-17β-(acetyloxy)-(5β)-10-azaestr-1-en-3-one, The Journal of Organic Chemistry, 63(12):4111-4115 (1998).
Haase-Held, M. et al., The synthesis of 4-cyanoprogesterone: a potent inhibitor of the enzyme 5-α-reductase, Journal of the Chemical Society, Perkin Transactions 1, 22:2999-3000 (1992).
Habernicht, U.F. et al., Induction of estrogen-related hyperplastic changes in the prostate of the cynomolgus monkey (*Macaca fascicularis*) by androstenedione and its antagonization by the aromatase inhibitor 1-methyl-androsta-1,4-diene-3,17-dione , The Prostate, 11(4):313-326 (1987).
Haffner, C., Synthesis of 6-azacholesten-3-ones: potent inhibitors of 5?-reductase, Tetrahedron Letters, 36(23):4039-4042 (1995).
Haidar, S. et al. Effects of novel 17alpha-hydroxylase/C17, 20-lyase (P450 17, CYP 17) inhibitors on androgen biosynthesis in vitro and in vivo. J Steroid Biochem Mol Biol. 84(5):555-562 (2003).
Haidar, S. et al., Novel steroidal pyrimidyl inhibitors of P450 17 (17 alpha-hydroxylase/C17-20-lyase). Arch Pharm, Pharm Med. Chem 334(12):373-374 (2001).
Hakki, et al. CYP17- and CYPIIB-dependent steroidhydroxylases as drug development targets. Pharmacology & Therapeutics. Jul. 2006; 111(1):27-52 (2006).
Hall, P. F., Cytochrome P-450 C21scc: one enzyme with two actions: hydroxylase and lyase. J Steroid Biochem Mol Biol. 40(4-6):527-532 (1991).
Hamilton, G.A., Chemical models and mechanisms for oxygenases, Molecular Mechanisms of Oxygen Activation, 1:405-451 (1974).
Hamm, R. et al., Patient self-injection: A new approach to administering luteinizing hormone-releasing hormone analogues, 86(7): 840-842 (2000).
Handratta, V. D. et al, Potent CYP17 inhibitors: improved syntheses, pharmacokinetics and anti-tumor activity in the LNCaP human prostate cancer model. J Steroid Biochem Mol Biol. 92(3):155-165 (2004).
Handratta, V. et al., Novel C-17-heteroaryl steroidal CYP17 inhibitors/antiandrogens: synthesis, in vitro biological activity, pharmacokinetics, and antitumor activity in the LAPC4 human prostate cancer xenograft model, Journal of Medicinal Chemistry, 48(8):2972-2984 (2005).
Harada, N., Novel properties of human placental aromatase as cytochrome P-450: purification and characterization of a unique form of aromatase, The Journal of Biochemistry, 103(1):106-113 (1988).
Harlow, et al. Antibodies, a laboratory manual (1988.).
Hartley, T. et al., Endoplasmic reticulum stress response in an INS-1 pancreatic beta-cell line with inducible expression of a folding-deficient proinsulin, BMC Cell Biology, 11:59 (2010).
Hartmann, R. W. et al. Synthesis and evaluation of novel steroidal oxime inhibitors of P450 17 (17 alpha-hydroxylase/C17-20-lyase) and 5 alpha-reductase types 1 and 2. J Med Chem. 43(22):4266-4277 (2000).
Henderson, D. et al., Estrogens and benign prostatic hyperplasia: the basis for aromatase inhibitor therapy, 50(1-3):219-233 (1987).
Higuchi, et al. Pro-drugs as novel drug delivery systems. American Chemical Socety. ACS symposium series 14 (1975).
Hochhaus, et al. A selective HPLC/RIA for dexamethasone and its prodrug dexamethasone-21-sulphobenzoate sodium in biological fluids, Biomed. Chromatogr., 6(6):283-6 (1992).
Hoehn, W. et al., Human prostatic adenocarcinoma: some characteristics of a serially transplantable line in nude mice (PC 82), The Prostate, 1(1):95-104 (1980).
Holt, D.A. et al., Inhibition of steroid 5 alpha-reductase by unsaturated 3-carboxysteroids, The Journal of Medicinal Chemistry, 33(3):943-950 (1990).
Hsiang, Y.H. et al., The influence of 4-hydroxy-4-androstene-3,17-dione on androgen metabolism and action in cultured human foreskin fibroblasts, Journal of Steroid Biochemistry, 26(1):131-135 (1987).
Hudes, et al. Paciltaxel plus estramustine in metastatic hormone-refractory prostate cancer. Seminars in Oncology, vol. 22, No. 5. Suppl. 12. Oct. 1995, pp. 41-45.
Huggins, C. et al. Studies in prostate cancer: The effects of castration on advanced carcinoma of the prostate gland. Arch Surg. 43(2):209-223 (1941).
Humber, D. C. et al. Synthesis and biological activity of some cardiotonic compounds related to digitoxigenin. Steroids. 42(2):189-202 (1983).
Humez, S. et al., Role of endoplasmic reticulum calcium content in prostate cancer cell growth regulation by IGF and TNFalpha, Journal of Cellular Physiology, 201(2):201-213 (2004).
Hussain, et al. Docetaxel followed by hormone therapy after failure of definitive treatments for clinically localized/locally advanced prostate cancer; preliminary results, Seminars in Oncology, 28(4) Suppl. 15, pp. 22-31 (2001).
Inkster, S. et al., Human testicular aromatase: immunocytochemical and biochemical studies, The Journal of Clinical Endocrinology & Metabolism, 80(6):1941-1947 (1995).
International Search Report and Written Opinion for PCT/US10/044570 (dated Apr. 29, 2011).
International Search Report and Written Opinion for PCT/US2010/023391 (dated Jun. 17, 2010).
International Search Report and Written Opinion for PCT/US2010/040448 (dated Nov. 30, 2009).
International Search Report and Written Opinion for PCT/US2010/055996 (dated Jul. 28, 2011).
International Search Report and Written Opinion for PCT/US2012/071485 (dated Feb. 27, 2013).
International Search Report for PCT/US2006/007143, 1 page (dated Aug. 14, 2006).

(56) References Cited

OTHER PUBLICATIONS

International Search Report for PCT/US2009/036891, 3 pages (dated Oct. 7, 2009).
International Search Report for PCT/US2009/037610, 4 pages (dated Dec. 1, 2009).
International Search Report for PCT/US2010/023381 (dated Jun. 9, 2010).
International Search Report for PCT/US2010/023387 (dated Jul. 5, 2010).
International Search Report for PCT/US2012/047253, 5 pages (dated Dec. 7, 2012).
Ishibashi, K. et al., Synthesis of b-nor-4-aza-5α-androstane compound as 5α-reductase inhibitor, Bioorganic & Medicinal Chemistry Letters, 4(5):729-732 (1994).
Jain, et al. Food and oral antineoplastics: more than meets the eye, Clin. Cancer Res., 16(17): 4305-7 (2010).
Jarman, M. et al., Hydroxyperfluoroazobenzenes: novel inhibitors of enzymes of androgen biosynthesis, The Journal of Medicinal Chemistry, 33(9):2452-2455 (1990).
Jarman, M. et al., Inhibitors of enzymes of androgen biosynthesis: cytochrome P450(17) alpha and 5 alpha-steroid reductase. Nat Prod Rep. 15(5):495-512 (1998).
Jarman, M. et al., The 16,17-double bond is needed for irreversible inhibition of human cytochrome p45017alpha by abiraterone (17-(3-pyridyl)androsta-5, 16-dien-3beta-ol) and related steroidal inhibitors, The Journal of Medicinal Chemistry, 41(27):5375-5381 (1998).
Jefcoate, C. R., Measurement of substrate and inhibitor binding to microsomal cytochrome P-450 by optical-difference spectroscopy. Methods Enzymol. 52:258-279 (1978).
Jemal, A. et al. Cancer statistics, 2004. CA cancer J. Clin. 54(1):8-29 (2004).
Kadar et al., Technical and safety aspects of blood and marrow transplantation using G-CSF mobilized family donors, Transfusion Science 17(4):611-618 (1996).
Kim, O. et al. Synergism of cytoplasmic kinases in IL6-induced ligand-independent activation of androgen receptor in prostate cancer cells. Oncogene. 23(10):1838-1844 (2004).
Kitz, R. and Wilson, I.B., Esters of methanesulfonic acid as irreversible inhibitors of acetylcholinesterase, The Journal of Biological Chemistry 237(10):3245-3249 (1962).
Klein, K. A. et al. Progression of metastatic human prostate cancer to androgen independence in immunodeficient SCID mice. Nat Med. 3(4):402-408 (1997).
Klus, G.T. et al., Growth inhibition of human prostate cells in vitro by novel inhibitors of androgen synthesis, Cancer Research, 56(21):4956-4964 (1996).
Kozák, I. et al., Nuclei of stroma: site of highest estrogen concentration in human benign prostatic hyperplasia, The Prostate, 3(5):433-438 (1982).
Krieg, M. et al., Stroma of human benign prostatic hyperplasia: preferential tissue for androgen metabolism and oestrogen binding, Acta Endocrinologica (Copenhagen), 96(3):422-432 (1981).
Kuppens, I.E.L.M. et al., Oral bioavailability of docetaxel in combination with OC144-093 (ONT-093), Cancer Chemother. Pharmacol., 55: 72-78 (2005).
Kyprianou, N. and Isaacs, J.T., Expression of transforming growth factor-beta in the rat ventral prostate during castration-induced programmed cell death, Molecular Endocrinology, 3(10):1515-1522 (1989).
Kyprianou, N. et al., Programmed cell death during regression of PC-82 human prostate cancer following androgen ablation, Cancer Research, 50(12):3748-3753 (1990).
Labrie, F. et al., Combination therapy for prostate cancer. Endocrine and biologic basis of its choice as new standard first-line therapy, Cancer, 71(3 Suppl):1059-1067 (1993).
Lai, E. et al., Endoplasmic reticulum stress: signaling the unfolded protein response, Physiology (Bethesda, Md.), 22(3):193-201 (2007).

Laneri, et al. Ionized prodrugs of dehydroepiandrosterone for transdermal iontophoretic delivery, Pharm. Res., 16(12): 1818-24 (1999).
Larsen, J.D. and Bundgaard, H., Prodrug forms for the sulfonamide group. I. Evaluation of N-acyl derivatives, N-sulfonylamidines, N-sulfonylsulfilimines and sulfonylureas as possible prodrug derivatives, Int. J. Pharmaceutics, 37:87-95 (1987).
Larsen, J.D. et al., Prodrug forms for the sulfonamide group. II. Water-soluble amino acid derivatives of N-methylsulfonamides as possible prodrugs, Int. J. Pharmaceutics, 47:103-110 (1988).
Li, J. et al., 4-pregnene-3-one-20β-carboxaldehyde: a potent inhibitor of 17α-hydroxylase/c17,20-lyase and of 5α-reductase, The Journal of Steroid Biochemistry and.Molecular Biology, 42(3-4):313-320 (1992).
Li, J. et al., Inhibition of androgen synthesis by 22-hydroximino-23,24-bisnor-4-cholen-3-one, The Prostate, 26(3):140-150 (1995).
Li, J. et al., Synthesis and evaluation of pregnane derivatives as inhibitors of human testicular 17 alpha-hydroxylase/C17,20-lyase, The Journal of Medicinal Chemistry, 39(21):4335-4339 (1996).
Ling, Y.Z. et al., 17-Imidazolyl, pyrazolyl, and isoxazolyl androstene derivatives. Novel steroidal inhibitors of human cytochrome C17,20-lyase (P450(17 alpha), The Journal of Medicinal Chemistry, 40(20):3297-3304 (1997).
Long, B.J. et al., Antiandrogenic effects of novel androgen synthesis inhibitors on hormone-dependent prostate cancer, Cancer Research, 60(23):6630-6640 (2000).
Lu, Q. et al., Expression of aromatase protein and messenger ribonucleic acid in tumor epithelial cells and evidence of functional significance of locally produced estrogen in human breast cancers, Endocrinology, 137(7):3061-3068 (1996).
Maggiolini, et al. The mutant androgen receptor T877A mediates the proliferative but not the cytotoxic dose-dependent effects of genistein and quercetin on human LNCaP prostate cancer cells. Molecular Pharmacology, vol. 62, pp. 1027-1035 (2002).
Matsunaga, N. et al. C(17,20)-lyase inhibitors. Part 2: design, synthesis and structure-activity relationships of (2-naphthylmethyl)-1H-imidazoles as novel C(17,20)-lyase inhibitors. Bioorg Med Chem. 12(16):4313-4336 (2004).
Matsunaga, N. et al. C17,20-lyase inhibitors I. Structure-based de novo design and SAR study of C17,20-lyase inhibitors. Bioorg Med. Chem., 12(9):2251-2273 (2004).
Matsunaga, N. et al. Synthetic studies on (1S)-1-(6,7-dimethoxy-2-naphthyl)-1-(1H-imidazol-4-yl)-2-methylpropan-1-o-I as a selective C17,20-lyase inhibitor. Tetrahedron: Asymmetry. 15:2021-2028 (2004).
Mawhinney, M.G. and Belts, J.A., Androgens and estrogens in prostatic neoplasia, Advances in Sex Hormone Research, 2:141-209 (1976).
McCague, R. et al., Inhibition of enzymes of estrogen and androgen biosynthesis by esters of 4-pyridylacetic acid, The Journal of Medicinal Chemistry, 33(11):3050-3055 (1990).
McConnell, J. D., Physiologic basis of endocrine therapy for prostatic cancer. Urol Clin North Am. 18(1):1-13 (1991).
McDonald, I.A. et al., Inhibition of steroid 5-alpha-reductase by "inverted" competitive inhibitors, Bioorganic and Medicinal Chemistry Letters, 4(6):847-851 (1994).
McLeod, et al., A glucocorticoid prodrug facilitates normal mucosal function in rat colitis without adrenal suppression, Gastroenterology, 106 (2): 405-13 (1994).
Metcalf, B.W. et al., Substrate-induced inactivation of aromatase by allenic and acetylenic steroids, Journal of the American Chemical Society, 103(11):3221-3222 (1981).
Mohler, J. L. et al., The androgen axis in recurrent prostate cancer. Clin Cancer Res. 10(2):440-448 (2004).
Montgomery, R.B. et al., Galeterone in men with CRPC: results in four distinct patient populations from the ARMOR2 study, Abstract #5029, Poster, Presented at the 50th Annual Meeting of the American Society of Clinical Oncology (ASCO), Chicago, Illinois (May 30, 2014-Jun. 3, 2014).
Moreira, V. et al. Synthesis and evaluation of novel 17-indazole androstene derivatives designed as CYP17 inhibitors, Steroids 72(14):939-948 (2007).

(56) References Cited

OTHER PUBLICATIONS

Muscato, J. J. et al., Optimal dosing of ketoconazole (KETO) and hydrocortisone (HC) leads to long responses in hormone refractory prostate cancer, Thirtieth Annual Meeting of the Americal Society of Clinical Oncology, May 14-17, 1994, vol. 13, p. 229, Abstract 701 (1994).
Nakajin, S. and Hall, P.F., Microsomal cytochrome P-450 from neonatal pig testis. Purification and properties of a C21 steroid side-chain cleavage system (17 alpha-hydroxylase-C17,20 lyase), The Journal of Biological Chemistry, 256(8):3871-3876 (1981).
Nakajin, S. et al., Inhibitory effects and spectral changes in pig testicular cytochrome P-450(17 alpha-hydroxylase/lyase) by 20 beta-hydroxy-C21-steroids, Yakugaku Zasshi (Journal of the Pharmaceutical Society of Japan), 108(12):1188-1195 (1988) [English Abstract Only].
Nakajin, S. et al., Microsomal cytochrome P-450 from neonatal pig testis: two enzymatic activities (17 alpha-hydroxylase and c17,20-lyase) associated with one protein, Biochemistry, 20(14):4037-4042 (1981).
Nawrocki, S.T. et al., Bortezomib sensitizes pancreatic cancer cells to endoplasmic reticulum stress-mediated apoptosis, Cancer Research, 65(24):11658-11666 (2005).
Nicolaou, K. C. et al., Natural Product-like Combinatorial Libraries Based on Privileged Structures. 1. General Principles and Solid-Phase Synthesis of Benzopyrans, J. Am. Chem. Soc. 122(41):9939-9953 (2000).
NIH Grant Project Reference No. 2R01 CA27440-24A1, 2R01 CA27440-25A1 Revised Grant Renewal Application, approximate submission date Feb. 18, 2004; approximate award date Sep. 23, 2004, SAI.MD04. 02 12-5610-360221, signed Feb. 18, 2004.
NIH Grant Project Reference No. 3R01 CA27440-22S1 Grant Application for Supplemental Funding, approximate date Jun. 21, 2001; approximate award date Aug. 17, 2001. SAI:MD01:06 20-5504-360221, received Jun. 21, 2001, signed Jun. 14, 2001.
NIH Grant Project Reference No. 3R01 CA27440-23S1 Grant Continuation Application and Progress Report, approximate date May 3, 2002; approximate award date Jun. 21, 2002, MD01-0220-5807-360221, signed May 3, 2002.
NIH Grant Project Reference No. 5R01 CA27440-23 Grant Continuation Application and Progress Report, approximate date Jan. 21, 2002; approximate award date Apr. 29, 2002, SAI.MD02 17-5787-360221, signed Jan. 21, 2002.
NIH Grant Project Reference No. 5R01 CA27440-24 Grant Continuation Application and Progress Report, approximate date Feb. 20, 2003; approximate award date Jun. 3, 2003, CA27440-24, signed Apr. 1, 2003.
NIH Grant Project Reference No. 5R01 CA27440-24 Grant Renewal Application, approximate submission date Jun. 26, 2003—Unfunded, SAI.MD03.06 26-5626-360221, signed Jun. 26, 2003.
NIH Grant Project Reference No. 5R01 CA27440-26 Grant Renewal Continuation Application and Progress Report, approximate submission date Jul. 1, 2005; approximate award date Aug. 2, 2005, CA27440-26, signed Jul. 1, 2005.
NIH Grant Project Reference No. 5R01 CA27440-27, ESNAP Report, approximate submission date May 8, 2006.
NIH Grant Project Reference No. 5R01 CA27440-27 Grant Continuation Application and Progress Report, approximate submission date Apr. 26, 2006, CA27440-27, signed Apr. 26, 2006.
Nishimura, et al. Effects of flutamide as a second-line agent for maximum androgen blockade of hormone refractory prostate cancer. Int J Urol. Mar. 2007; 14 (3): 264-7.
Njar, V. and Brodie, A., Inhibitors of 17alpha-hydroxylase/17,20-lyase (CYP17): potential agents for the treatment of prostate cancer, Curr Pharm Des. 5(3):163-180 (1999).
Njar, V. et al., Novel 17-azolyl steroids, potent inhibitors of human cytochrome 17 alpha-hydroxylase-C17,20-1yase (P450(17) alpha): potential agents for the treatment of prostate cancer, J Med Chem. 41(6):902-912 (1998).
Njar, V. et al., Nucleophilic vinylic "addition-elimination" substitution reaction of 3.beta.-acetoxy-17-chloro-16-formylandrosta-5,16-diene: A novel and general route to 17-substituted steroids. Part 1—synthesis of novel 17-azolyl-.DELTA..sup.16steroids; inhibitors of 17.alpha.-hydroxylase/17,20-lyase (17.alpha.-lyase), Bioorganic & Medicinal Chemistry Letters, 6(22): 2777-2782 (1996).
Njar, V.C. et al., Synthesis of novel 21-trifluoropregnane steroids: inhibitors of 17 alpha-hydroxylase/17,20-lyase (17 alpha-lyase), Steroids, 62(6):468-473 (1997).
Njar, V.C.O. et al., Novel 10β-aziridinyl steroids; inhibitors of aromatase, Journal of the Chemical Society, Perkin Transactions 1, 10:1161-1168 (1993).
Nnane, I. P. et al., Effects of novel 17-azolyl compounds on androgen synthesis in vitro and in vivo. J Steroid Biochem Mol Biol. 71(3-4):145-152 (1999).
Notice of Allowance for U.S. Appl. No. 12/851,070 (dated May 5, 2014).
Notice of Allowance for U.S. Appl. No. 13/145,997 (dated May 2, 2014).
O'Donnell, A. et al. Hormonal impact of the 17alpha-hydroxylase/C(17,20)-lyase inhibitor abiraterone acetate (CB7630) in patients with prostate cancer. Br J Cancer. 90(12):2317-2325 (2004).
Office Action dated Jan. 31, 2011 for U.S. Appl. No. 12/577,094.
Office Action dated Mar. 12, 2010 for U.S. Appl. No. 11/817,550.
Office Action dated Apr. 4, 2012 for U.S. Appl. No. 12/577,090.
Office Action dated May 5, 2010 for U.S. Appl. No. 12/577,091.
Office Action dated May 7, 2010 from U.S. Appl. No. 12/577,092.
Office Action dated May 12, 2014 for U.S. Appl. No. 13/146,004.
Office Action dated May 23, 2011 from U.S. Appl. No. 12/577,094.
Office Action dated May 25, 2010 for U.S. Appl. No. 12/577,096.
Office Action dated Jun. 1, 2010 from U.S. Appl. No. 12/577,090.
Office Action dated Jun. 1, 2011 from U.S. Appl. No. 12/577,090.
Office Action dated Jun. 1, 2011 from U.S. Appl. No. 12/623,257.
Office Action dated Jun. 2, 2010 for U.S. Appl. No. 11/817,550.
Office Action dated Jun. 2, 2010 from U.S. Appl. No. 11/817,550.
Office Action dated Sep. 8, 2011 from U.S. Appl. No. 12/577,096.
Office Action dated Sep. 9, 2011 from U.S. Appl. No. 12/577,090.
Office Action dated Sep. 19, 2013 for U.S. Appl. No. 13/146,004.
Office Action dated Oct. 5, 2011 for U.S. Appl. No. 12/577,094.
Office Action dated Oct. 17, 2012 for U.S. Appl. No. 12/577,090.
Office Action dated Oct. 20, 2010 for U.S. Appl. No. 12/623,257.
Office Action dated Oct. 28, 2010 for U.S. Appl. No. 12/577,091.
Office Action dated Oct. 28, 2010 for U.S. Appl. No. 12/577,092.
Office Action dated Oct. 29, 2010 from U.S. Appl. No. 12/577,090.
Office Action dated Nov. 1, 2010 from U.S. Appl. No. 12/577,096.
Office Action dated Aug. 29, 2013 for U.S. Appl. No. 13/145,997.
Office Action dated Feb. 2, 2015 for U.S. Appl. No. 14/313,894.
Office Action dated Feb. 8, 2013 for U.S. Appl. No. 12/934,135.
Office Action dated May 30, 2013 for GB Application No. 1114154.6.
Office Action dated Sep. 16, 2013 for U.S. Appl. No. 12/934,135.
Office Action dated Sep. 19, 2013 for U.S. Appl. No. 12/851,070.
Office Action for JP 2007-558143, 7 pages (dated Mar. 7, 2012).
Office Action for U.S. Appl. No. 12/851,070, 19 pages (dated Mar. 12, 2013).
Ojida et al., Stereocontrolled synthesis of (1S)-1-(1H-imidazol-4-yl)-1-(6-methoxy-2-naphthyl)-2-methylpropan-1-ol as a potent C.sub.17,20-lyase inhibitor, Tetrahedron: Asymmetry, 15: 1555-1559 (2004).
Onoda, M. et al., Affinity alkylation of the active site of C21 steroid side-chain cleavage cytochrome P-450 from neonatal porcine testis: a unique cysteine residue alkylated by 17-(bromoacetoxy)progesterone, Biochemistry, 26(2):657-662 (1987).
Pappo, R. and Chorvat, R.J., The synthesis of 2-azasteroids, Tetrahedron Letters, 13(31):3237-3240 (1972).
Partial European Search Report for EP 10150763.0, 6 pages (dated Jul. 16, 2010).
Pataki, J. and Jensen, E.V., Synthesis of fluorinated 3beta-hydroxypregn-5-en-20-one derivatives, Steroids, 28(4):437-447 (1976).
Pelc, B. and Hodková, J., Androstane derivatives substituted by pyrazole ring in position 17, Collection of Czechoslovak Chemical Communications, 34(2):442-450 (1969).

(56) References Cited

OTHER PUBLICATIONS

Petrow, V. and Lack, L., Studies on a 5 alpha-reductase inhibitor and their therapeutic implications, Progress in Clinical & Biological Research, 756:283-297 (1981).
Picard, F. et al., Synthesis and evaluation of 2'-substituted 4-(4'-carboxy- or 4'-carboxymethylbenzylidene)-N-acylpiperidines: highly potent and in vivo active steroid 5alpha-reductase type 2 inhibitors. J Med Chem. 45(16):3406-3417 (2002).
Potter, G. A. et al., A convenient, large-scale synthesis of abiraterone acetate [3B-acetoxy-17-(3-pryidyl)androsta-5,16-diene], a potential new drug for the treatment of prostate cancer. Organic Preparations and Procedures Int. 29(1):123-134 (1997).
Potter, G.A. et al., Novel Steroidal Inhibitors of Human Cytochrome P450.sub.17.alpha.(17.alpha.-Hydroxylase-C.sub.17,20-lyase): Potential Agents for the Treatment of Prostatic Cancer, J. Med. Chem., 38(13): 2463-2471 (1995).
Rahmani, M. et al. The kinase inhibitor sorafenib induces cell death through a process involving induction of endoplasmic reticulum stress, Molecular and Cellular Biology, 27(15):5499-5513 (2007).
Randimbivololona, F. and Lesne, M., Metabolism and excretion in bile of SC4453, a new semi-synthetic derivative of digoxin following an i.v. bolus injection in the guinea-pig. J. Pharmacol. 15(1):53-64 (1984).
Rasmusson, G.H. and Toney, J.H., Therapeutic Control of Androgen Action, Annual Reports in Medicinal Chemistry, 29(23):225-232 (1994).
Rasmusson, G.H. et al., Azasteroids as inhibitors of rat prostatic 5 alpha-reductase, The Journal of Medicinal Chemistry, 27(12):1690-1701 (1984).
Rasmusson, G.H. et al., Azasteroids: structure-activity relationships for inhibition of 5 alpha-reductase and of androgen receptor binding, The Journal of Medicinal Chemistry, 29(11):2298-2315 (1986).
Recanatini, M. et al., A new class of nonsteroidal aromatase inhibitors: design and synthesis of chromone and xanthone derivatives and inhibition of the P450 enzymes aromatase and 17 alpha-hydroxylase/C17,20-lyase. Med Chem. 44(5):672-680 (2001).
Reid, et al. CYP17 inhibition as a hormonal strategy for prostate cancer. Nat Clin Pract Urol. Nov. 2008; 5 (11): 610-20.
Remington: The Science and Practice of Pharmacy, Nineteenth Ed., Mack Publishing Co., Easton, Pennsylvania, (1995).
Rittmaster, R.S. et al., Differential effect of 5 alpha-reductase inhibition and castration on androgen-regulated gene expression in rat prostate, Molecular Endocrinology, 5(7):1023-1029 (1991).
Ron, D. and Walter, P., Signal integration in the endoplasmic reticulum unfolded protein response, Nature Reviews Molecular Cell Biology, 8(7):519-529 (2007).
Russell, D.W. and Wilson, J.D., Steroid 5 alpha-reductase: two genes/two enzymes, Annual Review of Biochemistry, 63:25-61 (1994).
Saad, et al. The Canadian Uro-Oncology Group multicentre phase II study of docetaxel administered every 3 weeks with prednisone in men with metastatic hormone-refractory prostate cancer progressing after mitoxantrone/prednisone. BJU Int. Aug. 5, 2008; 102 (5); 551-5, doi: 10.1111/j.1464-410X.2008.07733.x Epub May 28.
Saulnier, et al. An efficient method for the synthesis of guanidino prodrugs. Bioorganic and Medicinal Chemistry Letters. 1994; 4(16):1985-1990.
Schayowitz, A. et al., Prolonging hormone sensitivity in prostate cancer xenografts through dual inhibition of AR and mTOR, Br. J. Cancer, 103(7):1001-7 (2010).
Schayowitz, et al. Synergistic effect of a novel antiandrogen, VN/124-1, and signal transduction inhibitors in prostate cancer progression of hormone independence in vitro. Mol. Cancer Ther., vol. 7 (1), pp. 121-132, Jan. 2008.
Schayowitz. Synergistic effect of anti-androgens and signal transduction inhibitors in prostate cancer progression, University of Maryland Baltimore Thesis, 86 pages (2008).

Schieweck, K. et al., Anti-tumor and endocrine effects of non-steroidal aromatase inhibitors on estrogen-dependent rat mammary tumors, The Journal of Steroid Biochemistry and Molecular Biology, 44(4-6):633-636 (1993).
Schwarzel, W.C. et al., Studies on the mechanism of estrogen biosynthesis. 8. The development of inhibitors of the enzyme system in human placenta, Endocrinology, 92(3):866-880 (1993).
Shao, T.C. et al., Effects of finasteride on the rat ventral prostate, Journal of Andrology, 14(2):79-86 (1993).
Simmons, et al. Combined androgen blockade revisited: emerging options for the treatment of castration-resistant prostate cancer. Urology. Apr. 2009; 73 (4): 697-705.
Sinkula, J.A. and Yalkowsky, S.H., Rationale for design of biologically reversible drug derivatives: prodrugs, J. Pharm. Sci., 64(2):181-210 (1975).
Sjoerdsma, A., Suicide enzyme inhibitors as potential drugs, Clinical Pharmacology & Therapeutics, 30(1):3-22 (1981).
Skryma, R. et al., Store depletion and store-operated Ca2+ current in human prostate cancer LNCaP cells: involvement in apoptosis, The Journal of Physiology, 527(Pt 1):71-83 (2000).
Small, E. J. et al. Ketoconazole retains activity in advanced prostate cancer patients with progression despite flutamide withdrawal. J Urol. 157(4):1204-1207 (1997).
Snider, C.E. and Brueggemeier, R.W., Covalent modification of aromatase by a radiolabeled irreversible inhibitor, Journal of Steroid Biochemistry, 22(3):325-330 (1985).
Souillac et al., Characterization of Delivery Systems, Differential Scanning Calorimetry in Encyclopedia of Controlled Drug Delivery, John Wiley & Sons, 212-227 (1999).
Stangelberger et al., The combination of antagonists of LHRH with antagonists of GHRH improves inhibition of androgen sensitive MDA-PCa-2b and LuCaP-35 prostate cancers, Prostate, 67(12):1339-53 (2007).
STN Registry No. 851983-85-2, CAS Registry, 1 page, entered STN Jun. 9, 2005.
Stoner, E., The clinical development of a 5 alpha-reductase inhibitor, finasteride, The Journal of Steroid Biochemistry and Molecular Biology 37(3):375-378 (1990).
Szendi, Z. et al., Steroids, LIII: new routes of aminosteroids[1], Monatshefte für Chemie Chemical Monthly, 127(11):1189-1196 (1996).
Thompson T. A. and Wilding, G., Androgen antagonist activity by the antioxidant moiety of vitamin E, 2,2,5,7,8-pentamethyl-6-chromanol in human prostate carcinoma cells. Mol Cancer Ther. 2(8):797-803 (2003).
Tindall, D. et al., Symposium on androgen action in prostate cancer. Cancer Res. 64(19):7178-7180 (2004).
Trachtenberg, J. et al. Ketoconazole: a novel and rapid treatment for advanced prostatic cancer. J Urol. 130(1):152-153 (1983).
Trachtenberg, J., Ketoconazole therapy in advanced prostatic cancer, The Journal of Urology, 132(1):61-63 (1984).
Tunn, U.W. et al., Comparison of LH-RH analogue 1-month depot and 3-month depot by their hormone levels and pharmacokinetic profile in patients with advanced prostate cancer, 60(Suppl. 1): 9-17 (1998).
UK Examination report dated Sep. 27, 2013 for GB Application No. 1114153.8.
UK Examination report dated Oct. 8, 2014 for GB Application No. 1114153.8.
UK Examination report dated Nov. 21, 2014 for GB Application No. 1114153.8.
UK Examination report dated Nov. 21, 2014 for GB Application No. 1416433.9.
Van Steenbrugge, G.J. et al., Transplantable human prostatic carcinoma (PC-82) in athymic nude mice. III. Effects of estrogens on the growth of the tumor tissue, The Prostate, 12(2):157-171 (1988).
Vasaitis, T. et al., Androgen receptor inactivation contributes to antitumor efficacy of CYP17 inhibitor VN/124-1 in prostate cancer, Molecular Cancer Therapeutics,7(8): 2348-2357 (2008).
Vasaitis, T. et al., The Effects of Novel Anti-Androgens on Androgen Receptor Action and Expression, Proceedings of the American Association for Cancer Research 47, Abstract 5340 (2006)http://aacrmeetingabstracts.org/cgi/content/abstract/2006/1/252-d.

(56) References Cited

OTHER PUBLICATIONS

Vehring. Pharmaceutical particle engineering via spray drying. Pharm Res. May 2008;25(5):999-1022. Epub Nov. 28, 2007.
Veldscholte, J. et al., Anti-androgens and the mutated androgen receptor of LNCaP cells: differential effects on binding affinity, heat-shock protein interaction, and transcription activation, Biochemistry, 31(8):2393-2399 (1992).
Vescio, R.A. et al., Cancer biology for individualized therapy: correlation of growth fraction index in native-state histoculture with tumor grade and stage, Proceedings of the National Academy of Sciences of the USA, 87(2):691-695 (1990).
Vippagunta, S. R. et al., Crystalline solids. Adv Drug Deliv Rev. 48(1):3-26 (2001).
Visakorpi, T. et al., In vivo amplification of the androgen receptor gene and progression of human prostate cancer, Nature Genetics 9(4):401-406 (1995).
Voets, M. et al., Heteroaryl-substituted naphthalenes and structurally modified derivatives: selective inhibitors of CYP11B2 for the treatment of congestive heart failure and myocardial fibrosis. J Med Chem. 48(21):6632-6642 (2005).
Wainstein M.A. et al., CWR22: androgen-dependent xenograft model derived from a primary human prostatic carcinoma, Cancer Research, 54(23):6049-6052 (1994).
Wilkinson, G.R., Chapter One: Pharmacokinetics, The Dynamics of Drug Absorption, Distribution, and Elimination, Goodman and Gilman's The Pharmaological Basis of Therapeutics, 10th Supp. Edition (2001).
Williams, G. et al., Objective responses to ketoconazole therapy in patients with relapsed progressive prostatic cancer, British Journal of Urology, 58(1):45-51 (1986).
Written Opinion for PCT/US2006/007143, 4 pages (dated Aug. 14, 2006).
Written Opinion for PCT/US2009/037610, 5 pages (dated Dec. 1, 2009).
Written Opinion for PCT/US2012/047253, 9 pages (dated Dec. 7, 2012).
Wu, J. and Kaufman, R.J., From acute ER stress to physiological roles of the Unfolded Protein Response, Cell Death & Differentiation, 13(3):374-384 (2006).
Yen, W.C. et al., Differential effect of taxol in rat primary and metastatic prostate tumors: site-dependent pharmacodynamics, Pharmaceutical Research, 13(9):1305-1312 (1996).
Yue, W. et al., A new nude mouse model for postmenopausal breast cancer using MCF-7 cells transfected with the human aromatase gene, Cancer Research, 54(19):5092-5095 (1994).
Yue, W., et al. Effect of aromatase inhibitors on growth of mammary tumors in a nude mouse model, Cancer Research, 55(14):3073-3077 (1995).
Zenger, M. et al., Structure-Activity Relationship and Drug Design, Remington's Pharmaceutical Sciences (Sixteenth Edition), Mack Publishing, Chapter 27: 420-425 (1980).
Zhang, J. et al. A small composite probasin promoter confers high levels of prostate-specific gene expression through regulation by androgens and glucocorticoids in vitro and in vivo. Endocrinology. 141(12):4698-4710 (2000).
Zheng, J.Y. and Fulu, M., Decrease of genital organ weights and plasma testosterone levels in rats following oral administration of leurpolide microemulsion, International Journal of Pharmaceutics, 307: 209-215 (2006).
Zhou, J.L. and Brodie, A., The effect of aromatase inhibitor 4-hydroxyandrostenedione on steroid receptors in hormone-dependent tissues of the rat, The Journal of Steroid Biochemistry and Molecular Biology, 52(1):71-76 (1995).
Long, B.J. et al., In vitro and in vivo inhibition of LNCaP prostate cancer cell growth by novel inhibitors of androgen synthesis, Proceedings of the American Association for Cancer Research, 90th Annual Meeting, Apr. 10-14, 1999, vol. 40, Abstract #423 (1999).
Petrow, V. and Lack, L., Studies on a 5-alpha-Reductase Inhibitor and Their Therapeutic Implications, The Prostate Cell: Structure and Function, Part B, pp. 283-297 (1981).

Shearer, R. and Davies, J.H., Studies in Prostatic Cancer with 4-Hydroxyandrostenedione, 4-hydroxyandrostenedione—A new approach to hormone-dependent cancer, Royal Society of Medicine Services, Limited, Ed. Coombes, R.C. and Dowsett, M., Royal Society of Medicine Services International Congress and Symposium Series No. 180, pp. 41-44 (1991).
Vakatkar, V.V. et al., Cleavage of steriodal oximes, semicarbazones and thiosemicarbazones with titanous chloride under mild conditions, Abstract, Chemistry and Industry, Society of Chemical Industry, London, No. 17, p. 742 (1977).
Weintraub, P.M. et al., Chemical Abstract No. 116:214776V for EP 0469547, Chemical Abstracts Service, American Chemical Society, Columbus, OH, 116(22):778 (1992).
Dorwald, F.Z., Side Reactions in Organic Synthesis: A Guide to Successful Synthesis Design, Weinheim: WILEY-VCH Verlag GmbH and Co. KGaA, Preface, 4 pages (2005).
NIH Grant Project Reference No. 5R01 CA27440-24S1 Grant Continuation Application and Progress Report, approximate date Apr. 1, 2003; approximate award date Jun. 3, 2003.
Abrahamsson, P.A., Neuroendocrine Cells in Tumor Growth of the Prostate, Endocrine-Related Cancer, 6:503-19 (1999).
Advisory Action dated Apr. 9, 2015 by the US Patent and Trademark Office for U.S. Appl. No. 12/988,299 (5 pages).
Advisory Action dated Apr. 28, 2015 by the US Patent and Trademark Office for U.S. Appl. No. 12/988,299 (3 pages).
Advisory Action dated Dec. 19, 2013 by the US Patent and Trademark Office for U.S. Appl. No. 12/988,299 (3 pages).
Agoulnik, I.U. and Weigel, N.L., Androgen Receptor Action in Hormone-Dependent and Recurrent Prostate Cancer, J Cell BioChem, 99:362-72 (2006).
Anders, S. et al., HTSeq—A Python framework to work with high-throughput sequencing data, Bioinformatics, 31(2):166-169 (2014).
Andersen, R. et al, Regression of castrate-recurrent prostate cancer by a small-molecule inhibitor of the amino-terminus domain of the androgen receptor, Cancer cell, 17:535-46 (2010).
Anderson, W.F., Prospects for Human Gene Therapy, Science, 226(4673):401-9 (1984).
Antonarakis, E.S. et al., AR-V7 and resistance to enzalutamide and abiraterone in prostate cancer, N. Engl. J. Med., 371(11):1028-38 (2014).
Armstrong, A.J, et al, Biomarkers in the management and treatment of men with metastatic castration-resistant prostate cancer, Eur. Urol., 61(3): 549-559 (2012).
Armstrong, A.J. and Carducci, M.A., New Drugs in Prostate Cancer, Curr Opin Urol, 16:138-45 (2006).
Arora, V.K. et al, Glucocorticoid receptor confers resistance to antiandrogens by bypassing androgen receptor blockade, Cell, 155(6):1309-1322 (2013).
Aryee, M.J. et al, DNA methylation alterations exhibit intraindividual stability and interindividual heterogeneity in prostate cancer metastases, Science translational medicine, 5(169): 169ra10 (2013).
Attard, G. et al, Phase I clinical trial of a selective inhibitor of CYP17, abiraterone acetate, confirms that castration-esistant prostate cancer commonly remains hormone driven, Journal of clinical oncology : official journal of the American Society of Clinical Oncology, 26(28):4563-4571 (2008).
Author Not Known, A Study of Galeterone Compared to Enzalutamide in Men Expressing Androgen Receptor Splice Variant-7 mRNA (AR-V7) Metastatic CRPC (ARMOR3-SV), ClinicalTrials.gov, first received Mar. 19, 2015, last updated Mar. 16, 2016, 3 pages, retrieved online on Mar. 23, 2016: <https://clinicaltrials.gov/ct2/show/NCT02438007?term=galeterone&rank=1>.
Author Not Known, Galeterone shows activity in a variant form of castration-resistant prostate cancer, European Cancer Organisation Report, www.ecco-org.eu, 3 pages (2014) retrieved from the internet on Feb. 17, 2016 <https://www.ecco-org.eu/Global/News/ENA2014PR/2014/11/Galeteroneshowsactivity-inavariantformofcastrationresistantprostatecancer>.
Balbas, M.D. et al, Overcoming mutation-based resistance to antiandrogens with rational drug design, eLife, 2:e00499 (2013).

(56) References Cited

OTHER PUBLICATIONS

Balic et al., Androgen Receptor Length Polymorphism Associated with Prostate Cancer Risk in Hispanic Men, J Urol, 168(5): 2245-8 (2002).
Barltrop, J.A. et al., 5-(3-Carboxymethoxyphenyl)-2-(4,5-Dimethylthiszolyl)-3-(4-Sulfophenyl)Tetrazolium, Inner salt (MTS) and Related Analogs of 3-(4,5-Dimethylthiazolyl)-2,5-Diphenyltetrazolium Bromide (MTT) Reducing to Purple Water-Soluble Formazans as Cell-Viability Indicators, Bioorg & Med Chem Lett, 1(11): 611-4 (1991).
Basch, E, et al, Systemic therapy in men with metastatic castration-resistant prostate cancer: American Society of Clinical Oncology and Cancer .Care Ontario clinical practice guideline, J. Clin. Oncol., 32(30): 3436-3448 (2014).
Bendig, M.M., Humanization of Rodent Monoclonal Antibodies by CDR Grafting, Methods: A Companion Methods in Enzymology, 8:83-93 (1995).
Blömer, U. et al., Highly Efficient and Sustained Gene Transfer in Adult Neurons with a Lentivirus Vector, J Virology, 71(9): 6641-9 (1997).
Brigham, K.L. et al., In Vivo Transfection of Murine Lungs with a Functioning Prokaryotic Gene Using a Liposome Vehicle, Am J Med Sci, 298(4): 278-81 (1989).
Brinkmann, A.O. et al., Mechanisms of Androgen Receptor Activation and Function, J Steriod Biochem Mol Biol, 69(1-06): 307-13 (1999).
Brown et al., Deletion of the Steroid-Binding Domain of the Human Androgen Receptor Gene in One Family with Complete Androgen Insensitivity Syndrome: Evidence for Further Genetic Heterogeneity in this Syndrome, Proc Natl Acad Sci USA, 85(21): 8151-5 (1988).
Butler, L.M. et al., Suppression of Androgen Receptor Signaling in Prostate Cancer Cells by an Inhibitory Receptor Variant, Mol Endocrinol, 20(5): 1009-24 (2006).
Cai, C. et al., Intratumoral de novo steroid synthesis activates androgen receptor in castration-resistant prostate cancer and is upregulated by treatment with CYP17A1 inhibitors, Cancer Res., 71(20):6503-13 (2011).
Carell, T. et al., A Novel Procedure for the Synthesis of Libraries containing Small Organic Molecules, Angew Chem Int Ed Engl, 33(20): 2059-61 (1994).
Carell, T. et al., A Solution-Phase Screening Procedure for the Isolation of Active Compounds from a Library of Molecules, Angew Chem Int Ed Engl, 33(20): 2061-4 (1994).
Carver, B. S. et al, Reciprocal feedback regulation of PI3K and androgen receptor signaling in PTENdeficient prostate cancer, Cancer Cell, 19(5):575-86 (2011).
Casset, F. et al., A Peptide Mimetic of an Anti-CD4 Monoclonal Antibody by Rational Design, Biochem Biophys Res Commun, 307(1): 198-205 (2003).
Catalano, M.G. et al., Altered Expression of Androgen-Receptor Isoforms in Human Colon-Cancer Tissues, Intl J Cancer, 86(3): 325-30 (2000).
Cayouette, M. and Gravel, C., Adenovirus-Mediated Gene Transfer of Ciliary Neurotrophic Factor Can Prevent Photoreceptor Degeneration in the Retinal Degeneration (rd) Mouse, Human Gene Therapy, 8:423-30 (1997).
Ceraline, J. et al., Constitutive activation of the androgen receptor by a point of utation in the hinge region: A new mechanism for androgen-independent grown in prostate cancer, International Journal of Cancer, 198(1):152-157 (2014).
Certificate of Patent issued on Jan. 27, 2016 by the European Patent Office for European Patent Application No. 0933012.0, which was filed on Nov. 15, 2010 and granted as 2300041 on Mar. 30, 2011 (1 page).
Chang, K-H. et al, A Gain-of-Function Mutation in DHT Synthesis in Castration-Resistant Prostate Cancer, Cell, 154(4):1074-1084 (2013).
Chee, M. et al, Accessing Genetic Information with High-Density DNA Arrays, Science, 274:610-614 (1996).
Chen, Y. et al., Targeting the Androgen Receptor Pathway in Prostate Cancer, Curr Opin Pharm, 8: 440-8 (2008).
Cheng, H. et al., Novel agents for the treatment of pancreatic adenocarcinoma, J. Pancreas (Online) 12(4):334-8 (2011), retrieved on Nov. 11, 2015: <http://pancreas.imedpub.com/novel-agents-for-the-treatment-of-pancreatic-adenocarcinoma.pdf>.
Chlenski, A. et al, Androgen receptor expression in androgen-independent prostate cancer cell, Prostate, Wiley-Liss, New York, NY, US, 47(1): 66-75 (2001).
Chmelar, R. et al., Androgen Receptor Coregulators and Their Involvement in the Development and Progression of Prostate Cancer, Int J Cancer, 120: 719-33 (2006).
Cho, C.Y. et al., An Unnatural Biopolymer, Science, 261(5126): 13303-5 (1993).
Cordon-Cardo, C., Androgen Receptor Level in the Prostatectomy Specimen Predicts Time to Disease Progression Post Androgen Suppression Therapy, J Clin Oncol, 25(18S): 5065 (2007).
Cornetta, K. et al., Gene Transfer into Primates and Prospects for Gene Therapy in Humans, Prog Nucleic Acid Res Mol Biol, 36: 311-22 (1989).
Cory, A.H. et al., Use of an Aqueous Soluble Tetrazolium/Formazan Assay for Cell Growth Assays in Culture, Cancer Commun, 3(7): 207-12 (1991).
Cree, A.I. et al., Methotrexate Chemosensitivity by ATP Luminescence in Human Leukemia Cell Lines and in Breast Cancer Primary Cultures: Comparison of the TCA-100 Assay with a Clonogenic Assay, Anticancer Drugs, 6(3): 398 404 (1995).
Crouch, S.P.M., et al., The Use of ATP Bioluminescence as a Measure of Cell Proliferation and Cytotoxicity, J Immunol Meth, 160: 81-8 (1993).
Cull, M.G. et al., Screening for Receptor Ligands Using Large Libraries of Peptides Linked to the C Terminus of the lac Repressor, Proc Natl Acad Sci USA, 89: 1865-9 (1992).
Cwirla, S.E., et al., Peptides on Phage: A Vast Library of Peptides for Identifying Ligands, Proc Natl Acad Sci USA, 87: 6378-82 (1990).
Darshan, M. S. et al, Taxane-induced blockade to nuclear accumulation of the androgen receptor predicts clinical responses in metastatic prostate cancer, Cancer Res., 71(81): 6019-6029 (2011).
De Bono, J.S. et al, Abiraterone and increased survival in metastatic prostate cancer, N. Engl. J. Med. 364(21): 1995-2005 (2011).
De Bono, J.S. et al, Prednisone plus cabazitaxel or mitoxantrone for metastatic castration resistant prostate cancer progressing after docetaxel treatment: a randomised open-label trial, Lancet, 376: 1147-1154 (2010).
De Leeuw, R. et al, Novel actions of next-generation taxanes benefit advanced stages of prostate cancer, Clin. Cancer Res., 21(4):795-807 (2015).
Dehm, S.M. and Tindall, D.J., Androgen Receptor Structural and Functional Elements: Role and Regulation in Prostate Cancer, Mol Endocrinol, 21(12): 2855-63 (2007).
Devlin, J.J. et al., Random Peptide Libraries: A Source of Specific Protein Binding Molecules, Science, 249(4967): 404-6 (1990).
Dewitt, S.H. et al., Diversomers: An Approach to Nonpeptide, nonoligometric Chemical Diversity, Proc Natl Acad Sci USA, 90: 6909-13 (1993).
Dhanasekaran, S.M. et al., Delineation of Prognostic Biomarkers in Prostate Cancer, Nature, 412: 822-6 (2001).
Dransfield, D.T. et al., Galeterone-induced Degradation of the Androgen Receptor Involves Inhibition of a Deubiquitnating Enzyme, ASCO-GU, Jan. 2016, Abstract #345, 1 page (2016).
Efstathiou, E. et al, Effects of abiraterone acetate on androgen signaling in castrate-resistant prostate cancer in bone, Journal of clinical oncology : official journal of the American Society of Clinical Oncology, 30(6):637-43 (2012).
Efstathiou, E. et al, MDV3100 effects on androgen receptor (AR) signaling and bone marrow testosterone concentration modulation: A preliminary report, ASCO Meeting Abstracts, 29:4501 (2011).
Erb, E. et al., Recursive Deconvolution of Combinatorial Chemical Libraries, Proc Natl Acad Sci USA, 91: 11422-6 (1994).
European Search Report and Written Opinion completed Jun. 6, 2016 by the European Patent Office for European Patent Application No. 16152616.5 (9 pages).

(56) References Cited

OTHER PUBLICATIONS

Extended European Search Report for EP 16152616.5-1405, 9 pages (dated Jun. 16, 2016).
Felgner, P.L. et al., Lipofection: A Highly Efficient, Lipid-Mediated DNA-Transfection Procedure, Proc Natl Acad Sci USA, 84: 7413-7 (1987).
Felici, F. et al., Selection of Antibody Ligands from a Large Library of Oligopeptides Expressed on a Multivalent Exposition Vector, J Mol Biol, 222: 301-10 (1991).
Final Office Action dated Nov. 21, 2014 by the US Patent and Trademark Office for U.S. Appl. No. 12/988,299 (21 pages).
Final Office Action dated Sep. 12, 2013 by the US Patent and Trademark Office for U.S. Appl. No. 12/988,299 (5 pages).
Fleming, M.T. et al., Post-Therapy Changes in PSA as an Outcome Measure in Prostate Cancer Clinical Trials, Nat Clin Pract Oncol, 3(12): 658-67 (2006).
Fodor, S.P.A. et al., Multiplexed Biochemical Assays with Bilogical Chips, Nature, 364: 555-6 (1993).
Friedmann, T., Progress Toward Human Gene Therapy, Science, 244(4910) 1275-81 (1989).
Gallop, M.A. et al., Applications of Combinatorial Technologies to Drug Discovery. 1. Background and Peptide Combinatorial Libraries, J Med Chem, 37(9): 1233-51 (1994).
Gan, L. et al, Inhibition of the androgen receptor as a novel mechanism of taxol chemotherapy in prostate cancer, Cancer Res., 69(21): 8386-8394 (2009).
Ge, H. UPA, a Universal Protein Array System for Quantitative Detection of Protein-Protein, Protein-DNA, Protein-RNA and Prtein-Ligand Interactions, Neucleic Acids Reseach, 28(2): e3i-vii (2000).
Gelmann, E.P., Molecular Biology of the Androgen Receptor, J Clin Oncol, 20(13): 3001-15 (2002).
Gribble, G. W., The Synthetic Versatility of Acyloxyborohydrides, Org. Process Res. Dev., 10(5): 1062-1075 (with Additions & Corrections page) (2006).
Gu, Y. et al., Hematopoietic Cell Regulation by Rac1 and Rac2 Guanosine Triphosphatases, Science, 302: 445-9 (2003).
Haapala, K. et al., Androgen receptor alterations in prostate cancer relapsed during a combined androgen blockade by orchiectomy and bicalutamide, Laboratory Investigation, Nature Publishing Group, The United States and Canadian Academy of Pathology, Inc., 81(12): 1647-1651 (2001).
Hacia, J. et al, Detection of heterozygous mutations in BRCA1 using high density oligonucleotide arrays and two-colour fluorescence analysis, Nature Genetics, 14:441-447 (1996.).
Hara, T. et al., Novel mutations of androgen receptor: a possible mechanism of bi calutami de withdrawal syndrome, Cancer Research, 63(1): 149-153 (2003).
Heinlein, C.A. and Chawnshang Chang, Androgen Receptor in Prostate Cancer, Endocr Rev, 25(2): 276-308 (2004).
Heller, R.A. et al., Discovery and Analysis of Inflammatory Disease-Related Genes Using cDNA Microarrays, Proc Natl Acad Sci USA, 94:2150-5 (1997).
Henderson, D., Estrogens and Benign Prostatic Hyperplasia: Rationale for Therapy with Aromatase Inhibitors, Annals med., 23(3):201-203 (1991).
Hirata, S. et al., Isoform/Variant mRNAs for Sex Steroid Hormone Receptors in Humans, Trends Endocrin Met, 14(3): 124-9 (2003).
Hornberg, E. et al, Expression of Androgen Receptor Splice Variants in Prostate Cancer Bone Metastases is Associated with Castration-Resistance and Short Survival, PLoS ONE, 6(4):e19059 (2011).
Houghten, R.A. et al., The Use of Synthetic Peptide Combinatorial Libraries for the Identification of Bioactive Peptides, Biotechniques, 13(3): 412-21 (1992).
Hu, R. et al, A snapshot of the expression signature of androgen receptor splicing variants and their distinctive transcriptional activities, The Prostate 71(15):1656-1667 (2011).

Hu, R. et al, Distinct transcriptional programs mediated by the ligand-dependent full-length androgen receptor and its splice variants in castration-resistant prostate cancer, Cancer Res., 72(14):3457-3462 (2012).
Hussain, M. et al., Prostate-specific antigen progression predicts overall survival in patients with metastatic prostate cancer: data from Southwest Oncology Group Trials 9346 (Intergroup Study 0162) and 9916, J. Clin. Oncol., 27(15):2450-6 (2009).
International Preliminary Report on Patentability for PCT/US2015/046806, 9 pages, dated Feb. 28, 2017.
International Preliminary Report on Patentability dated Oct. 19, 2010 by the International Searching Authority for International Patent Application No. PCT/US2009/002392 (8 pages).
International Search Report and Written Opinion dated Dec. 4, 2009 by the International Searching Authority for International Patent Application No. PCT/US2009/002392 (11 pages).
International Search Report for PCT/US2010/023381, 7 pages (dated Jun. 9, 2010).
International Search Report for PCT/US2014/029667, 3 pages (dated Aug. 1, 2014).
International Search Report for PCT/US2014/050793, 4 pages (dated Jan. 12, 2015).
International Search Report for PCT/US2015/046806, 5 pages, dated Jan. 4, 2016.
International Search Report for PCT/US2015/053653, 3 pages (dated Dec. 28, 2015).
Issue Notification dated Sep. 29, 2015 by the US Patent and Trademark Office for U.S. Appl. No. 12/988,299 (1 pages).
Itakura, K. et al, Synthesis and Use of Synthetic Oligonucleotides, Ann. Rev. Biochem., 53:323-356 (1984).
Jacoby, D.B. et al., Galeterone Shows Anti-Tumor Activity in Multiple Pre-Clinical Models that Express Androgen Receptor Splice Varients, Supporting Correlative Patient Data Seen in ARMOR2, AACR-NCI-EORTC International Conference on Molecular and Cancer Therapeutics, Abstract, 1 page (2015).
Jagla, M. et al., A Splicing Variant of the Androgen Receptor Detected in a Metastatic Prostate Cancer Exhibits Exclusively Cytoplasmic Actions, Endocrin, 148(9): 4334-4343 (2007).
Jenster, G. et al., Domains of the Human Androgen Receptor Involved in Steroid Binding Transcriptional Activation and Subcellular Localization, Mol Endocrin, 5(10): 1396-1404 (1991).
Jenster, G. et al., Functional domains of the human androgen receptor, Journal of Steroid Biochemistry and Molecular Bioology, Elsevier Science Ltd., Oxford, GB, 41(3-8):671-675 (1992).
Johnson, L.G., Gene Therapy for Cystic Fibrosis, Chest, 107: 77S-83S (1995).
Joseph, J.D. et al, a clinically relevant androgen receptor mutation confers resistance to second-generation antiandrogens enzalutamide and ARN-509, Cancer Discovery, 1021-1029 (2013).
Kaarbo, Mari et al., Androgen Signaling and Its Interactions with Other Signaling Pathways in Prostate Cancer, BioEssays, 29: 1227-38 (2007).
Kangas, L. et al., Bioluminescence of Cellular ATP: A New Method for Evaluating Cytotoxic Agents in Vitro, Med Biol, 62(6): 338-43 (1984).
Kantoff, P. W. et al, Sipuleucel-T immunotherapy for castration-resistant prostate cancer, N. Engl. J. Med., 363(5): 411-422 (2010).
Karantanos, T, et al, Understanding the mechanisms of androgen deprivation resistance in prostate cancer at the molecular level, Eur. Urol., 67(3): 470-479 (2014).
Kido, M. et al., Use of a Retroviral Vector with an Internal Opsin Promoter to Direct Gene Expression to Retinal Photorecptor Cells, Curr Eye Res, 15(8): 833-44 (1996).
Kirby, B.J. et al, Functional characterization of circulating tumor cells with a prostate-cancerspecific microfluidic device, PLoS One 7(4): e35976 (2012).
Kittler, R. et al., An Endoribonuclease-Prepared siRNA Screen in Human Cells Identifies Genes Essential for Cell Division, Nature, 432: 1036-40 (2004).
Ko et al., Androgen Receptor Down-Regulation in Prostate Cancer with Phosphorodiamidate Morpholino Antisense Oligomers, J Urol, 172(3): 1140-4 (2004).

(56) References Cited

OTHER PUBLICATIONS

Kozal, M. J. et al, Extensive polymorphisms observed in HIV-1 Glade B protease gene using highdensity oligonucleotide arrays, Nature Medicine, 2(7):753-759 (1996).
Krause, J.E. and Karavolas, H.J., The effect of progesterone analogues, naturally occurring steroids, and contraceptive progestins on hypothalamic and anterior pituitary delta4-steroid (progesterone) 5alpha-reductase, Steroids, 31(6):823-839 (1978).
Lam, K.S., Application of Combinatorial Library Methods in Cancer Research and Drug Discovery,Anticancer Drug Des, 12(3): 145-67 (1997).
Lam, K.S., et al., A New Type of Synthetic Peptide Library for Identifying Ligand-Binding Activity, Nature, 354:82-4 (1991).
Lapouge, G. et al., Specific properties of a C-terminal truncated androgen receptor detected in hormone refractory prostate cancer, Advances in Experimental Medicine and Biology, Springer, US, 617:529-534 (2008).
Le Gal La Salle, G. et al., An Adenovirus Vector for Gene Transfer into Neurons and Glia in the Brain, Science, 259(5097: 988-90 (1993).
Linja, M.J. and Visakorpi, T., Alterations of Androgen Receptor in Prostate Cancer, J Steriod Biochem, 92: 255-64 (2004).
Litvinov, I.V. et al., PC3, but not DU145, human prostate cancer cells retain the coregulators required for tumor suppressor ability of androgen receptor, Prostate, 66(12):1329-38 (2006).
Liu, W. et al, Copy number analysis indicates monoclonal origin of lethal metastatic prostate cancer, Nature medicine 15(5):559-565 (2009).
Lockhart et al., Expression monitoring by hybridization to high-density oligonucleotide arrays. Nature Biotechnology 14:1675 (1996).
Longo DL. New therapies for castration-resistant prostate cancer. The New England journal of medicine, 363:479-81 (2010).
Luo, J. et al, Human prostate cancer and benign prostatic hyperplasia: molecular dissection by gene expression profiling, Cancer Res., 61:4683-4688 (2001).
MacBeath, G. and Schreiber, S.L., Printing Proteins as Microarrays for High-Throughput Function Determination, Science, 289: 1760-3 (2000).
MacCallum, R.M. et al., Antibody-Antigen Interactions: Contact Analysis and Binding Site Topography, J Mol Biol, 262(5): 732-45 (1996).
Maroni, M.D., P.D. and Crawford, E.D., The Benefits of Early Androgen Blockade, Best Pract Res Cl En, 22(2): 317-29 (2008).
Miller, A.D. and Rosman, G.J., Improved Retroviral Vectors for Gene Transfer and Expression, Biotechniques, 7(9): 980-990 (1989).
Miller, A.D., Retrovirus Packaging Cells, Human Gene Therapy, 1:5-14 (1990).
Mitsiades, N. et al, Distinct patterns of dysregulated expression of enzymes involved in androgen synthesis and metabolism in metastatic prostate cancer tumors, Cancer Res., 72(23):6142-6152 (2012).
Miyamoto, A. et al., Increased Proliferation of B Cells and Auto-Immunity in Mice Lacking Protein Kinase Cd, Nature, 416: 865-9 (2002).
Miyoshi, H. et al., Stable and Efficient Gene Transfer into the Retina Using an HIV-Based Lentiviral Vector, Proc Natl Acad Sci USA, 94: 10319-23 (1997).
Moen, R.C., Directions in Gene Therapy, Blood Cells, 17(2): 407-16 (1991).
Montgomery, R.B. et al., Maintenance of Intratumoral Androgens in Metastatic Prostate Cancer: A Mechanism for Castration-Resistant Tumor Growth, Cancer Res, 68(11): 4447-54 (2008).
Mostaghel EA, Marck BT, Plymate SR, et al. Resistance to CYP17A1 inhibition with abiraterone in castration-resistant prostate cancer: induction of steroidogenesis and androgen receptor splice variants, Clinical cancer research: an official journal of the American Association for Cancer Research, 17:5913-25 (2011).
Mostaghel, E.A. and Nelson, P.S., Intracrine Androgen Metabolism in Prostate Cancer Progression: Mechanisms of Castration Resistance and Therapeutic Implications, Best Pract Res Cl En, 22(2): 243-58 (2008).
Nadiminty, et al., NF-kB2/p52 Induces Resistance to Enzalutamide in Prostate Cancer: Role of Androgen Receptor and its Variants, Molecular Cancer Therapy, 12(8): 1629-1637 (2013).
Naldini, L. et al., In Vivo Gene Delivery and Stable Transduction of Nondividing Cells by a Lentiviral Vector, Science, 272(5259): 263-7 (1996).
Narang, S.A. et al, Chemical Synthesis of Deoxyoligonucleotides by the Modified Triester Method, Methods Enzymol., 65(1):610-620 (1980).
Nnane, I.P. et al., Inhibition of Androgen Synthesis in Human Testicular and Prostatic Microsomes and in Male Rats by Novel Steroidal Compounds, The Endocrine Society, 140(6): 2891-2897 (1999).
Non-Final Office Action dated Jun. 5, 2014 by the US Patent and Trademark Office for U.S. Appl. No. 12/988,299 (9 pages).
Non-Final Office Action dated Jun. 20, 2012 by the US Patent and Trademark Office for U.S. Appl. No. 12/988,299 (5 pages).
Norris, J.D. et al, The homeodomain protein HOXB13 regulates the cellular response to androgens, Molecular Cell 36:405-416 (2009).
Notice of Allowance dated Jun. 26, 2015 by the US Patent and Trademark Office for U.S. Appl. No. 12/988,299 (7 pages).
Office Action for U.S. Appl. No. 11/817,550, 9 pages (dated Jun. 2, 2010).
Office Action for U.S. Appl. No. 12/934,135, 11 pages (dated Sep. 16, 2013).
Ono, T. et al., Plasmid DNAs Directly Injected into Mouse Brain with Lipofectin can be Incorporated and Expressed by Brain Cells, Neurosci Lett, 117:259-63 (1990).
Otto, D. and Unsicker, K., Basic FGF Reverses Chemical and Morphological Deficits in the Nigrostriatal System of MPTP-Treated Mice, J Neurosci, 10(6): 1912-21 (1990).
Otto, D. et al., Basic Fibroblast Growth Factor and Nerve Growth Factor Administered in Gel Foam Rescue Medial Septal Neurons after Fimbria Fornix Transection, J Neurosci Res, 22(1): 83-91 (1989).
Pan, Q. et al., Quantitative Microarray Profiling Provides Evidence Against Widespread Coupling of Alternative Splicing with Nonsense-Mediated mRNA Decay to Control Gene Expression, Genes & Dev, 20:153-8 (2006).
Parker, C. et al, Alpha emitter radium-223 and survival in metastatic prostate cancer, N. Engl. J. Med., 369(3): 213-223, 2013.
Paul, W.E., Fundamental Immunology, 3rd Edition, New York: Raven Press, pp. 292-5 (1993).
Paull, K.D. et al., The Synthesis of XTT: A New Tetrazolium Reagent that is Bioreducible to a Water-Soluble Formazan, J Heterocyclic Chem, 25: 911-4 (1988).
Petty, R.D., Comparison of MTT and ATP-Based Assays for the Measurement of Viable Cell Number, J Biolumin Chemilumin, 10:29-34 (1995).
Plymate, S. R. et al,Taxane resistance in prostate cancer mediated by ARdependent GATA2 regustion ofIGF2, Cancer Cell, 27:158-159 (2015).
Preliminary Amendment filed on Feb. 22, 2017 by the United States Patent and Trademark Office for U.S. Appl. No. 15/505,882, filed Feb. 22, 2017(11 pages).
Preliminary Amendment filed on May 21, 2015 with the United States Patent and Trademark Office for U.S. Appl. No. 14/718,955 (3 pages).
Preliminary Amendment filed on Oct. 15, 2010 with the US Patent and Trademark Office for U.S. Appl. No. 12/988,299, (11 pages).
Purushottamachar, P. et al., Systematic structure modifications of multitarget prostate cancer drug candidate galeterone to produce novel androgen receptor down-regulating agents as an approach to treatment of advanced prostate cancer, J. Med. Chem., 56(12):4880-98 (2013).
Quigley, C.A. et al., Complete Androgen Insensitiveity due to Deletion of Exon C of the Androgen Receptor Gene Highlights the Functional Importance of the Second Zinc Finger of the Androgen Receptor in Vivo, Mol Endocrinol, 6(7): 1103-12 (1992).

(56) References Cited

OTHER PUBLICATIONS

Rathkopf, D. et al., Phase I dose-escalation study of the novel antiandrogen BMS-641988 in patients with castration-resistant prostate cancer, Clin. Cancer Res., 17(4):880-7 (2011).
Ravindranathan, P. et al, Peptidomimetic targeting of critical androgen receptor-coregulatory interactions in prostate cancer, Nature Communications, 4(1923): 1-11 (2013).
Response After Final Office Action filed on Mar. 3, 2015 with the US Patent and Trademark Office for U.S. Appl. No. 12/988,299 (8 pages).
Response to Advisory Action filed on Apr. 19, 2015 with the US Patent and Trademark Office for U.S. Appl. No. 12/988,299 (6 pages).
Response to Advisory Action filed on May 14, 2015 with the US Patent and Trademark Office for U.S. Appl. No. 12/988,299 (6 pages).
Response to Final Office Action filed on Dec. 12, 2013 with the US Patent and Trademark Office for U.S. Appl. No. 12/988,299 (9 pages).
Response to Non-Final Office Action filed on Aug. 7, 2014 with the US Patent and Trademark Office for U.S. Appl. No. 12/988,299 (10 pages).
Response to Non-Final Office Action filed on Sep. 20, 2012 with the US Patent and Trademark Office for U.S. Appl. No. 12/988,299, (12 pages).
Response to Restriction Requirement filed on Mar. 29, 2012 with the US Patent and Trademark Office for U.S. Appl. No. 12/988,299 (4 pages).
Response to Restriction Requirement filed on Mar. 30, 2017 with the United States Patent and Trademark Office for U.S. Appl. No. 14/718,955 (13 pages).
Restriction Requirement dated Dec. 30, 2016 by the United States Patent and Trademark Office for U.S. Appl. No. 14/718,955 (11 pages).
Restriction Requirement dated Feb. 29, 2012 by the US Patent and Trademark Office for U.S. Appl. No. 12/988,299, filed May 12, 2011 (8 pages).
Roberts, R.W. and Szostak, J.W., RNA-peptide fusions for the in vitro selection of peptides and proteins, Proc.Natl. Acad. Sci. USA, 94:12997-12302 (1997).
Robinson, J.T. et al, Integrative genomics viewer, Nature biotechnology, 29(1): 24-26 (2011).
Rosenberg, S.A. et al., Gene Transfer into Humans—Immunotherapy of Patients with Advanced Melanoma, Using Tumor-Infiltrating Lymphocytes Modified by Retroviral Gene Transduction, New Engl J Med, 323(9): 570-8 (1990).
Ruefli-Brasse, A.A. et al., Regulation of NF-κB-Dependent Lymphocyte Activation and Development by Paracaspase, Science, 302: 1581-4 (2003).
Ryan, C. J. and Tindall, D. J., Androgen Receptor Rediscovered: The New Biology and Targeting the Androgen Receptor Therapeutically, Journal of Clinical Oncology : Official Journal of the American Society of Clinical Oncology, 29(27): 3651-3658 (2011).
Ryan, C. J. et al, Abiraterone in Metastatic Prostate Cancer without Previous Chemotherapy, New England Journal of Medicine, 368(2):138-148 (2013).
Sadar D., Small Molecule Inhibitors Targeting the "Achilles' Heel" of Androgen Receptor Activity, Cancer Res., 71(4): 1208-1213 (2011).
Sahu, B. et al, FoxA1 Specifies Unique Androgen and Glucocorticoid Receptor Binding Events in Prostate Cancer Cells, Cancer Res., 73(5): 1570-1580 (2013).
Saramäki, O.R. et al., Genetic Aberrations in Prostate Cancer by Microarray Analysis, Int J Cancer, 119: 1322-9 (2006).
Schena, M. et al., Parallel Human Genome Analysis: Microarray-Based Expression Monitoring of 1000 Genes, Proc Natl Acad Sci USA, 93: 10614-9 (1996).
Scher, H.I. and Sawyers, C.L., Biology of Progressive, Castration-Resistant Prostate Cancer: Directed Therapies Targeting the Androgen-Receptor Signaling Axis, J Clin Oncol, 23(32): 8253-61 (2005).
Scher, H.I. et al, Design and end points of clinical trials for patients with progressive prostate cancer and castrate levels of testosterone: recommendations of the Prostate Cancer Clinical Trials Working Group, J. Clin. Oncol., 26(7): 1148-1159, (2008).
Scher, H.I. et al, Increased survival with enzalutamide in prostate cancer after chemotherapy, N. Engl. J. Med., 367(13): 1187-1197 (2012).
Scher, H.I., et al, Antitumour activity of MDV3100 in castration-resistant prostate cancer: a phase 1-2 study, Lancet, 375(9724):1437-1446 (2010).
Scott, J.K. and Smith, G.P., Searching for Peptide Ligands with an Epitope Library, Science, 249(4967): 386-90 (1990).
Seruga, B. et al, Drug resistance in metastatic castration-resistant prostate cancer, Nat. Rev. Clin. Oncol., 8: 12-23 (2011).
Shang, Y. et al., Formation of the Androgen Receptor Transcription Complex, Mol Cell, 9: 601-10 (2002).
Sharp, D., Conference: Gene Therapy, The Lancet, 337: 1277-8 (1991).
Skolnick, J. and Fetrow, J.S., From Genes to Protein Structure and Function: Novel Applications of Computational Approaches in the Genomic Era, Trends Biotechnol, 18(1): 34-9 (2000).
Small, E.J. and Ryan, C.J., The Case for Secondary Hormonal Therapies in the Chemotherapy Age, J Urol, 176: S66-71 (2006).
Steplewski, Z. et al, Effects of Restraint Stress on Inoculated Tumor Growth and Immune Response in Rats, Cancer Research, 45: 5128-5133 (1985).
STN Search for U.S. Appl. No. 14/807,013, 111 pages, received Oct. 27, 2015.
Straubinger, R.M. and Papahadjopoulos, D., Liposomes as Carriers for Intracellular Delivery of Nucleic Acids, Method Enzymol, 101: 512-27 (1983).
Subramanan, A. et al, Gene set enrichment analysis: A knowledge-based approach for interpreting genome-wide expression profiles, Proceedings of the National Academy of Sciences of the United States of America, 102(43): 15545-15550 (2005).
Supplementary European Search Report and Written Opinion dated Jul. 26, 2011 by the European Patent Office for European Patent Application No. 09733012.0 (10 pages).
Suzuki, H. et al., Interfocal Heterogeneity of PTEN/MMAC1 Gene Alterations in Multiple MetastaticProstate Cancer Tissues, Cancer Res, 58: 204-9 (1998).
Tannock, I.F. et al, Docetaxel plus prednisone or mitoxantrone plus prednisone for advanced prostate cancer, N. Engl. J. Med. 351(15): 1502-1512 (2004).
Thadani-Mulero, M. et al, Androgen receptor splice variants determine taxane sensitivity in prostate cancer, Cancer Res., 74(8): 2270-2282 (2014).
Thadani-Mulero, M. et al., Androgen receptor on the move: boarding the microtubule expressway to the nucleus, Cancer Res., 72(18): 4611-4615 (2012).
Therasse, P. et al, New Guidelines to Evaluate the Response to Treatment in Solid Tumors, Journal of the National Cancer Institute, 92(3): 205-216 (2000).
Tilley, W.D. et al., Mutations in the Androgen Receptor Gene are Associated with Progression of Human Prostate Cancer to Androgen Independence, Clinical Cancer Research, 2:277-285 (1996).
Tolstoshev, P. and Anderson, W.F., Gene Expression Using Retroviral Vectors, Curr Opin Biotech, 1:55-61 (1990).
Tyagi, S. and Kramer, F.R., Molecular Beacons: Probes that Fluoresce Upon Hybridization, Nat Biotechnol, 14: 303-8 (1996).
Vajdos, F.F. et al., Comprehensive Functional Maps of the Antigen-Binding Site of an Anti-ErbB2 Antibody Obtained with Shotgun Scanning Mutagenesis, J Mol Biol, 320(2): 415-28 (2002).
Van Soest, R,J. et al, Targeting the androgen receptor confers in vivo cross-resistance between enzalutamide and docetaxel, but not cabazitaxel, in castration-resistant prostate cancer, Eur. Urol., 67: 981-985 (2015).
Vasaitis, T., et al, Androgen receptor inactivation contributes to antitumor efficacy of 17{alpha}-hydroxylase/17,20-lyase inhibitor 3beta-hydroxy-17-(1H-benzimidazole-1-yl)androsta-5,16-diene in prostate cancer, Mol. Cancer Ther., 7(8): 2348-2357 (2008).
Verhoeyen et al., Engineering of Antibodies, BioEssays, 8(2):74-78 (1988).

(56) References Cited

OTHER PUBLICATIONS

Wahl, R.L. et al., Improved Radioimaging and Tumor Localization with Monoclonal F(ab')2, J Nucl Med, 24: 316-25 (1983).

Watson, P.A. et al, Constitutively active androgen receptor splice variants expressed in castration-resistant prostate cancer require full-length androgen receptor, Proceedings of the National Academy of Sciences, 107 (39):16759-16765 (2010).

Wolff, J.A. et al., Direct Gene Transfer into Mouse Muscle in Vivo, Science, 247(4949 pt. 1): 1465-8 (1990).

Written Opinion for PCT/US2014/029667, 5 pages (dated Aug. 1, 2014).

Written Opinion for PCT/US2014/050793, 7 pages (dated Jan. 12, 2015).

Written Opinion for PCT/US2015/046806, 8 pages, dated Jan. 4, 2016.

Written Opinion for PCT/US2015/053653, 9 pages (dated Dec. 28, 2015).

Wu, C.H. et al., Targeting Genes: Delivery and Persistent Expression of a Foreign Gene Driven by Mammalian Regulatory Elements in Vivo, J Biol Chem, 264(29): 16985-7 (1989).

Wu, G.Y. and Wu, C.H., Receptor-Mediated Gene Delivery and Expression in Vivo, J Biol Chem, 263(29): 14621-4 (1988).

Wu, H. et al., Humanization of a murine monoclonal antibody by simultaneous optimization of framework and CDR residues, J Mol Biol, 294(1): 151-62 (1999).

Yamashita, S. et al., ACJ-J9 Suppresses Castration-Resistant Prostate Cancer Growth through Degradation of Full-length and Splice Variant Androgen Receptors, Neoplasia, 14(1): 74-83 (2012).

Yu, Y. et al, Expression and Function of the Progesterone Receptor in Human Prostate Stroma Provide Novel Insights to Cell Proliferation Control, The Journal of clinical endocrinology and metabolism, 98(7):2887-2896 (2013).

Yu, Z. et al, Rapid Induction of Androgen Receptor Splice Variants by Androgen Deprivation in Prostate Cancer, Clinical Cancer Resesarch, 20(6): 1590-1600 (2014).

Zhang, X., et al, Androgen Receptor Variants Occur Frequently in Castration Resistant Prostate Cancer Metastases, PLoS ONE 6(11): e27970, 1-11 (2011).

Zhou, Z. et al., A Ligand-Dependent Bipartite Nuclear Targeting Signal in the Human Androgen Receptor, J Biol Chem, 269(18): 13115-23 (1994).

Zhu, H. et al., Analysis of Yeast Protein Kinases Using Protein Chips, Nat Genet, 26: 283-9 (2000).

Zhu, M-L. et al, Tubulin-targeting chemotherapy 1mpairs androgen receptor activity in prostate cancer, Cancer Res., 70(20): 7992-8002 (2010).

Zhu, X. et al., Identification of an Exon 3 Deletion Splice Variant Androgen Receptor mRNA in Human Breast Cancer, Intl J Cancer, 72(4): 574-80 (1997).

Zuckermann, R.N. et al., Discovery of Nanomolar Ligands for 7-Transmembrane G-Protein-Coupled Receptors from a Diverse N-(Substituted)glycine Peptoid Library, J Med Chem, 37: 2678-85 (1994).

* cited by examiner

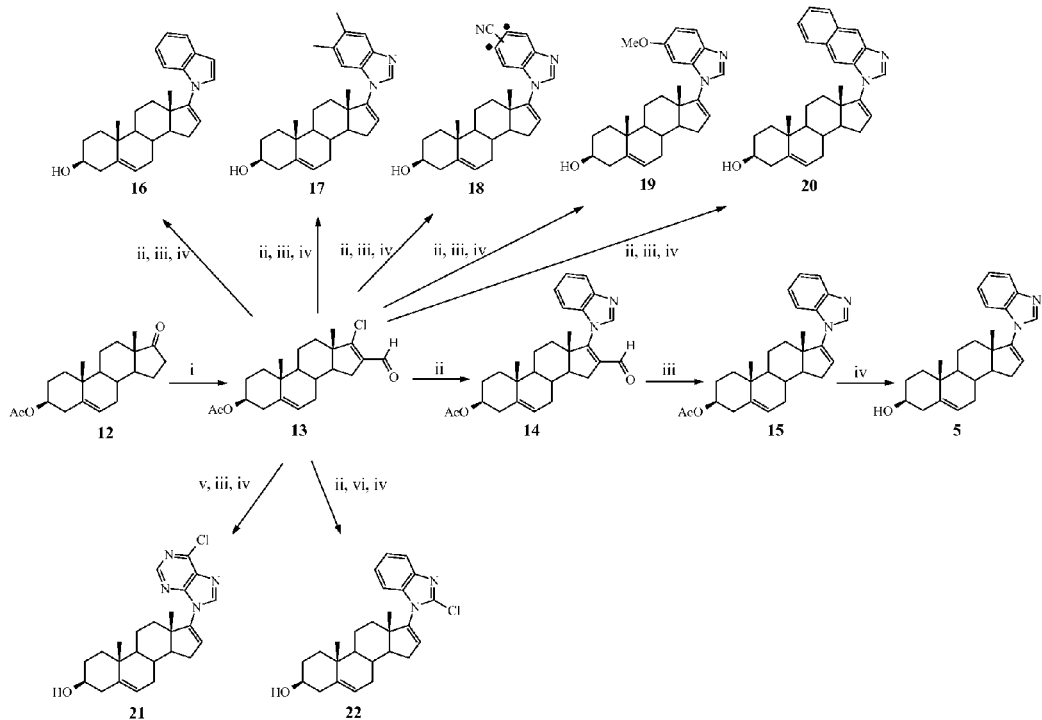

<sup>a</sup>Reagents and conditions: (i) POCl$_3$-DMF, CHCl$_3$, Ar, reflux; (ii) benzimidazole or indole-3-carbaldehyde or 5,6-dimethylbenzimidazole or 5(6)-cyanobenzimidazole or 5(6)-methoxybenzimidazole or naphtho{2,3-d}imidazole, or 2-chlorobenzimidazole, K$_2$CO$_3$, DMF, Ar, 80° C (iii) 10% Pd on activated charcoal, PhCN, reflux; (iv) 10% methanolic KOH, Ar, rt (2 - 3 h). (v) 6-chloropurine, TBAF, THF, Ar, 50° C; (vi) chlorotri(triphenylphosphine)rhodium[I], PhCH$_3$, Ar, reflux.

FIGURE 9

<sup>a</sup>Reagents and conditions: (i) substituted amines, molecular sieves, EtOH, Ar, reflux (3 - 7 h); (ii) MeOH, NaBH₄, ice cold (2 h), rt (3 h); (iii) MeOH, 10% methanolic-KOH, Ar, rt (2 - 3 h);

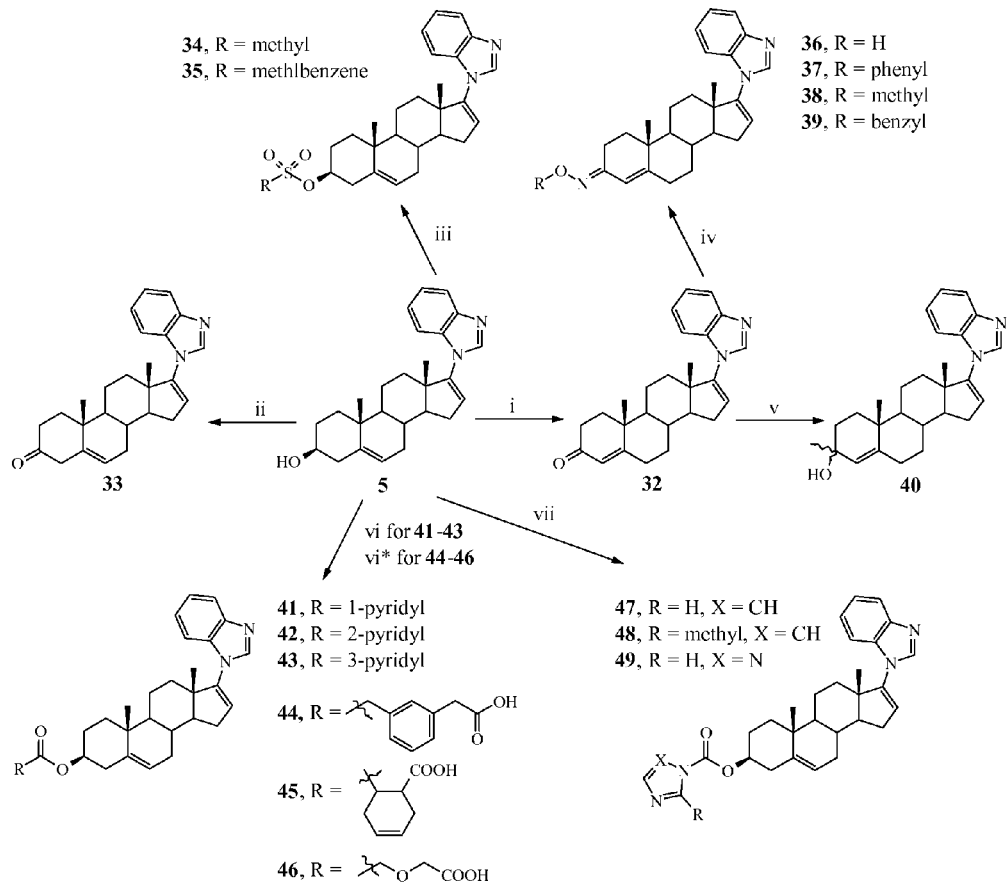

aReagents and conditions: (i) Al(i-PrO)₃, 1-methyl-4-piperidone, toluene, reflux; (ii) Dess-Martin periodinane, MDC, 0° C, rt (5 h); (iii) Mesyl chloride or Tosyl chloride, Pyridine, ice cold (5 h), rt (5 h ); (iv) substituted hydroxylamine HCl, sodium acetate, MeOH, EtOH, Ar, reflux (2 - 3 h); (v) MeLi, THF, Ar, -60° C (1 h) rt (2 h); (vi) pyridine-carboxylic acid, 2-methyl-6-nitobenzoic anhydride, DMAP, TEA, THF, rt (1 h); (vi*) acid anhydride, DMAP, pyridine, reflux; (vii) 1,1'-carbonylbisimidazole or 1,1'-carbonylbis(2-methylimidazole) or 1,1'-carbonyl-di-(1,2,4-triazole), CH₃CN, Ar, rt/reflux.

FIGURE 11

ANDROGEN RECEPTOR DOWN-REGULATING AGENTS AND USES THEREOF

CROSS-REFERENCE

This application claims the benefit of U.S. Provisional Application No. 61/782,383, filed Mar. 14, 2013, which application is incorporated herein by reference.

STATEMENT AS TO FEDERALLY SPONSORED RESEARCH

This invention was made with government support under Grant Numbers CA117991 and CA129379 awarded by the National Institutes of Health. The government has certain rights in the invention.

BACKGROUND OF THE INVENTION

The present disclosure provides the design and synthesis of novel steroidal compounds that cause down-regulation of the androgen receptor (AR), both full length and splice variant. The compounds are potential agents for the treatment of all forms of prostate cancer and other diseases that depend on functional AR.

Compelling laboratory and clinical evidences strongly indicates that incurable castration-resistant prostate cancer (CRPC) remains dependent on functional androgen receptor (AR), AR-mediated processes, and the availability of intraprostatic intracellular androgens. Unlike early stage prostate cancer (ESPC), CRCP is not responsive to classical AR antagonist, [hydroxyflutamide (1) or bicalutamide (2); FIG. 1] or androgen deprivation therapy (luteinizing hormone-releasing hormone agonists/antagonists). Therefore, recent strategies have focused on the development of more potent androgen synthesis inhibitors or AR antagonists. These research efforts have led to ongoing clinical evaluations/approvals of three potent CYP17 inhibitors, abiraterone acetate (Zytiga, 3a), TAK-700 (Orteronel, 4) and VN/124-1 (TOK-001 or galeterone, 5), and two potent AR antagonists, MDV3100 (enzalutamide, 6) and ARN-509 (7). The chemical structures of these clinical compounds are presented in FIG. 1.

Despite the substantial clinical efficacy with Zytiga in patients with post-docetaxel CRPC, resistance to this therapy has already been reported. Resistance to MDV3100 treatment has also been reported. Reactivation of AR signaling following Zytiga or MDV3100 treatment might occur by several mechanisms, prominent of which is a switching of transcription program under the control of AR signaling. Indeed, it may not be possible to inhibit the new AR-regulated transcription program by currently available therapies and some of the promising agents in clinical development. If so, substantial down-regulation of AR (full length and truncated forms) expression would be a promising strategy for future studies.

Herein, we report several novel compounds which exhibit the abilities to induce AR (full length and truncated) ablation at low micromolar concentrations and with improved antiproliferative (AP) activities. This study expands the current understanding of the optimal pharmacophore requirements for AR degradation/down-regulator (ARD) activity and their capabilities in regulating the activity of the AR (i.e., AR inactivation).

SUMMARY OF THE INVENTION

In one aspect, the present disclosure provides a compound of Formula I:

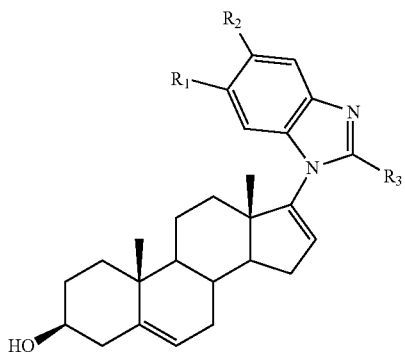

or pharmaceutically acceptable salt thereof, wherein: each of $R_1$ and $R_2$ is independently hydrogen, alkoxy, or CN; $R_3$ is hydrogen or halo; and wherein at least one of $R_1$, $R_2$, $R_3$ is not hydrogen.

In some cases, $R_1$ or $R_2$ can be CN. In other cases, $R_1$ can be alkoxy. For example, $R_1$ can be methoxy. In further cases, $R_3$ can be halo. For example, $R_3$ can be chloro.

In another aspect, the present disclosure provides a compound of Formula II:

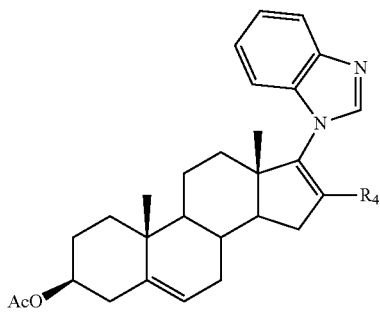

or pharmaceutically acceptable salt thereof, wherein: $R_4$ is —CNHR$_{10}$ or —C=NR$_{10}$; $R_{10}$ is alkyl or aryl, optionally substituted by one or more $R_{11}$ substituents; and $R_{11}$ is halogen, alkoxy, or CN.

In some cases, $R_4$ can be —CNHR$_{10}$. In other cases, $R_4$ can be —C=NR$_{10}$. In some examples, $R_{10}$ can alkyl. In other examples, $R_{10}$ can be aryl. In further examples, $R_{10}$ can be aryl substituted with one or more alkoxy groups.

In yet another aspect, the present disclosure provides a compound of Formula II:

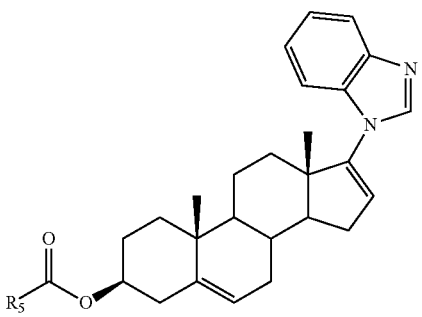

or pharmaceutically acceptable salt thereof, wherein: $R_5$ is heteroaryl, arylalkyl, cycloalkenyl, alkoxyalkyl, optionally substituted with one or more $R_{12}$ substituents; $R_{12}$ is —(CH$_2$)$_n$—CO$_2$H, wherein n is 0, 1, 2, or 3; and with the proviso that $R_5$ is not imidazole.

In some cases, $R_5$ can be heteroaryl. In some examples, $R_5$ can be pyridyl. For example, $R_5$ can be 3-pyridyl. In other examples, $R_5$ can be triazole. In other cases, $R_5$ can be arylalkyl. In yet other cases, $R_5$ can be cycloalkenyl. In further cases, $R_5$ can be alkoxyalkyl. In some examples, $R_{12}$ can be —$CO_2H$ or —$CH_2CO_2H$.

In a further aspect, the present disclosure provides a pharmaceutical composition comprising one or more compounds or pharmaceutically acceptable salts of the present disclosure and a pharmaceutically acceptable excipient, carrier or diluent.

In one aspect, the present disclosure provides a method of treating cancer, a disease or a condition in a subject in need thereof, comprising: administering to the subject an effective amount of a compound, pharmaceutically acceptable salt or composition of the present disclosure.

In some cases, the method can further comprise administering to the subject an effective amount of an antiandrogen, a CYP 17 inhibitor, a luteinizing hormone-releasing hormone agonist, a drug for preventing androgen production, an estrogen, or a chemotherapy drug. In some cases, the compound, pharmaceutically acceptable salt or composition is administered in combination with a hormone therapy, a chemotherapy, a radiation therapy, an immunotherapy, or surgery. In further cases, the cancer, the disease or the condition can be selected from prostate cancer, breast cancer, ovarian cancer, urogenital cancer, or prostate hyperplasia.

In another aspect, the present disclosure provides a method for inhibiting androgen receptor activity in a subject in need thereof, comprising administering to the subject an effective amount of a compound, pharmaceutically acceptable salt or composition of the present disclosure In yet another aspect, the present disclosure provides a method for inhibiting androgen receptor activity in a cell, comprising contacting the cell with an effective amount of a compound, pharmaceutically acceptable salt or composition of the disclosure, and thereby inhibiting androgen receptor activity in the cell.

In one aspect, the present invention provides a method for synthesizing a compound or pharmaceutically acceptable salt of Formula I, comprising the steps of:

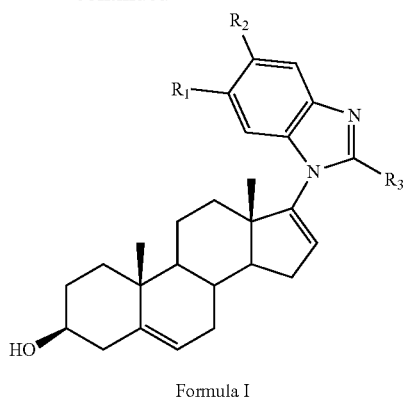

Formula I a. allowing a compound of Formula A to react with a benzimidazole of Formula D under conditions that are effective for synthesizing a compound of Formula Ia; and b. deformylating and hydrolyzing the compound of Formula Ia;

wherein X can be halo; each of $R_1$ and $R_2$ can be independently hydrogen, alkoxy, or CN; $R_3$ can be hydrogen or halo; and wherein at least one of $R_1$, $R_2$, $R_3$ can be not hydrogen.

In some cases, the compound of Formula Ia is deformylated with a Pd catalyst. In another aspect, the present disclosure provides a method for synthesizing a compound or pharmaceutically acceptable salt of Formula II, comprising the steps of:

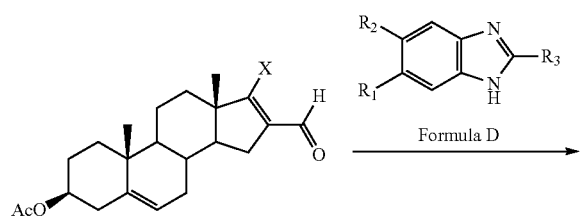

Formula A

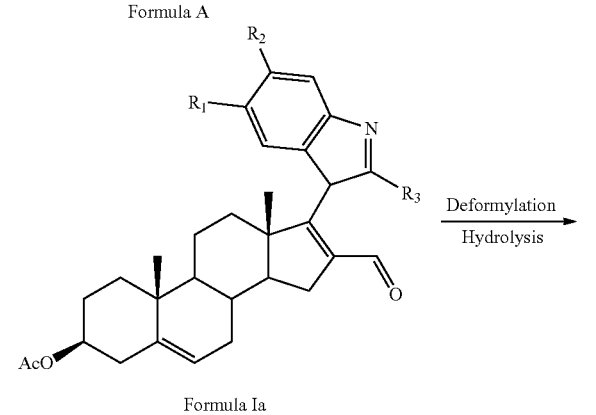

Formula Ia

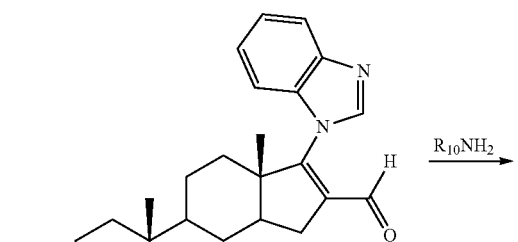

Formula B

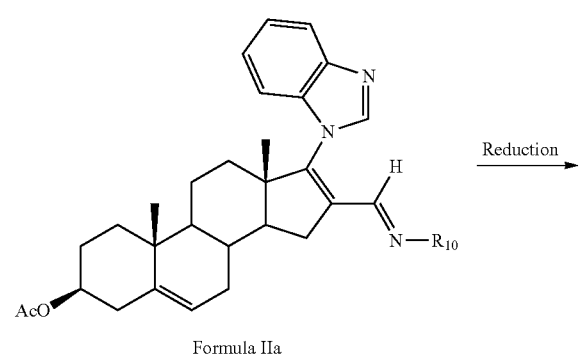

Formula IIa

Formula II a. allowing a compound of Formula B to react with a substituted amine $R_{10}NH_2$ under conditions that are effective for synthesizing a compound of Formula IIa; and
b. reducing the compound of Formula IIa;
wherein $R_{10}$ can be alkyl or aryl, optionally substituted by one or more $R_{11}$ substituents; and $R_{11}$ can be halogen, alkoxy, or CN.

In some cases, the compound of Formula IIa can be reduced by $NaBH_4$.

In yet another aspect, the present disclosure provides a method for synthesizing a compound or pharmaceutically acceptable salt of Formula III, comprising:

Formula C

Formula III allowing a compound of Formula C to react with an acylating agent $R_5C(O)Y$ under conditions that are effective for synthesizing a compound of Formula III; wherein $R_5$ can be heteroaryl, arylalkyl, cycloalkenyl, alkoxyalkyl, optionally substituted with one or more $R_{12}$ substituents; and $R_{12}$ can be $-(CH_2)_n-CO_2H$, wherein n is 0, 1, 2, or 3; with the proviso that $R_5$ is not imidazole.

In some cases, the acylating agent $R_5C(O)Y$ can be an activated ester. In other cases, Y can be $-OC(O)R_5$. In further cases, Y can be $R_5$.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 9 is a synthetic scheme for the synthesis of C-17 benzimidazole compounds.

FIG. 11 a synthetic scheme for the synthesis of C-3 modified compounds.

DETAILED DESCRIPTION

Design Strategy

Using structure activity analysis, a series of novel C-3, C-16 and C-17 galeterone analogs were prepared and evaluated for their effects on the modulation of the androgen receptor (AR).

Figure 1:
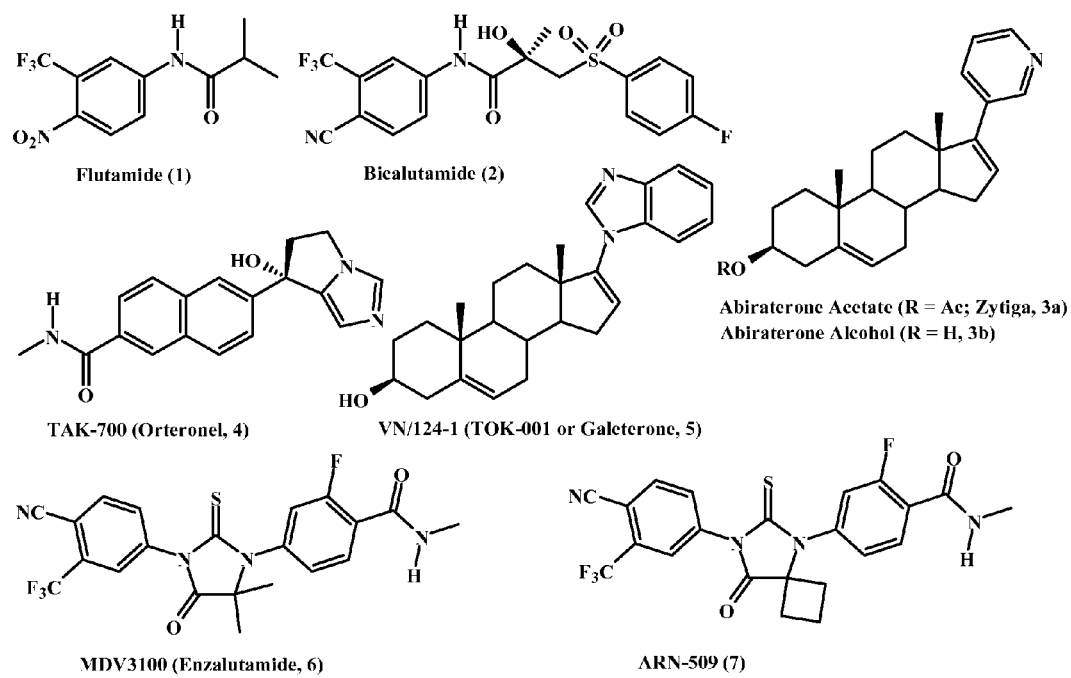
FIG. 1 illustrates the chemical structures of flutamide (1), bicalutamide (2), abiraterone acetate (Zytiga, 3a), abiraterone alcohol (3b), TAK-700 (Orteronel, 4), VN/124-1 (TOK-001 or Galeterone, 5), MDV3100 (Enzalutamide, 6) and ARN-509 (7).
Figure 2:
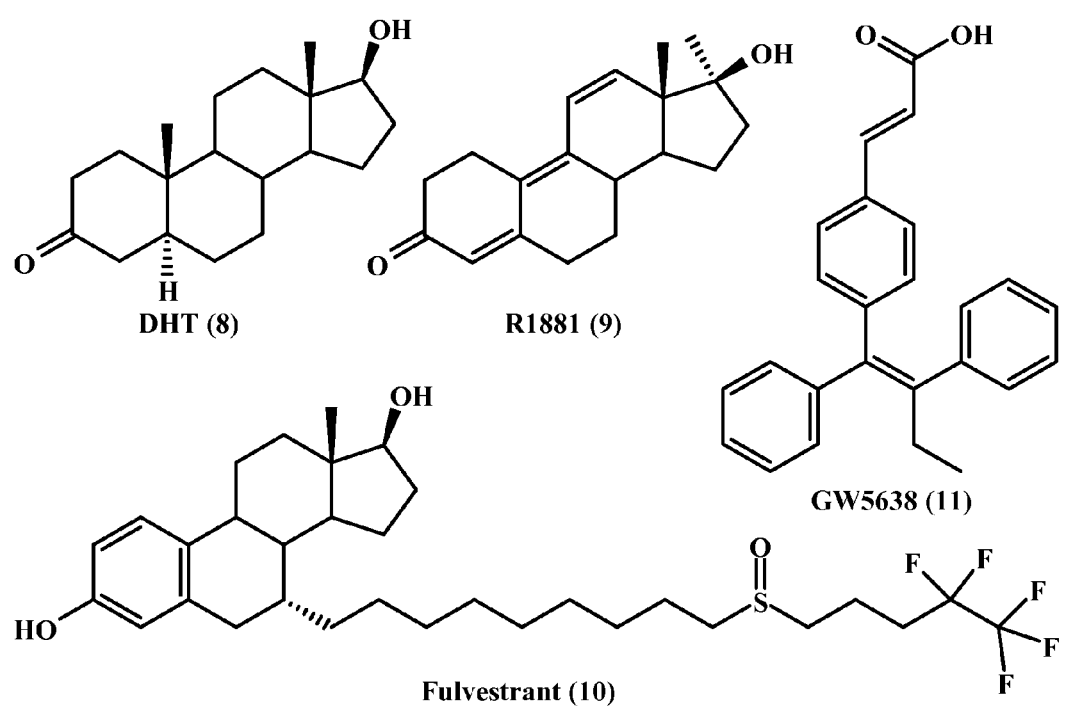
FIG. 2 illustrates the chemical structures of dihydrotestosterone (DHT, 8), metribolone (R1881, 9), fulvestrant (10) and GW5638 (11).

On the basis that compound 5 binds to the AR ligand binding domain (LBD) to induce AR degradation, the published data of crystal structures of steroid ligand dihydrotestosterone (DHT, 8) and of metribolone (R1881, 9) (FIG. 2) bound to AR LBD were examined. The hydrogen bonding interaction with Arg752 and Gln711 on one end (polar function at position C-3 of steroidal nucleus) and hydrogen bond to Asn705 and Thr877 on the other end (polar function at C-17 position of steroid scaffold) of the LBD may constitute the most important recognition elements for ligand affinity. Furthermore, previous studies have described the critical role of helix-12 in conformational changes that can induce antagonism in various nuclear receptors. It has been hypothesized that pushing helix 12 into an open conformation is the mechanism leading to antagonism for estrogen receptor alpha (ERα) and other nuclear receptors. Indeed, the distortion of helix-12 in the ERα structure complexed with known ERα down-regulators such as fulvestrant (10) and GW5638 (11) (FIG. 2) can be critical for their receptor degradation activity. Following the binding of compound 5 to the LBD of AR, the bulky C-17 benzimidazole (BzIm) group of 5 may cause distortion of helix-12 to induce AR degradation. Modifications that allow for additional interactions between a small molecule and receptor may appear to play key determinants for designing new AR down-regulators with potential clinical use. Furthermore, synthetic modifications of 5 were considered because the resulting fundamental chemical and physical changes may affect molecular shapes, bond angles, and partition coefficients. Different substituents can have different hydrophobic interactions, size, and electrostatic effects that can influence interaction of a ligand with its target receptor. These rational considerations provided the impetus for the systematic modifications of moieties tethered to C-17, C-16 and C-3 as described below.

C-17 Modifications:

To explore the structure activity relationship (SAR) of the C-17 benzimidazole moiety of 5, analogs with varied ring nitrogen atoms, increased aliphatic/aromatic hydrophobicity, and aromatic substituents to generate compounds 16-22 were designed and synthesized, as outlined in FIG. 9.

C-16 Modifications:

Several C-16 substituted analogs (compounds 25, 28 and 31) of 5, tethered with bulky aliphatic and aromatic groups (FIG. 10) were designed and synthesized.

Figure 3:
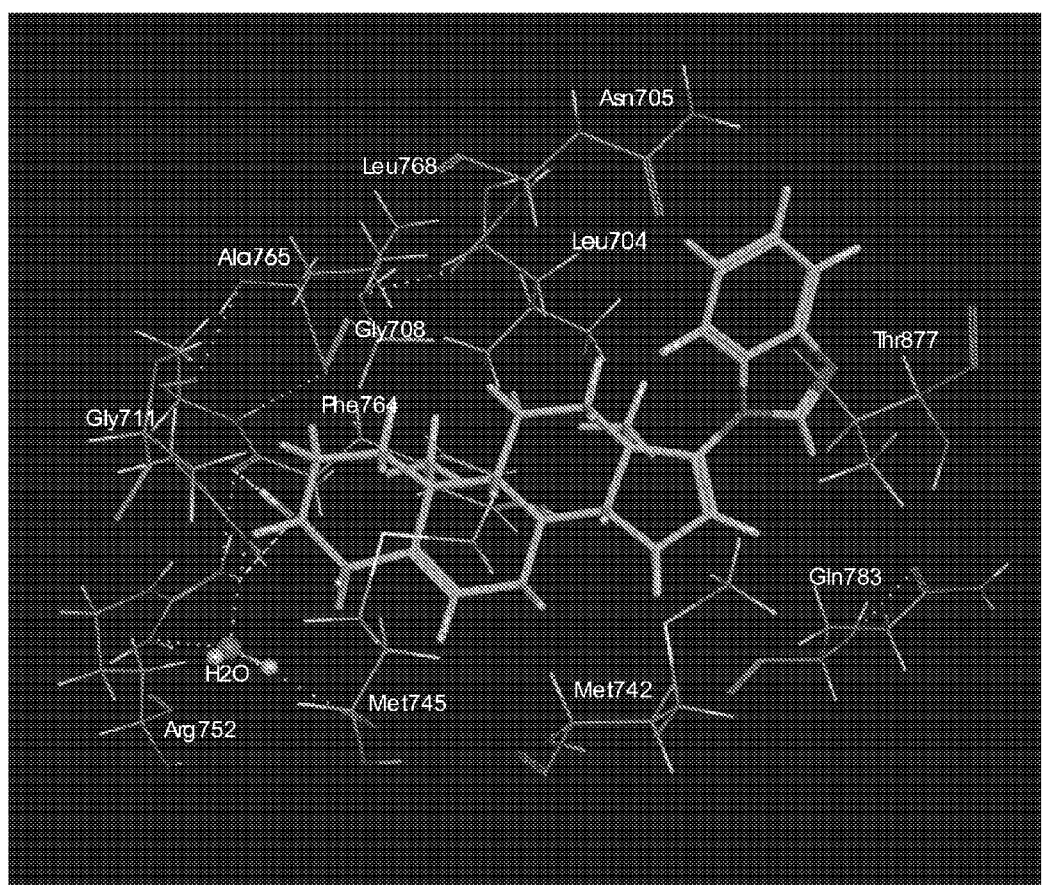
FIG. 3 provides a stereo view of the binding mode of 5 (cap, green) in the active site hAR.

C-3 Modifications:

Molecular docking of 5 with human androgen receptor (hAR) ligand binding domain shows that C-3 hydroxyl group forms multiple hydrogen bonding with Arg-752 and Phe764 (FIG. 3). Arginine is a polar hydrophilic amino acid which contains a positively charged guanidine group. On the basis of the hypothesis that any substitution at C3 which increases interaction with Arg752 may increase AR down-regulating activity, various C-3 modified compounds were designed and synthesized (33-49, FIG. 11).

Compounds and Pharmaceutically Acceptable Salts

In one aspect, the present disclosure provides a compound of Formula I:

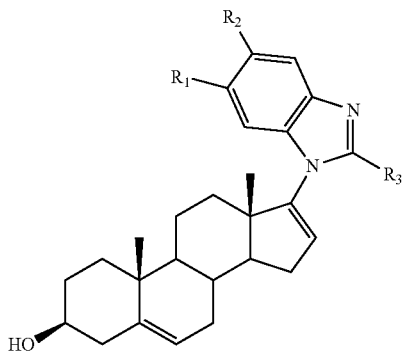

or pharmaceutically acceptable salt thereof,
wherein each of $R_1$ and $R_2$ is independently hydrogen, alkoxy, or CN; $R_3$ is hydrogen or halo; and wherein at least one of $R_1$, $R_2$, $R_3$ is not hydrogen.

In some cases, $R_1$ can be CN. In other cases, $R_2$ can be CN. In yet other cases, $R_1$ can be alkoxy (e.g. methoxy). In yet other cases, $R_3$ can be halo (e.g. chloro).

Exemplary compounds of Formula I include but are not limited to:

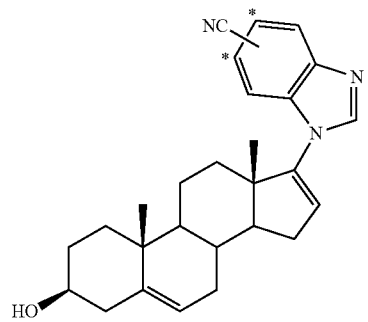

18

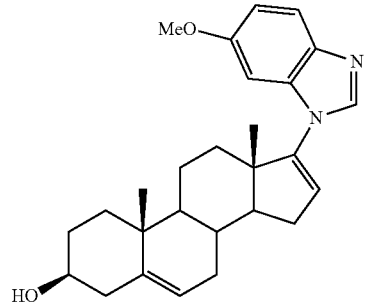

19

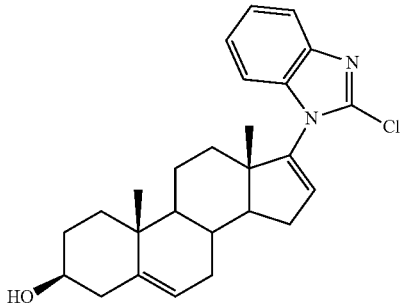

22

In another aspect, the present disclosure provides a compound of Formula II:

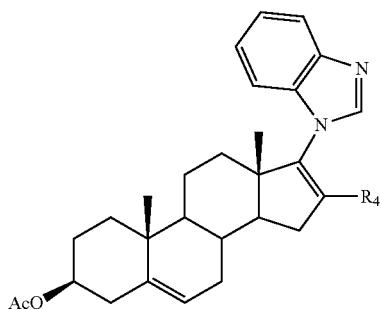

or pharmaceutically acceptable salt thereof, wherein $R_4$ is —$CNHR_{10}$ or —$C$=$NR_{10}$; $R_{10}$ is alkyl or aryl, optionally substituted by one or more $R_{11}$ substituents; and $R_{11}$ is halogen, alkoxy, or CN.

In some cases, $R_4$ can be —$CNHR_{10}$. In other cases, $R_4$ can be —$C$=$NR_{10}$. In some examples, $R_{10}$ can be alkyl (e.g. isopentyl). In other examples, $R_{10}$ can be aryl (e.g. phenyl). In further examples, $R_{10}$ can be further substituted with one or more alkoxy groups (e.g. dimethoxy).

Exemplary compounds of Formula II include but are not limited to:

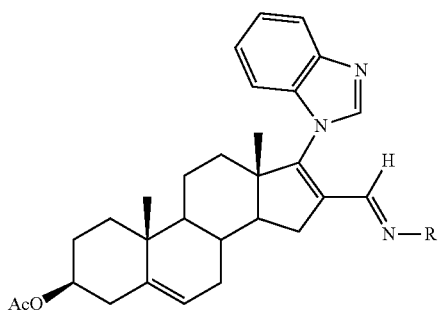

23, R = isopentyl
26, R = phenyl
29, R = 3,4-dimethoxy benzene

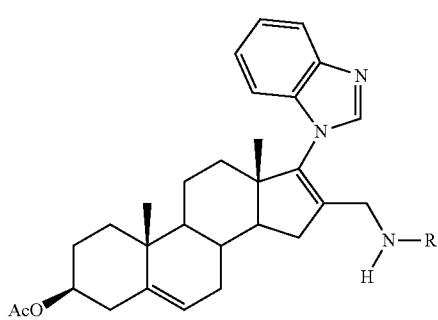

24, R = isopentyl
27, R = phenyl
30, R = 3,4-dimethoxy benzene

In yet another aspect, the present disclosure provides a compound of Formula III:

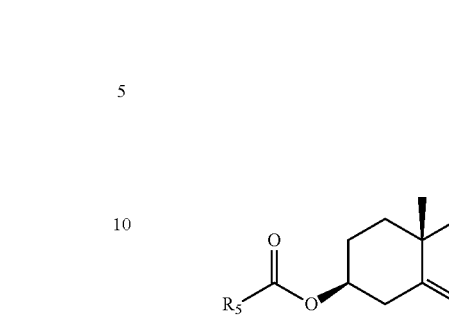

or pharmaceutically acceptable salt thereof, wherein $R_5$ is heteroaryl, arylalkyl, cycloalkenyl, alkoxyalkyl, optionally substituted with one or more $R_{12}$ substituents; $R_{12}$ is —$(CH_2)_n$—$CO_2H$, wherein n is 0, 1, 2, or 3; with the proviso that $R_5$ is not imidazole.

In some cases, $R_5$ can be heteroaryl. In some examples, $R_5$ can be pyridyl (e.g. 1-pyridyl, 2-pyridyl, 3-pyridyl). In other examples, $R_5$ can be triazole. In other cases, $R_5$ can be arylalkyl (e.g. benzyl). In yet other cases, $R_5$ can be cycloalkenyl (e.g. cyclohexenyl). In further cases, $R_5$ can be alkoxyalkyl (e.g. methoxymethyl). In various examples, $R_{12}$ can be —$CO_2H$ or —$CH_2CO_2H$.

Exemplary compounds of Formula III include but are not limited to:

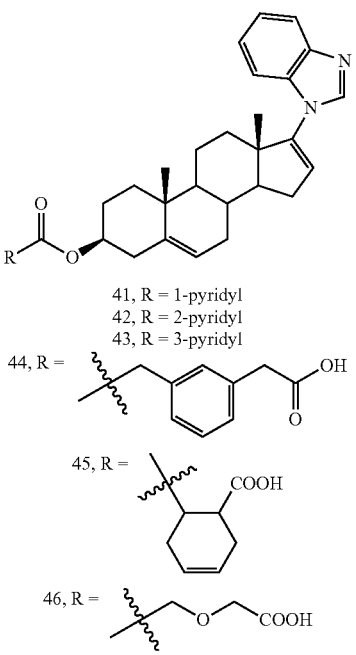

41, R = 1-pyridyl
42, R = 2-pyridyl
43, R = 3-pyridyl

44, R = 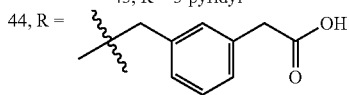

45, R = 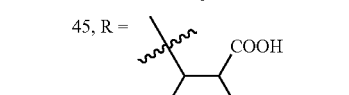

46, R = 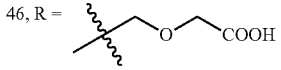

-continued

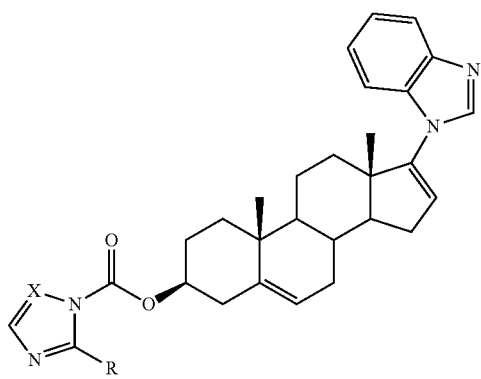

49, R = H, X = N

-continued

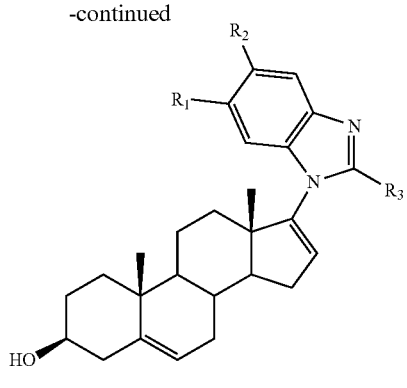

Formula I

Reaction Schemes

The compounds and pharmaceutically acceptable salts disclosed herein may be prepared by the routes described below. Materials used herein are either commercially available or prepared by synthetic methods generally known in the art. These schemes are not limited to the compounds listed or by any particular substituents employed for illustrative purposes. Numbering does not necessarily correspond to that of claims or other tables.

In one aspect, the present disclosure provides a method for synthesizing a compound of Formula I by allowing a compound of Formula A to react with a benzimidazole of Formula D under conditions that are effective for synthesizing a compound of Formula Ia:

wherein X can be halo; each of $R_1$ and $R_2$ can be independently hydrogen, alkoxy, or CN; $R_3$ can be hydrogen or halo; and wherein at least one of $R_1$, $R_2$, $R_3$ is not hydrogen. The compound of Formula A can react with the benzimidazole under basic conditions. The compound of Formula Ia can then be deformylated and hydrolyzed to afford the compound of Formula I. In some examples, the deformylation can be in the presence of a catalyst. For example, the catalyst can be a Pd catalyst (e.g. 10% Pd on carbon). In some examples, the hydrolysis can be performed in the presence of an aqueous base.

In another aspect, the present disclosure provides a method for synthesizing a compound of Formula II by allowing a compound of Formula B to react with a substituted amine $R_{10}NH_2$ under conditions that are effective for synthesizing a compound of Formula IIa:

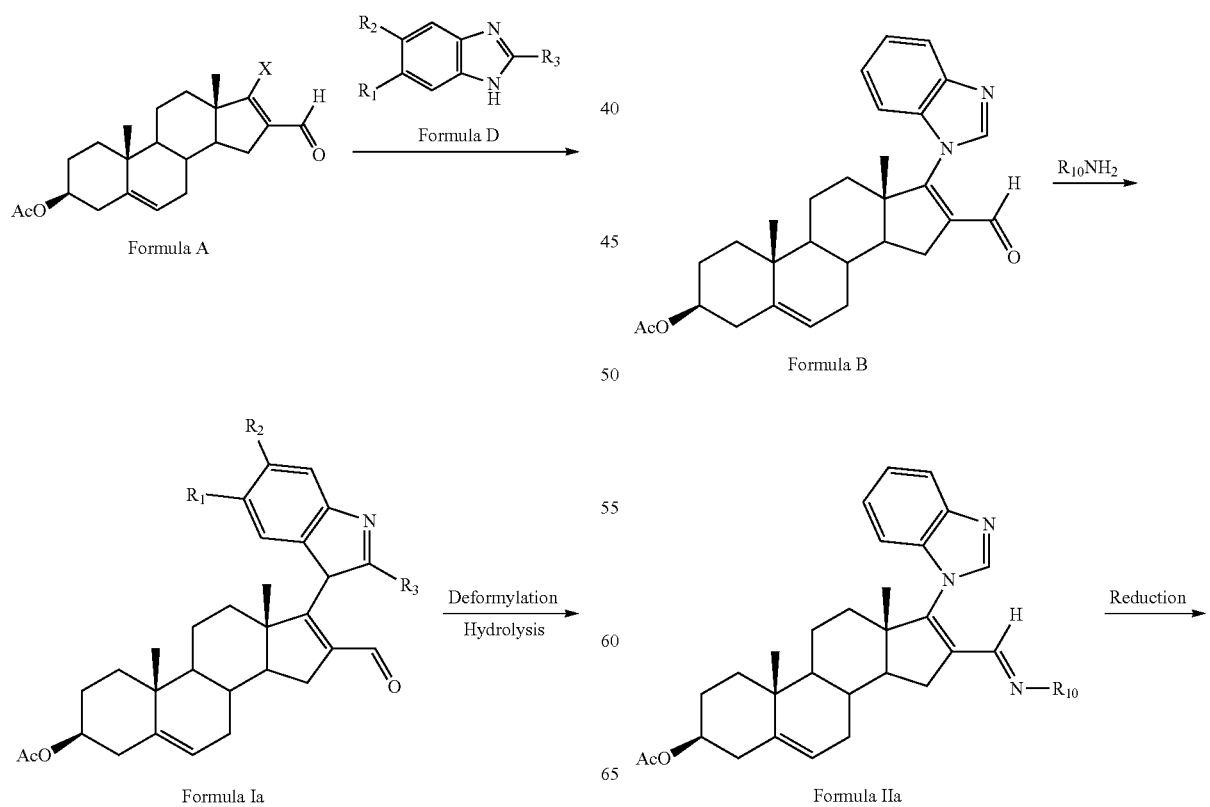

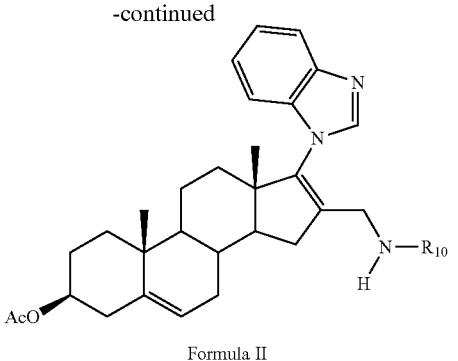

Formula II wherein $R_{10}$ can be alkyl or aryl, optionally substituted by one or more $R_{11}$ substituents; and $R_{11}$ can be halogen, alkoxy, or CN. The compound of Formula IIa can then be reduced to afford the compound of Formula II. In some cases, the compound of Formula IIa can then be reduced by a reducing agent (e.g. $NaBH_4$).

In yet another aspect, the present disclosure provides a method for synthesizing a compound of Formula III allowing a compound of Formula C to react with an acylating agent $R_5C(O)Y$ under conditions that are effective for synthesizing a compound of Formula III:

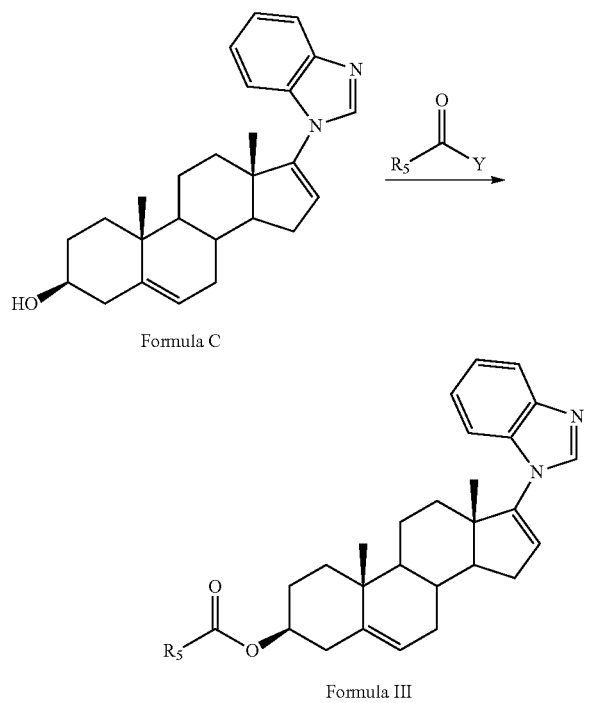

Formula C

Formula III wherein $R_5$ can be heteroaryl, arylalkyl, cycloalkenyl, alkoxyalkyl, optionally substituted with one or more $R_{12}$ substituents; and $R_{12}$ can be —$(CH_2)_n$—$CO_2H$, wherein n is 0, 1, 2, or 3; with the proviso that $R_5$ is not imidazole. In some cases, the acylating agent $R_5C(O)Y$ can be an activated ester (e.g. Y=DMAP). In other cases, the acylating agent $R_5C(O)Y$ can be an acid anhydride (e.g. Y=—$OC(O)R_5$). In yet other cases, Y can be $R_5$ (e.g. $R_5$=triazole).

Compositions and Methods

The present disclosure also provides a pharmaceutical composition comprising a pharmaceutically acceptable carrier and one or more of the compounds or salts discussed above. Suitable pharmaceutically acceptable carriers described herein, for example, vehicles, adjuvants, excipients, and diluents, are well-known to those skilled in the art and are readily available to the public. The choice of carrier will be determined, in part, by the particular composition and by the particular method used to administer the composition. Accordingly, there are a wide variety of suitable formulations of the pharmaceutical compositions of the present invention.

The present disclosure also relates to method of treating diseases or conditions, such as cancer or other urogenital diseases and conditions, including, without limitation, breast cancer, prostate cancer, other urogenital cancers, prostate hyperplasia, or other androgen-related diseases or conditions, by administering to a subject in need thereof an effective amount of a compound or salt in accordance with the present disclosure. The term "treating" is used conventionally, e.g., the management or care of a subject for the purpose of combating, alleviating, reducing, relieving, improving, etc., one or more of the symptoms associated with the prostate disease. Examples of prostate diseases that can be treated include, e.g., prostatic hyperplasia (BPH), and prostate cancer (e.g., prostatic adenocarcinoma). The treatment can be prophylactic or therapeutic. "Prophylactic" refers to any degree in inhibition of the onset of a cellular disorder, including complete inhibition, such as in a patient expected to soon exhibit the cellular disorder. "Therapeutic" refers to any degree in inhibition or any degree of beneficial effects on the disorder in the mammal (e.g., human), e.g., inhibition of the growth or metastasis of a tumor.

One skilled in the art will appreciate that suitable methods of administering a compound or salt of the present disclosure to an animal, e.g., a mammal such as a human, are known. Although more than one route can be used to administer a particular composition, a particular route can provide a more immediate and more effective result than another route.

Formulations suitable for oral administration can consist of (a) liquid solutions, such as an effective amount of one or more compound or salt of this disclosure dissolved in a diluent, such as water or saline, (b) capsules, sachets or tablets, each containing a predetermined amount of the active ingredient, as solids or granules, (c) suspensions in an appropriate liquid, and (d) suitable emulsions.

Tablet forms can include one or more of lactose, mannitol, cornstarch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically acceptable and compatible carriers. Lozenge forms can comprise the active ingredient in a flavor, usually sucrose and acacia or tragacanth, as well as pastilles comprising the active ingredient in an inert base, such as gelatin and glycerin or sucrose and acacia emulsions, gels, and the like containing, in addition to the active ingredient, such carriers as are known in the art.

The compound or salt of the disclosure, alone or in combination with other suitable components, can be made into aerosol formulations to be administered via inhalation. These aerosol formulations can be placed into pressurized acceptable propellants, such as dichlorodifluoromethane, hydrofluorocarbon (such as HFC 134a and/or 227), nitrogen, and the like.

Formulations suitable for parenteral administration include aqueous and non-aqueous solutions, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried condition requiring only the addition of the sterile liquid carrier, for example, water, for injections, immediately prior to use. Extemporaneous injection solutions and suspensions can be prepared from sterile powders, granules, and tablets of the kind previously described.

The dose administered to an animal, particularly a human, in the context of the present invention should be sufficient to affect a therapeutic response in the animal over a reasonable time frame. The specific dose level and frequency of dosage may vary, depending upon a variety of factors, including the activity of the specific active compound, its metabolic stability and length of action, rate of excretion, mode and time of administration, the age, body weight, health condition, gender, diet, etc., of the subject, and the severity of, for example, the prostate cancer or hyperplasia. Any effective amount of the compound can be administered, e.g., from about 1 mg to about 500 mg per day, about 50 mg to about 150 mg per day, etc. In one embodiment of this invention, a suitable dosage for internal administration is 0.01 to 100 mg/kg of body weight per day, such as 0.01 to 35 mg/kg of body weight per day or 0.05 to 5 mg/kg of body weight per day. A suitable concentration of the compound in pharmaceutical compositions for topical administration is 0.05 to 15% (by weight), preferably 0.02 to 5%, and more preferably 0.1 to 3%. The compound or salt of this disclosure can be administered in such dosages in any form by any effective route, including, e.g., oral, parenteral, enteral, intraperitoneal, topical, transdermal (e.g., using any standard patch), ophthalmic, nasally, local, non-oral, such as aerosol, spray, inhalation, subcutaneous, intravenous, intramuscular, buccal, sublingual, rectal, vaginal, intra-arterial, and intrathecal, etc.

As discussed above, the compound or salt of the present disclosure can be administered alone, or in combination with any ingredient(s), active or inactive, such as with a pharmaceutically acceptable excipient, carrier or diluent. The compound or salt of the present disclosure can also be used in combination with other cancer treatments and drugs. For example, the compound or salt of this disclosure can be used as a part of or in combination with known cancer treatments such as hormone therapy, chemotherapy, radiation therapy, immunotherapy, and/or surgery. In one embodiment of this invention, one or more of the compounds or salts described above is/are used in combination with one or more known and available drugs or other compounds. Exemplary drugs and/or hormones for use in combination with the compounds or salts of this invention for treating cancer or other conditions or diseases discussed above include, without limitation, anti-androgonens such as flutamide and nilutamide; a CYP17 inhibitor such as abiraterone; luteinizing hormone-releasing hormone agonists such as leuprolide, goserelin and buserelin; drugs that prevent the adrenal glands from making androgens such as ketoconazole and aminoglutethimide; and estrogens. Other suitable and exemplary cancer drugs, common for use in chemotherapy, include, without limitation, cyclophosphamide, methotrexate, 5-Fluorouracil (5-FU), doxorubicin, carboplatin, carmustine, chlorambucil, cisplatin, cyclophosphamide, dacarbazine, ifosfamide, mechlorethamin, melphalan, procarbazine, bleomycin, doxorubicin, idarubicin mitoxantrone, chlorodeoxyadenosine, cytarabine, fludarabine, 6-mercaptopurine, methotrexate, 6-thioguanine, pentostatin, etoposide, gemcitabine, steroid creams, coritcosteroids, prednisone, and dexamethasone.

The compounds or salts of this disclosure can be administered to a patient at any time as determined by the treating physician. For example, the compounds or salts of this disclosure can be administered for treating a patient during one or more of Stages II-IV of the cancer.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

EXAMPLES

Example 1. Overall Synthetic Approach of Androgen Receptor Down-Regulating Agents In this study, twenty six novel compounds were synthesized as outlined in FIG. 9 (for C-17 modified series), FIG. 10 (C-16 modified series), and FIG. 11 (C-3 modified series).

The preparation of new 17-hetereoaryl substituted compounds (16-22) from the key intermediate, 3β-acetoxy-17-chloro-16-formylandtrosta-5,16-diene (13) followed the sequence: 17-heteroaryl-16-formyl intermediate→16-deformylated intermediate→3-deacetylated final product (not shown in FIG. 9), similar to the synthetic route to compound 5 outlined in FIG. 9. The key intermediate in the synthesis of all the compounds, 13, was prepared following a Vilsmeier-Haack reaction of the commercially available 3β-acetoxyandrost-5-en-17-one (12) with phosphoryl chloride ($POCl_3$) and dimethylformamide (DMF).

For the synthesis of 3β-acetoxy-16-formyl-17-1H-heteroaryls (14, 17a, 18a, 19a, 20a, and 22a), the corresponding heteroaryls were each treated with 13 in the presence of $K_2CO_3$ in DMF at approximately 80° C. to give the desired intermediates (structures of intermediates not shown except 14) in near quantitative yields. However, because of weak basicity of indole, we used indole-3-carbaldehyde instead for the synthesis of 17-indole-3-carbaldehyde (16a) intermediate following the same procedure with excellent yield. Attempts to condense 6-chloropurine with 13 in the presence of $K_2CO_3$ in DMF resulted in inseparable $N^9/N^7$ isomers (~6/4 ratio as indicated by TLC) in very low yield. Therefore, a $N^9$-purine alkylation procedure was used, in which 13 was reacted with 6-chloropurine in presence of tetrabutylammonium fluoride (TBAF) in THF at 50° C. to give the desired intermediate (21a) in excellent yield. TLC analysis indicated that $N^7$-purine alkylation was almost negligible and the $N^9$-purine was easily purified following recrystallization in ethanol. The positional isomers of the 16-formyl derivatives (6-methoxy-BzIm 19a1 and 5-methoxy-BzIm 19a2) were separated at this stage and their structures were confirmed on the basis of reported aromatic proton resonances for related 5- and 6-methoxy benzyl compounds.

Various attempts to separate positional isomers of 5(6) nitrile-benzimidazole intermediates of compound 18 at all stages were unsuccessful. The 5(6)-nitrile-benzimidazole and 2,3-diaminonaphthalene required for synthesis of 18a and 20a were synthesized starting from 3,4-diaminobenzonitrile and benzo[f]benzimidazole respectively by refluxing with formic acid. The 16-formyl intermediates (14, 17a-21a; only structure of 14 shown) were each smoothly deformylated with 10% palladium on activated charcoal (Pd/C) in refluxing benzonitrile to give the corresponding deformylated compounds 15, 17b, 18b, 19b, 20b and 21b, respectively (structures not shown except 15) in high yields. Similarly, the two formyl groups of 17-indole-3-carbaldehyde intermediate (16a) were deformylated with 10% Pd/C as described above with good yield to give 16b. Deformylation of 22a was achieved by refluxing with readily available chlorotris(triphenylphosphine) rhodium(I) in toluene to give 22b in low yield. Unexpectedly, the 5-methoxy-16-formyl derivative 19a2 did not undergo deformylation using both methods. Hydrolysis of 15, 16b-22b with 10% methanolic-KOH gave target compounds 5, 16, 17, 18, 19, 20, 21 and 22, respectively in high yields.

Figure 10:
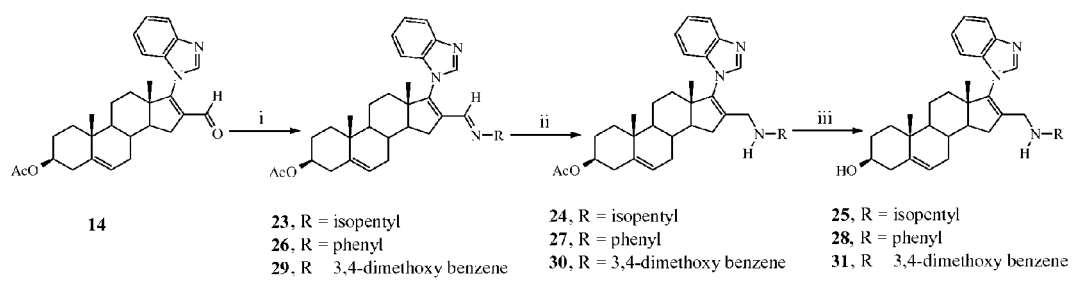
FIG. 10 is a synthetic scheme for the synthesis of C-16 substituted compounds.

The C-16 substituted compounds were synthesized starting from 14 as illustrated in FIG. 10. The intermediate imines 23, 26 and 29 were synthesized by refluxing i-pentylamine, aniline and 3,4-dimethoxyaniline, respectively with 14 in ethanol in presence of molecular sieves. Subsequent reduction of these imines with sodium borohydride (NaBH$_4$) in ice-cold methanol gave 3-acetoxy-16-alkylamine intermediates 24, 27 and 30, respectively. Following hydrolysis of the 3β-acetoxy groups in compounds 24, 27 and 30, the desired 16-substituted compounds, 25, 28, and 31, respectively, were obtained in excellent yields.

The C-3 modified compounds were synthesized as depicted in FIG. 13. Δ$^4$-3-Oxo compound (32) was synthesized via modified Oppenauer oxidation of 5 by using N-methylpiperidone and aluminum isopropoxide. Oxidation of 5 with Dess-Martin periodinane in dichloromethane (DCM) afforded the Δ$^5$-3-oxo compound 33 in 70% yield. The mesyl (34) and tosyl (35) derivatives of 5 were readily synthesized by reacting with methanesulfonyl and toluenesulfonyl chloride, respectively. The C-3 oxime derivatives (hydroxime: 36, phenyloxime: 37, methyloxime: 38 and benzyloxime: 39) were obtained by refluxing ketone (32) with the respective substituted hydroxylamine hydrochloride, using ethanol/methanol solvent mixture in presence of sodium acetate. Of all oximes, only biologically active oxime (36) was further purified to separate E- and Z-geometrical isomers by combined purification methods (column chromatography, preparative TLC, and recrystallization). Addition of MeLi to the C-3-keto group of 32 afforded two distereomeric (3α- and 3β) alcohols (40) which we did not separate due to modest biological activity.

The ester derivatives (41-46) of 5 were synthesized from 5 by two different methods as described below. The pyridinecarboxylates (41, 42 and 43) and carboxylate of 1,3-phenyldiacetic acid (44) of 5 were prepared using the mixed anhydride method via condensations with the respective anhydrides (pyridinecarboxylic acid/1,3-phenyldiacetic acid and 2-methyl-6-nitrobenzoic) in the presence of 4-dimethylaminopyridine (DMAP) and triethylamine (TEA) with varying yields (39-90%). The ester 45 (72% yield) and 46 (28% yield) were synthesized by refluxing 1,2,3,6-tetrahydrophthalic and diglycolic anhydrides respectively with 5 in the presence of DMAP in pyridine. Finally the carbamates (imidazole: 47, 2-methylimidazole: 48 and 1,2,4-triazole: 49) were synthesized in modest to high yield (67-80%) by reacting 5 with 1,1-carbonylbis(2-methylimidazole) (CDI) and carbonylditriazole (CDT), respectively in acetonitrile and DMC solvent mixture. The compounds described were rigorously characterized by physical and spectroscopic (IR, $^1$H and $^{13}$C NMR, and HRMS) analysis (see Example 8 for details). Most of the novel compounds were then subjected to in vitro biological activity studies as described in detail in the following sections.

Example 2. Biological Effects of Compounds on Transcriptional Activation of Androgen Receptor After synthesizing the compounds, a luciferase reporter assay was used to determine whether the novel compounds also affect AR transcriptional activation (screening assay). Specifically, a luciferase experiment utilizing LNCaP cells dual transfected with the probasin luciferase reporter construct ARR2-luc and the Renilla luciferase reporting vector pRL-null was used.

The LNCaP cells were purchased from American Type Culture Collection—ATCC (Rockville, Md., USA). Cells were maintained in ATCC recommended culture media with 10% fetal bovine serum (FBS) (Atlanta Biologicals, Lawrenceville, Ga., USA) and 1% penicillin/streptomycin (invitrogen). Cells were grown as a monolayer in T75 or T150 tissue culture flasks in a humidified incubator (5% CO$_2$, 95% air) at 37° C. CWR22rv1 cells are a gift from Dr. Marja Nevalainen of Thomas Jefferson University, Philadelphia.

For the transcriptional activation luciferase assay, LNCaP cells were transferred to steroid-free medium 3 days before the start of the experiment and plated at 1×10$^5$ per well in steroid-free medium. The cells were dual transfected with ARR2-Luc and the Renilla luciferase reporter vector pRL-null. After a 24-h incubation period at 37° C., the cells were incubated in fresh phenol red-free RPMI 1640 containing 5% charcoal-stripped fetal bovine serum and treated with 10 nmol/L dihydrotestosterone, ethanol vehicle, and/or the selected compounds in triplicate. After an 18-h treatment period, the cells were washed twice with ice-cold Dulbecco's PBS and assayed using the Dual Luciferase kit (Promega) according to the manufacturer's protocol. Cells were lysed with 100 µL of luciferase lysing buffer, collected in a microcentrifuge tube, and pelleted by centrifugation. Supernatants (20 µL aliquots) were transferred to corresponding wells of opaque 96-well multiwall plates. Luciferase Assay Reagent was added to each well, and the light produced during the luciferase reaction was measured in a Victor 1420 scanning multiwell spectrophotometer (Wallac, Inc.). After measurement, Stop and Glo reagent (Promega) was added to quench the firefly luciferase signal and initiate the Renilla luciferase luminescence. Renilla luciferase luminescence was also measured in the Victor 1420. The results are presented as the fold induction (i.e., the relative luciferase activity of the treated cells divided by that of the control) normalized to that of the Renilla.

Figure 4:
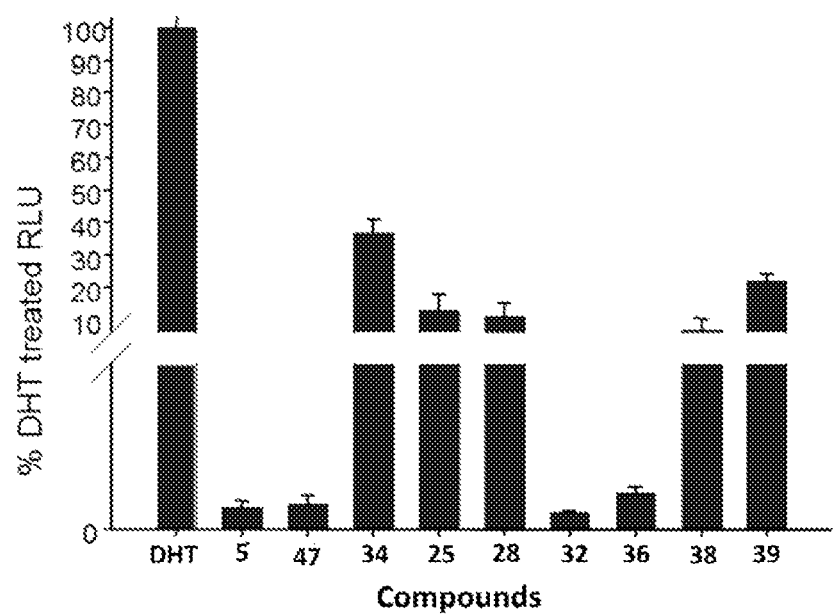
FIG. 4 summarizes the effects of the compounds on dihydrotestosterone (DHT)-stimulated transcription of AR.

Luciferase expression was increased by approximately 100-fold after 10 nM DHT treatment for 24 hours. The ability of the novel compounds (10 µM) to affect DHT mediated AR transcription was assessed. FIG. 4 shows the effects of our most potent compounds. These compounds were able to substantially inhibit DHT mediated transcription, with inhibition ranging from ~65-100%.

Example 3. Androgen Receptor Binding Assays

Figure 5A:
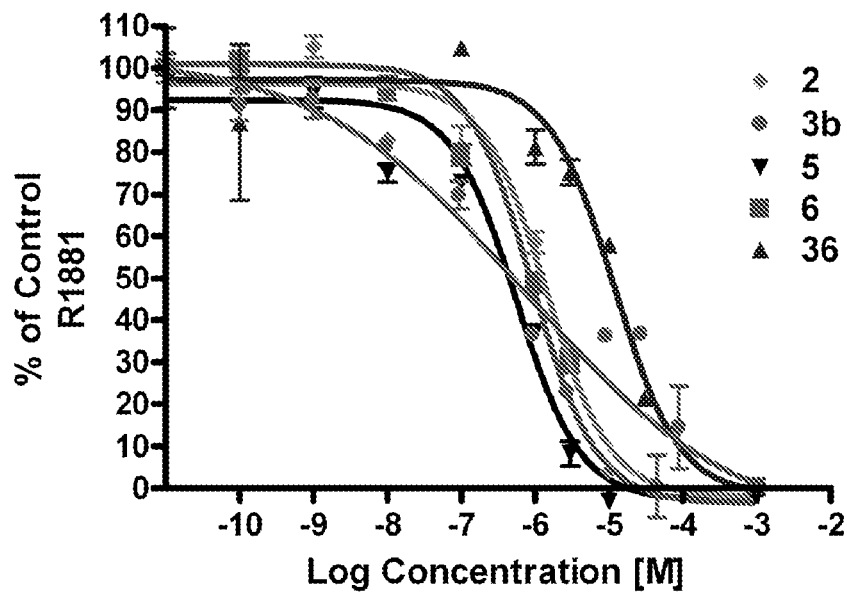
FIG. 5A illustrates the competitive inhibition of [3H] R1881 binding of compounds 2, 3b, 5, 6 and 36 to AR in LNCaP cells.

In addition to AR down-regulation, compound 5 reduces androgen action through inhibition of androgen binding and subsequently reduces AR mediated transcriptional activity. Whole cell competitive binding assays with the synthetic ligand methyltrienolone (R1881) were used to assess the AR binding affinities of the novel compounds in comparison to 5, and the FDA approved anti-androgens bicalutamide (2) and enzalutamide (6), and abiraterone alcohol (3b) as shown in FIG. 5A.

The androgen receptor competitive binding assays were performed with the synthetic androgen methyltrienolone [$^3$H]R1881. Wells in 24-well multiwell dishes were coated with poly-1-lysine (0.05 mg/ml) for 30 minutes, rinsed with sterilized, distilled water, and dried for 2 hours. To determine the kinetics of [$^3$H]R1881 binding to the LNCaP AR cells were plated (2-3×10$^5$ cells/well) in 24 well multiwell dishes in steroid-free medium and allowed to attach. The following day the medium was replaced with serum-free, steroid free RPMI supplemented with 0.1% BSA and containing [$^3$H]R1881 (0.01-10 nM) in the presence or absence of a 200 fold excess of cold DHT, to determine nonspecific binding, and 1 μM triamcinolone acetonide to saturate progesterone and glucocorticoid receptors. Following a 2 hour incubation period at 37° C., cells were washed twice with ice-cold DPBS and solubilized in DPBS containing 0.5% SDS and 20% glycerol. Extracts were removed and cell associated radioactivity counted in a scintillation counter. The data was analyzed, including $K_d$ and $B_{max}$ determination, by nonlinear regression using Graphpad Prism software (GraphPad Software, Inc, San Diego, Calif.). When the concentration of [$^3$H]R1881 required to almost saturate AR in both cell lines was established (5.0 nM), the ability of the test compounds (1 nM-10 μM) to displace [$^3$H]R1881 (5.0 nM) from the receptors was determined as described above. The IC$_{50}$ of each compound was determined by nonlinear regression with Graphpad Prism software (GraphPad Software, Inc, San Diego, Calif.).

Figure 5B:
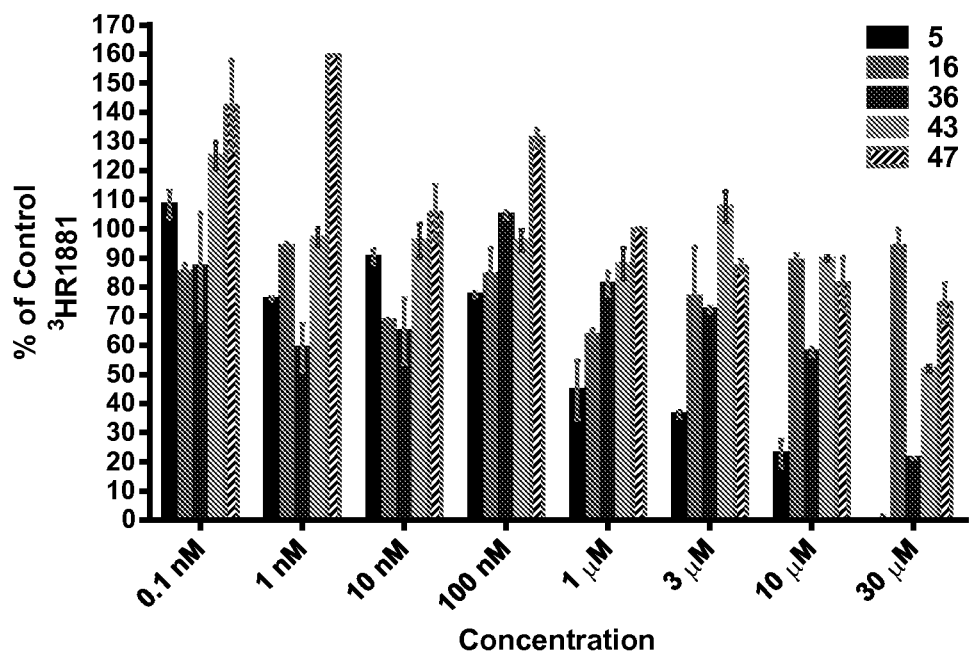
FIG. 5B illustrates the competitive inhibition of [3H]R1881 binding of compounds 5, 16, 36, 43 and 47 to AR in LNCaP cells.

The compounds with the greatest ability to displace [$^3$H]R1881 were 5 and 6, with IC$_{50}$ values of 670 nM and 915 nM, respectively. Compound 2 was slightly weaker with an IC$_{50}$ of 1.4 μM. We did not calculate the IC$_{50}$ value of 3b because of the shallow steepness of the AR binding curve, a phenomenon which indicates interaction of 3b with more than one receptor population. A recent study also noted unusual AR binding characteristics with 3b.[49] Interestingly, AR-binding assays using LNCaP cells shows that 6 was not as potent as previously reported for assays using LNCaP cells transfected with wild type AR[10] and was not significantly different from the binding affinity of bicalutamide (2). The new compounds were not as potent as 5 at inhibiting androgen binding at the concentrations tested (FIG. 5B). For example, compound 36 showed the strongest inhibition of [$^3$H]R1881 binding of all the new compounds tested (~40%) at 10 μM. At 30 μM, 36 inhibited [$^3$H]R1881 binding to by ~80%, while 43 inhibited by ~53%. The most effective AR antagonist, 47, did not strongly compete for the AR binding site, exhibiting only 20% displacement at a 30 μM concentration. It is relevant to state here that other investigators have recently reported the discovery of small-molecule androgen receptor down-regulators and anti-androgens that bind weakly to the AR.

Figure 6A:
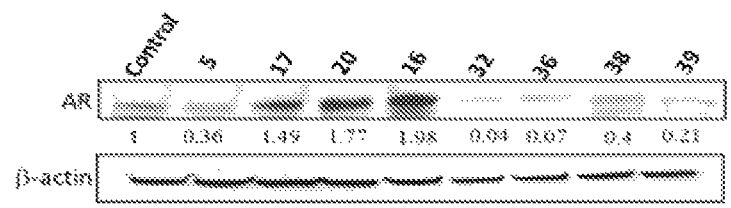
FIG. 6A-E illustrates the differential effect of compounds on suppressing AR expression in LNCaP and CWR22rv1 prostate cancer cells.
Figure 6B:
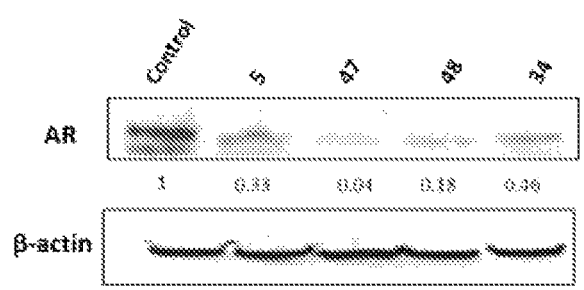
Figure 6C:
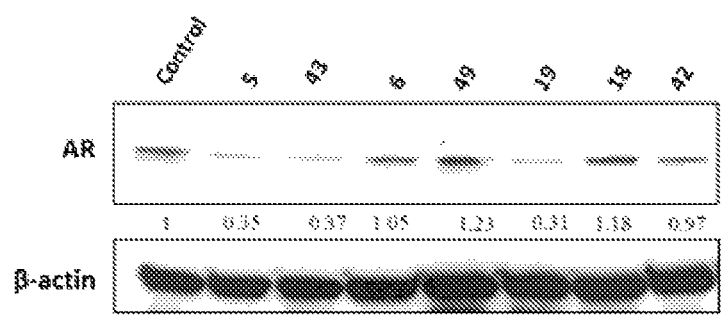

Example 4. Effects on AR Down-Regulation, Transactivation and Anti-Proliferative Activity To explore the AR down-regulation effects, LNCaP cells were treated with each of the compounds (5, 6, 16-20, 25, 28, 32, 34, 36, 38, 39, 42, 43, 47-49) of interest for 24 h followed by western blot analysis. As shown in FIGS. 6A-C most of the new compounds significantly caused AR down-regulation in LNCaP cells, with compound 47 being the most potent and proved to be greater than 8-fold more active than compound 5 at 15 μM. The ability of compounds 5 and 47 to suppress AR expression was further demonstrated by immunocytochemical analysis (FIG. 6D).

For the immunocytochemical analysis: LNCaP cells were plated in 8 chamber vessel tissue culture treated glass slide (0.025×10$^6$ cells/well), for 12 h and then treated with 5 uM of VN/124-1 or VNPT55 for 48 h. Cells were washed twice with PBS and fixed in 3.7% formaldehyde for 10 mins and permeabilized with 0.25% triton in PBS for another 5 mins after several washes. Cells blocked with 5% BSA with 0.5% NP40 in PBS and incubated with anti-AR (1:600 dilution; cell signaling) in 2.5% BSA in PBS overnight. Cells were incubated for 1 h with secondary antibody Alexa Fluor 488-conjugate anti-rabbit IgG(H+L) at 1:1000 (Cell Signaling) and nuclear counterstain for 5 mins (DAPI at 1:5000). All images were taken using the Nikon TE2000 microscope.

Figure 6D:
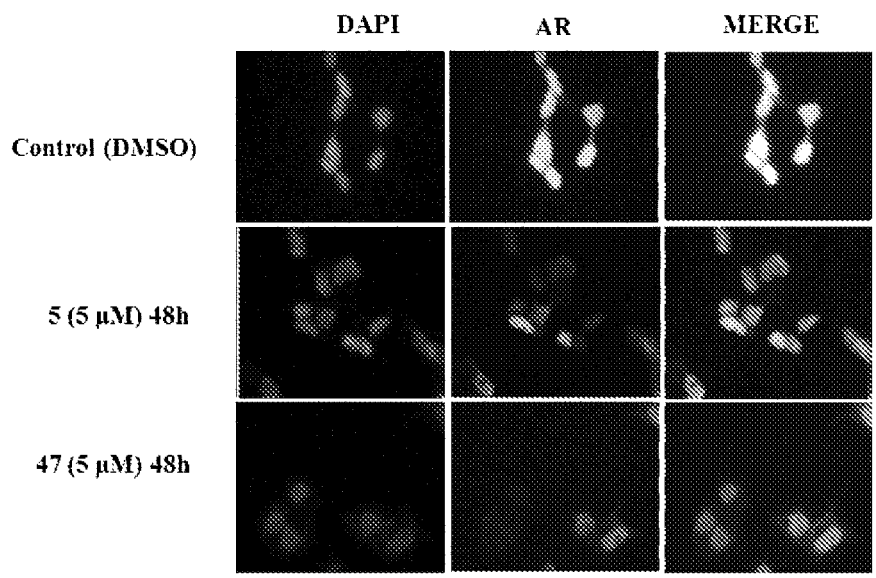

As shown in FIG. 6D, exposure of LNCaP cells to 5 μM of compounds 5 and 47 for 48 h led to significant decrease in AR levels in the nucleus, in a fashion that mimics the western blot analysis data (vide supra). These data are similar to those reported for analogs of ciglitazone, a novel class of AR-ablative agents.

Figure 6E:
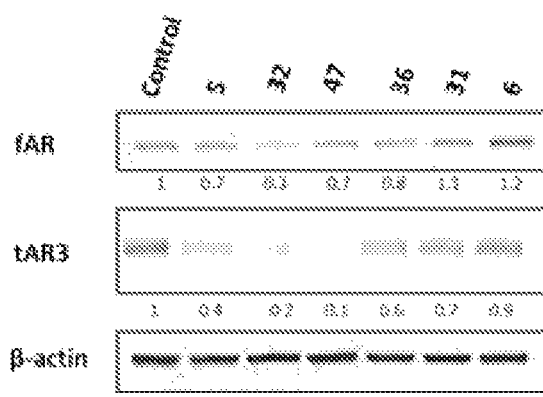

Due to the potential implication of AR splice variants lacking the ligand-binding domain (truncated AR) in driving the progression of CRPC, the effects of the compounds on the down-regulation of AR-3 (also called AR-V7) were determined. As shown in FIG. 6E, galeterone (5) and some of our new compounds, 31, 32, 36 and 47 caused significant down-regulation of both full-length and truncated AR in CWR22rv1 prostate cancer cell line. Interestingly, AR-3 was more susceptible to the compounds than the full-length AR in this cell line. In contrast, MDV3100 did not affect the expression levels of either full-length or splice variant forms of AR. A number of natural products and related analogs have been shown to degrade both full-length and truncated AR in several human prostate cancer cell lines. However, except for the curcumin analog, ASC-J9 that possesses excellent drug-like properties, most of these compounds are poor drug candidates because of modest potencies and/or toxic nature. If adequately developed, the unique AR depleting agents provided in the present disclosure may be more effective against CRPC than agents that obligatorily bind to specific region(s) of AR to elicit inactivation of AR.

Figure 7:
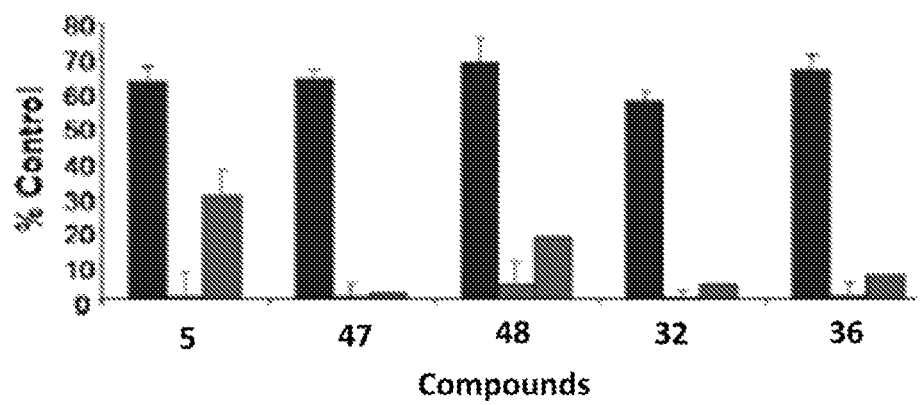
FIG. 7 summarizes the effects of compounds 5, 32, 36, 47 and 48 on: i) cell viability (blue); ii) DHT-induced AR transactivation (green); and iii) AR protein expression following treatment with 15 µM of each compound for 24 h.

To determine whether AR down-regulation or AR transcriptional deactivation (AR inactivation) was contributing to the anti-proliferative activity, LNCaP cells were treated with 15 μM of selected active compounds (5, 36, 32, 47 and 48,) for 24 hours and cell viability, AR transcriptional (luciferase) assay and AR western blot analysis were performed. As shown in FIG. 7, the down-regulation of AR and inhibition of AR mediated transcription occurs before cell growth inhibition, which suggest that compound-induced AR inactivation contributes to their anti-proliferative activities. These compounds also induced significant PARP cleavage in LNCaP and CWR22rv1 cells which suggest their abilities to induce apoptosis.

Example 5. CYP 17 Inhibition Studies

Some compounds were evaluated for their ability to inhibit CYP17 enzyme. A truncated version of human CYP17A1 (CYP171dH) was expressed in *E. coli* and then purified to homogeneity. IC$_{50}$ values of the compounds were determined from dose-response curves and are listed in Table 1.

TABLE 1

IC$_{50}$ values of select compounds for inhibition of CYP17

| Compounds | IC$_{50}$ (μM)$^a$ |
|---|---|
| 16 | 130 |
| 36 | 258 |
| 47 | 122 |
| 48 | 93.7 |
| For comparison | |
| Abiraterone alcohol (3b) | 0.206 |
| Galeterone (5) | 0.752 |
| VN/85-1 | 0.125 |

$^a$IC$_{50}$ value is the concentration of inhibitor to inhibit the CYP17 enzyme activity by 50%, each in duplicate. IC$_{50}$ values were each determined from dose-response curves.

The IC$_{50}$ values of abiraterone alcohol (3b, a CYP 17 inhibitor recently approved for prostate cancer therapy), galaterone and 3β-hydroxy-17-(1H-imidazole-1-yl)androsta-5,16-diene (VN/85-1, structure not shown, believed to be the most potent CYP17 inhibitor) were also determined in the same assay system for comparison (used as positive controls). As expected, these new compounds (16, 36, 47 and 48) with IC$_{50}$ values in the high micromolar range (93.7-258 μM) were weak inhibitors of CYP17, reinforcing the previously established structural requirements for potent steroidal CYP 17 inhibitors, including, no tolerance of bulky moieties at C-3 and appropriately positioned C-17 heterocyclic heteroatom. As expected, the well-established CYP17 inhibitors exhibited exquisite inhibition of the enzyme with IC$_{50}$ values in the nanomolar range (Table 1).

Example 6. Anti-Proliferative (Anti-Cancer) and Androgen Receptor Down-Regulating Activities: Structure Activity Relationships (SAR)

In view of the hypothesis that the extent of AR degradation induced by compound 5 and the new analogs may correlate with their ability to inhibit proliferation of prostate cancer cells (LNCaP), these two activities were assessed using Western blot analyses and MTT assays.

For the Western blot analyses, LNCaP or CWR22v1 prostate cancer cells were cultured. The cells were then treated with the indicated compounds and whole cell lysates were prepared using RIPA lysis buffer (Sigma Aldrich) and protease and phosphatase inhibitors (Sigma Aldrich). All of the antibodies were ordered from cell signaling technology. Protein content was determined using the Bradford Assay (Bio-Rad, Hercules, Calif., USA). Protein was subjected to SDS-PAGE and transferred onto nitrocellulosemembrane. Membranes were then incubated with secondary antibody (cell signaling technology) at room temperature for 1 hour. Bands were visualized by chemiluminescence (Millipore). Protein expression was normalized to β-actin and densitometry was carried out using Image J or ImageQuant 5.0 (Molecular Dynamics, Sunnyvale, Calif., USA). CWR22Rv1 cells were used for endogenous levels of splice variant AR-3. Protein levels were analyzed with respective antibodies; full length AR and β-actin antibodies were purchased from cell signaling, antibody specific for splice variant AR-3 was obtained from Dr. Yun Qiu, University of Maryland, School of Medicine, Baltimore.

For the MTT colorimetric assay, cells were seeded in 96-well plates (Corning Costar) at a density of 5×10$^3$ cells per well. The cells were then allowed to adhere to the plate for 24 hours and treated with various concentrations of compounds dissolved in 95% EtOH. The cells were treated for 7 days with renewal of test compound and media on day 4. On the 7th day, medium was renewed and MTT (3-(4,5-dimethylthiazol-2-yl)-2,5-diphenyl-2H-tetrazolium bromide) (Sigma, St Louis, Mo., USA) solution (0.5 mg MTT per ml of media) was added to the medium such that the ratio of MTT: medium was 1:10. The cells were incubated with MTT for 2 hours. The medium was then aspirated and DMSO was added to solubilize the violet MTT-formazan product. The absorbance at 562 nm was measured by spectrophotometry (Biotek Inc.).

C-17 Modification:

Indole 16 was synthesized and tested to assess the effect of decreased polarity at C17 position, due to absence of N-3 of BzIm ring. Unexpectedly, the compound caused up-regulation of AR (FIG. 6A) and completely lost anticancer activity (GI$_{50}$>100 μM, Table 2) in comparison to lead compound 5 (GI$_{50}$=3.35 μM).

TABLE 2

GI$_{50}$ values of C-17 modified compounds

| Compounds | GI$_{50}$ (μM)$^a$ |
|---|---|
| Abiraterone (3b) | 1.97 |
| Galeterone (5) | 3.35 |
| MDV3100 (6) | 5.12 |
| 16 | >100 |
| 17 | 47.72 |
| 18 | 2.81 |
| 19 | 4.26 |
| 20 | 37.10 |
| 21 | 13.48 |
| 22 | 10.13 |

$^a$The GI$_{50}$ were determined from dose-response curves (by nonlinear regression analysis using GraphPad Prism) compiled from at least three independent experiments, SEM < 10%, and represents the compound concentration required to inhibit cell growth by 50%.

Increasing the number of nitrogen C-17 heterocycle by substituting with 6-chloropurine (21), caused a 4-fold reduction in anti-proliferative activity (GI$_{50}$=13.48 μM). Introducing cyano group (18) displayed potent anti-proliferative activity (GI$_{50}$=2.81 μM), but with diminished AR down-regulation (ARD) activity. Introduction of aliphatic hydrophobicity on BzIm ring by substituting methyl group on 5, 6 position (17) resulted into substantial loss of anti-proliferative (GI$_{50}$=42.72 μM) and ARD activities, whereas substituting mono methoxy group (19) at 6$^{th}$ position of BzIm ring displayed no modulation of ARDA or anticancer activity (GI$_{50}$=4.26 μM). Increasing aromatic hydrophobicity by replacing BzIm with naphtho[2,3-d]imidazole ring (20) caused significant loss of ARDA and anticancer activity (GI$_{50}$=19.10 μM). Substituting 2-chloro BzIm (22) caused a 3-fold loss in anti-proliferative activity. None of the C17 modified molecules were superior to our lead compound 5, and this clearly indicates that the BzIm ring at C17 position of lead 5 is essential and optimal for ARDA and anti-proliferative activity.

C-16 Modification:

Tethering aliphatic hydrophobic groups (isopentyl: 25); aromatic (benzyl: 28; dimetoxybenzyl: 31) to increase bulk at C16 position resulted in significant loss of ARD and anticancer activities (GI$_{50s}$=18.31, 22.13 and >100 μM, respectively; Table 3).

TABLE 3

GI$_{50}$ values of C-16 modified compounds

| Compounds | GI$_{50}$ (μM)[a] |
|---|---|
| 25 | 18.31 |
| 28 | 22.13 |
| 31 | >100 |

[a]The GI$_{50}$ were determined from dose-response curves (by nonlinear regression analysis using GraphPad Prism) compiled from at least three independent experiments using LNCaP cells, SEM < 10%, and represents the compound concentration required to inhibit cell growth by 50%.

C-3 Modification:

In an attempt to better understand the role played by OH and O in the ARD/anti-proliferative activities of compounds 5 and 32, and to possibly achieve enhanced interaction with Arg in the AR ligand biding domain, a number of C-3 modified analogs were designed, synthesized and tested. First, oxidation of 5 or reductive alkylation of 32 to give 3-oxo-Δ$^5$ compound, 33 and 3-hydroxy-3-methyl compound, 40, respectively, lead to significant loss (~5-fold) in anti-proliferative activity (Table 4).

TABLE 4

GI$_{50}$ values of C-3 modified compounds

| Compounds | GI$_{50}$ (μM)[a] |
|---|---|
| 32 | 2.64 |
| 33 | 15.96 |
| 34 | 42.13 |
| 35 | 47.18 |
| 36 | 1.91 |
| 36E | 2.03 |
| 36Z | 1.95 |
| 37 | NT[b] |
| 38 | 3.38 |
| 39 | 5.57 |
| 40 | 13.34 |
| 41 | NT[b] |
| 42 | NT[b] |
| 43 | 2.57 |
| 44 | 7.78 |
| 45 | 8.22 |
| 46 | 9.13 |
| 47 | 0.87 |
| 48 | 5.34 |
| 49 | 6.67 |

[a]The GI$_{50}$ were determined from dose-response curves (by nonlinear regression analysis using GraphPad Prism) compiled from at least three independent experiments, SEM < 10%, and represents the compound concentration required to inhibit cell growth by 50%.
[b]Not tested due to insolubility in ethanol.

Conversion of compound 5 to the mesyl (34) and tosyl (35) derivatives also gave compounds with mediocre anti-proliferative activities, with GI$_{50}$ values of 42.13 and 47.18 μM, respectively. On the contrary, introduction of oxime moieties at C-3 yielded compounds (E/Z oxime mixtures) with similar or better activities compared to compounds 5 and 32. Thus, the simple oxime (36), and the related methyl-(38) and benzyl-(39) analogs exhibited GI$_{50}$ values of 1.91, 3.38 and 5.57 μM, respectively. The biological activities of the phenyl oxime (37) were not assessed because of its limited solubility in ethanol or DMSO. Considering the promising and superior activity of E/Z mixture of oximes 36, and the possibility that the pure E and Z had different anti-proliferative activities, it was surprising that 36E and 36Z isomers exhibited similar potencies, with GI$_{50}$ values of 2.03 and 1.95 μM, respectively.

On the basis of known ester based anticancer drugs, such as docetaxel, cabazitaxel and esters in clinical development such as bevirimat and related analogs, three pyridinecarboxylate derivatives of compound 5, including 41-43, were synthesized. Of these compounds, the isonicotinoyl derivative 43 exhibited similar anti-proliferative activity (GI$_{50}$=2.57 μM) as 5. Here again, the biological activities of compounds 41 and 42 were not assessed because of their limited solubilities in ethanol or DMSO. The related analogs tethered to lipophilic ester side chain with a carboxylic acid terminus (44-46) exhibited potencies ~2.5-fold worse than compound 5. Finally, evaluation of C-3 carbamates was performed because of: 1) precedence of drugs with carbamate moieties such as the widely use anthielmintics albendazole, fenbendazole and mebendazole; 2) the added feature of lowering the lipohilicity of compound 5, which should also increase solubilities and perhaps physiological relevance. Of the three heteroaryl carbamates tested, the imidazoly carbamate 47 with a GI$_{50}$ value of 0.87 μM was shown to be the most active, being ~4-fold superior to compound 5. Introduction of 2$^1$-methyl as in carbamate 48 caused a 6-fold decrease in activity relative to 47, similar to ~8-fold decrease in activity following replacement of the imidazole moiety with 1,2,4-triazole as exhibited by compound 49.

Example 7. Docking Studies

As stated in the design strategy section above, the docking studies were based on the well-established molecular determinants responsible for affinity of ligands to the AR. Three compounds (5, 36 and 47) were each docked into active site of AR. R1881 (9) was included as a positive control. We found that docked 9 showed similar orientation and interactions as in the published crystal structure of 9 bound to the AR (data not shown). As clearly depicted in FIG. 3, when compound 5 was modeled in the AR-LBD binding site, 5 made the crucial H-bond interaction to Arg752 and Phe764 and the steroid scaffold showed hydrophobic interactions with surrounding amino acids similar to interactions of 9 with the AR-LBD. The two nitrogen atoms of the BzIm group of 5 showed no clear interactions with Asn705 and Thr877, unlike the interaction of 9 to Asn705 and Thr877 which occurs through the 17β hydroxyl group. The observed moderate binding affinity of 5 to AR (IC$_{50}$=680 nM versus IC$_{50}$=4 nM for DHT) may be due to subtle albeit favorable hydrophobic/hydrophilic interactions between the BzIm group of 5 and other surrounding amino acid residues in the active site.

Figure 8A:
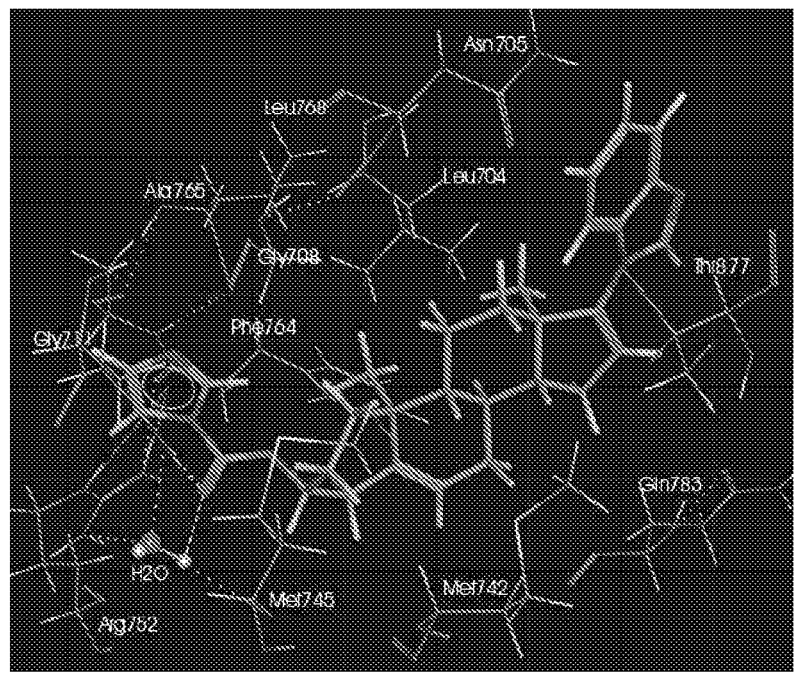
FIG. 8A provides a stereoview of the binding mode of 47 (cap, brick red) in the active site of AR.
Figure 8B:
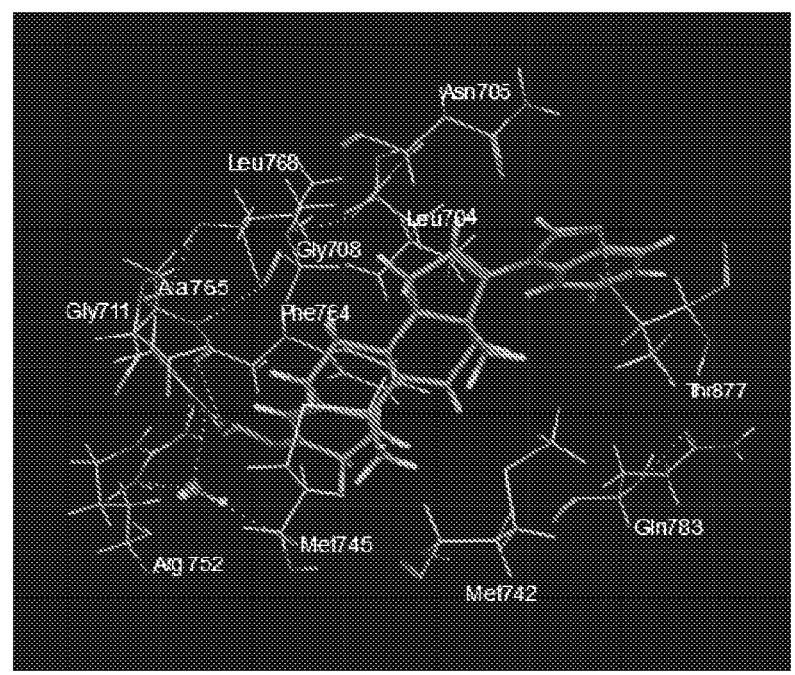
FIG. 8B provides a stereoview of the binding mode of 36 (cap, element color) in the active site of AR.

Replacing the C-3-hydroxy group of 5, with carbonylimidazole to give 47 appears to show better interactions with the key amino acid residues of the hAR LBD (FIG. 8A). The carbonyl of the carbamate group interacts directly with Gln711 and indirectly with other amino acids (Met745 and Arg752) via one H$_2$O molecule. The electron cloud on imidazole ring also interacts with Arg752. Similar to the interactions seen with 5, the two nitrogen atoms of the BzIm group of 47 showed no clear interactions with Asn705 and Thr877. Docking of the 3-oxime compound 36 to the LBD of hAR appear to show different types of interactions in which the oxygen and hydrogen atoms of the oxime show hydrogen bonds with Arg752 and Phe764, respectively (FIG. 8B). In contrast to the interactions seen with compounds 5 and 47, the N-3 of the C-17 BzIm moiety exhibited hydrogen bonding with Thr877. It would appear that the spatial arrangement among the hydrogen bonding functional groups and the steroid core of these compounds is the most appropriate for forming the necessary hydrogen bonds and hydrophobic interaction with hAR LBD. Unexpectedly, in spite of the significant hydrogen bonding networks exhibited by these compounds in these docking analyses, no significant experimental binding to AR were observed, except that our lead compound 5 exhibited moderate binding relative to the endogenous AR ligands.

Example 8. General Synthetic Procedures and Chemical Characterization of Androgen Receptor Down-Regulating Agents Materials and Methods:

Melting points (mp) were determined with a Fischer-Johns melting point apparatus and are uncorrected. Proton magnetic resonance spectra ($^1$H NMR) spectra were recorded in CDCl$_3$ or DMSO-d$_6$ at 500 or 400 MHz with Me$_4$Si as an internal standard using a Varian Inova 500 or Bruker 400 MHz spectrometers. $^{13}$C NMR spectra were recorded in CDCl$_3$ using Bruker 400 or 500 MHz spectrometers. High-resolution mass spectra (HRMS) were determined on a Bruker 12 Tesla APEX-Qe FTICR-MS by positive ion ESI mode by Ms. Susan A. Hatcher, Facility Director, College of Sciences Major Instrumentation Cluster, Old Dominion University, Norfolk, Va. Epiandrosterone acetate, and all other chemicals, reagents were purchased from Sigma-Aldrich. Dihydrotestosterone (DHT) used in the biological experiments was synthesized. All compounds were stored in the cold (0-8° C.). Silica gel plates (Merck F254) were used for thin-layer chromatography, while flash column chromatography (FCC) was performed on silica gel (230-400 mesh, 60 Å). The preparative TLC performed on Silica gel GF (Analtec 500 microns) plates. Pet ether refers to light petroleum, b.p. 40-60° C.

3β-Acetoxy-17-chloro-16-formylandrosta-5,16-diene (13)

This compound prepared from 3β-acetoxyandrost-5-en-17-one (Epinadrosterone acetate, 12) as previously described, provided spectral and analytical data as reported.

General method A: Synthesis of 3β-Acetoxy-17-(1H-heteroaryl-1-yl)-16-formylandrosta-5,16-diene (14, 16a-18a, 19a1, 19a2, 20a, and 22a)

A 25 mL RB flask equipped with a magnetic stir bar and condenser was charged with 3β-acetoxy-17-chloro-16-formylandrosta-5,16-diene (13, 0.38 g, 1 mmol), corresponding heteroaryl (3 mmol) and K$_2$CO$_3$ (0.41 g, 3 mmol) in dry DMF (~7.5 mL) was stirred at 80° C. under Ar and monitored by TLC. After cooling to room temperature, the reaction mixture was poured onto ice-cold water (50 mL) and the resulting precipitate was filtered, washed with water and dried to give crude product. Purification by the FCC [petroleum ether/EtOAc/TEA (6:4:0.3)] gave the desired pure compounds. Above listed intermediate compounds were synthesized (using reactants, reagent and solvent ratio), isolated and purified by using this method unless otherwise stated.

3β-Acetoxy-17-(1H-benzimidazol-1-yl)-16-formylandrosta-5,16-diene (14)

Compound 14 prepared by following general Method A, reacting 13 (2.5 g, 6.65 mmol) with benzimidazole (2.35 g, 19.9 mmol) in presence of K$_2$CO$_3$ (2.76 g, 19.9 mmol) in dry DMF at 80° C. for 1.5 h. Followed by FCC purification provided pure 14 with identical spectral and analytical data as we previously reported.

3β-Acetoxy-17-(3-formyl-1H-indol-1-yl)-16-formylandrosta-5,16-diene (16a)

Compound 16a prepared by following general method A, reacting 13 (1 g, 2.66 mmol) with indole-3-carbaldehyde (0.5 g, 3.44 mmol) in presence of K$_2$CO$_3$ (0.5 g, 3.62 mmol) in dry DMF (15 mL) at 80° C. for 8 h. Purification by FCC [petroleum ether/EtOAc (7:3)] gave 1.1 g (85%) of pure 16a: mp 206-208° C.; IR (Neat) 2935, 2852, 1729, 1665, 1635, 1453, 1374, 1239, 1032, 783 cm$^{-1}$; $^1$H NMR (500 MHz, CDCl$_3$) δ 1.01 (s, 3H, 18-CH$_3$), 1.09 (s, 3H, 19-CH$_3$), 2.06 (s, 3H, 3β-OCOCH$_3$), 4.65 (dt, J=12.2, 6.5 Hz, 1H, 3α-H), 5.46 (br, 1H, 6-H), 7.29 (s, 1H, 2'-H), 7.39 (m, 2H, aromatic-Hs), 7.80 (d, J=14.9 Hz, 1H, aromatic-H), 8.36 (m, 1H, aromatic-H), 9.58 (br, 1H, 16-CHO) and 10.15 (s, 1H, indole-CHO).

3β-Acetoxy-17-(5,6-dimethyl-1H-benzimidazol-1-yl)-16-formylandrosta-5,16-diene (17a)

Compound 17a prepared by following general method A, reacting 13 (0.5 g, 1.33 mmol) with 5,6-dimethylbenzimidazole (0.54 g, 4.0 mmol) in presence of K$_2$CO$_3$ (0.55 g, 4.0 mmol) in dry DMF (10 mL) at 80° C. for 5 h. Purification by FCC gave 0.46 g (70.7%) of pure 17a: mp 174-175° C.; IR (Neat) 2941, 2852, 1727, 1672, 1622, 1463, 1487, 1365, 1236, 1029, 897, 843, 717, 657 cm$^{-1}$; $^1$H NMR (400 MHz, CDCl$_3$) δ 1.06 (s, 3H, 18-CH$_3$), 1.16 (br. s, 3H, 19-CH$_3$), 2.03 (s, 3H, 3β-OCOCH$_3$), 2.35 (s, 3H, aromatic-CH$_3$) 2.38 (s, 3H, aromatic-CH$_3$), 4.64 (m, 1H, 3α-H), 5.44 (br, 1H, 6-H), 7.02 (br. s, 1H, aromatic-Hs), 7.59 (s, 1H, aromatic-H), 7.87 (s, 1H, 2'-H) and 9.60 (s, 1H, 16-CHO).

3β-Acetoxy-17-(5(6)-nitrile-1H-benzimidazol-1-yl)-16-formylandrosta-5,16-diene (18a)

Compound 18a prepared by following general method A, reacting 13 (0.5 g, 1.33 mmol) with 5(6)-nitrilebenzimidazole (0.38 g, 2.65 mmol) in presence of K$_2$CO$_3$ (0.55 g, 4.0 mmol) in dry DMF (10 mL) at 80° C. for 5 h. Purification by short column [petroleum ether/EtOAc/TEA (6:4:0.1)] gave 0.28 g (43.5%) of pure 18a: mp 146-147° C.; IR (Neat) 2935, 2226, 1726, 1673, 1470, 1238 1032, 906, 728 cm$^{-1}$; $^1$H NMR (400 MHz, CDCl$_3$) δ 1.07 (s, 3H, 18-CH$_3$), 1.19 (br. s, 3H, 19-CH$_3$), 2.04 (s, 3H, 3β-OCOCH$_3$), 4.62 (dt, J=10.1, 5.3 Hz, 1H, 3α-H), 5.44 (br, 1H, 6-H), 7.61-7.96 (m, 3H, aromatic-H), 8.21 (s, 1H, 2'-H) and 9.52 (s, 1H, 16-CHO).

3β-Acetoxy-17-(6-methoxy-1H-benzimidazol-1-yl)-16-formylandrosta-5,16-diene (19a1) and 3β-Acetoxy-17-(5-methoxy-1H-benzimidazol-1-yl)-16-formylandrosta-5,16-diene (19a2)

Compound 19a1 and 19a2 prepared by following general method A, reacting 13 (0.5 g, 1.33 mmol) with 5(6)-methoxybenzimidazole (0.59 g, 4.0 mmol) in presence of K$_2$CO$_3$ (0.55 g, 4.0 mmol) in dry DMF (10 mL) at 80° C. for 3 h. Purification by FCC [petroleum ether/EtOAc/TEA (7.5:2:0.5)] gave first less polar 6-methoxy derivative (19a1) 0.15 g (24%): mp 242-245° C.; IR (Neat) 2935, 1721, 1673, 1502, 1440, 1249, 1220, 1032, 805, 759 cm$^{-1}$; $^1$H NMR (400 MHz, CDCl$_3$) δ 1.07 (s, 3H, 18-CH$_3$), 1.18 (br. s, 3H, 19-CH$_3$), 2.03 (s, 3H, 3β-OCOCH$_3$), 3.82 (s, 3H, —OCH$_3$), 4.62 (dt, J=11.2, 6.6 Hz, 1H, 3α-H), 5.44 (t, 1H, J=1.84 Hz, 6-H), 6.70 (m, 1H, aromatic-H) 6.95 (m, 1H, aromatic-H), 7.70 (m, 1H, aromatic-H), 7.87 (s, 1H, 2'-H) and 9.61 (s, 1H, 16-CHO). Subsequently more polar 5-methoxy derivative (19a2) 0.13 g (20%): mp 228-231° C.; IR (Neat) 2936, 2852, 1722, 1673, 1481, 1341, 1245, 1031, 897, 800, 739 cm$^{-1}$; $^1$H NMR (400 MHz, CDCl$_3$) δ 1.06 (s, 3H, 18-CH$_3$), 1.16 (br. s, 3H, 19-CH$_3$), 2.04 (s, 3H, 3β-OCOCH$_3$), 3.88 (s, 3H, —OCH$_3$), 4.63 (m, 1H, 3α-H), 5.44 (d, J=5.6 Hz, 1H, 6-H), 6.98 (m, 1H, aromatic-H) 7.29 (m, 1H, aromatic-H), 7.30 (m, 1H, aromatic-H), 7.92 (s, 1H, 2'-H) and 9.61 (s, 1H, 16-CHO). About 0.11 g of mixture of 19a1 and 19a2 also collected (overall yield is 61%)

3β-Acetoxy-17-(1H-benzo[f]benzimidazol-1-yl)-16-formylandrosta-5,16-diene (20a)

Compound 20a prepared by following general method A, reacting 13 (0.38 g, 1 mmol) with 1H-benzo[f]benzimidazole (0.2 g, 1.2 mmol) in presence of K$_2$CO$_3$ (0.207 g, 1.5 mmol) in dry DMF (3 mL) at 80° C. for 2 h. Purification by FCC [petroleum ether/EtOAc/TEA (6:4:0.3)] gave 0.37 g (72%) of pure compound 20a: mp 158-160° C.; IR (CHCl$_3$) 3691, 3024, 2951, 2359, 1725, 1670, 1604, 1491, 1452, 1375, 1253, 1032, 897, 852, 818, 700, 657, 618, 576, 565, 550, 529, 511, 476 cm$^{-1}$; $^1$H NMR (500 MHz, CDCl$_3$) δ 1.05 (s, 6H, 18 and 19-CH$_3$), 2.04 (s, 3H, 3α-OCH$_3$), 4.62 (m, 1H, 3β-H), 5.44 (br, s, 6-H) 7.46 (br. s, 2H, aromatic-H), 7.94 (s, 2H, aromatic-H), 8.04 (m, 1H, aromatic-H), 8.15 (s, 1H, aromatic-H) 8.33 (s, 1H, 2'-H) and 9.71 (s, 1H, 16-CHO).

3β-Acetoxy-17-(6-Chloro-9H-purin-9-yl)-16-formylandrosta-5,16-diene (21a)

A mixture of 13 (2.43 g, 6.46 mmol), 6-chloropurine (0.5 g, 3.23 mmol) and TBAF (1.69 g, 6.46) in dry THF (40 mL) was stirred at 50° C. under Ar for 48 h. After cooling to room temperature, the reaction mixture concentrated and poured onto ice-cold water (250 mL) and the resulting precipitate was filtered, washed with water and dried to give a crude product. Purification by FCC [DCM/Methanol (9.7:0.3)] and then recrystallized with hot ethanol to give 0.82 g (51.3%) of pure 21a: mp 140-142° C.; IR (Neat) 2943, 2853, 1729, 1672, 1584, 1556, 1435, 1236, 1032, 939, cm-1; $^1$H NMR (500 MHz, CDCl$_3$) δ 1.07 (s, 3H, 18-CH$_3$), 1.09 (s, 3H, 19-CH$_3$), 2.04 (s, 3H, 3β-OCOCH$_3$), 4.61 (m, 1H, 3α-H), 5.43 (br, 1H, 6-H), 8.20 (s, 1H, 2'-H), 8.79 (s, 1H, aromatic-H), and 9.53 (s, 1H, 16-CHO).

3β-Acetoxy-17-(2-chloro-1H-benzimidazol-1-yl)-16-formylandrosta-5,16-diene (22a)

Compound 22a prepared by following general method A, reacting 13 (0.5 g, 1.33 mmol) with 2-chlorobenzimidazole (0.6 g, 4.0 mmol) in presence of K$_2$CO$_3$ (0.55 g, 4.0 mmol) in dry DMF (10 mL) at 80° C. for 50 h. After cooling to room temperature, the reaction mixture was poured onto ice-cold water (250 mL) and the resulting emulsion was extracted with DCM, organic layer dried and evaporated. Purification by FCC [petroleum ether/EtOAc (8:2)] gave 0.27 g (41.1%) of pure 22a: mp 203° C.; IR (Neat) 2936, 1731, 1679, 1448, 1244, 1033, 734 cm$^{-1}$; $^1$H NMR (500 MHz, CDCl$_3$) δ 1.06 (s, 3H, 18-CH$_3$), 1.16 (s, 3H, 19-CH$_3$), 2.04 (s, 3H, 3β-OCOCH$_3$), 4.62 (m, 1H, 3α-H), 5.43 (br, 1H, 6-H), 7.17 (d, 1H, J=7.9 Hz, aromatic-H), 7.34 (m, 2H, aromatic-Hs), 7.74 (d, 1H, J=7.4 Hz, aromatic-H) and 9.37 (s, 1H, 16-CHO).

General method B: Synthesis of 3β-Acetoxy-17-(1H-heteroaryl-1-yl)-androsta-5,16-diene (15, 16b-21b)

A solution of 3β-Acetoxy-17-(1H-heteroaryl-1-yl)-16-formylandrosta-5,16-diene (14, 17a-21a) in dry benzonitrile (10 mL) was refluxed in the presence of 10% Pd/C (50% weight of reactant) under Ar and monitored by TLC. After cooling to room temperature, the catalyst was removed by filtration through a Celite pad. The filtrate was evaporated, and the residue was purified by FCC on silica gel, using petroleum ether/EtOAc/TEA (7.5:3:0.5) solvent system. Above listed intermediate compounds were synthesized (using reactants, reagent and solvent ratio), isolated and purified by using this method unless otherwise stated.

3β-Acetoxy-17-(1H-benzimidazol-1-yl)-androsta-5,16-diene (15)

Compound 15 prepared by refluxing 14 (2.04 g, 4.45 mmol), with 10% Pd/C (1.0 g) in dry benzonitrile (10 mL) for 5 h. Followed by FCC purification provided pure 15 with identical spectral and analytical data as we previously reported.

3β-Acetoxy-17-(1H-indol-1-yl)-androsta-5,16-diene (16b)

Compound 16b prepared by following general method B, refluxing 16a (0.17 g, 0.36 mmol), with 10% Pd/C (0.085 g) in dry benzonitrile (3 mL) for 24 h, then about 0.030 g of Pd/C and solvent (1 mL) added and further refluxed for 12 h. Purification by FCC gave 0.12 g (77.5%) of pure 16b: mp 182-185° C.; IR (Neat) 2936, 2854, 1727, 1631, 1455, 1368, 1249, 1030, 721, cm$^{-1}$; $^1$H NMR (400 MHz, DMSO-d$_6$) δ 0.95 (s, 3H, 18-CH$_3$), 1.03 (s, 3H, 19-CH$_3$), 1.99 (s, 3H, 3β-OCOCH$_3$), 4.47 (m, 1H, 3α-H), 5.42 (br, 1H, 6-H), 5.88 (s, 1H, 16-H), 6.57 (m, 1H, 3'-H), 7.05 (m, 1H, 2'-H), 7.15 (m, 1H, aromatic-H), 7.37 (d, J=3.2 Hz, 1H, aromatic-H), 7.50 (d, J=8.0 Hz, 1H, aromatic-H), and 7.57 (d, J=7.7 Hz, 1H, aromatic-H).

3β-Acetoxy-17-(5,6-dimethyl-1H-benzimidazol-1-yl)-androsta-5,16-diene (17b)

Compound 17b prepared by following general method B, refluxing 17a (0.15 g, 0.308 mmol), with 10% Pd/C (0.075 g) in dry benzonitrile (2 mL) for 7 h. Purification by FCC gave 0.12 g (84.8%) of pure 17b: mp 159-162° C.; IR (Neat) 2926, 2852, 1729, 1626, 1491, 1462, 1369, 1236, 1030, 846, cm$^{-1}$; $^1$H NMR (400 MHz, CDCl$_3$) δ 1.03 (s, 3H, 18-CH$_3$), 1.09 (s, 3H, 19-CH$_3$), 2.06 (s, 3H, 3β-OCOCH$_3$), 2.40 (s, 6H, 2×aromatic-CH$_3$), 4.64 (m, 1H, 3α-H), 5.45 (br, 1H, 6-H), 5.96 (s, 1H, 16-H), 7.26 (s, 1H, aromatic-H), 7.58 (s, 1H, aromatic-H), and 7.87 (s, 1H, 2'-H).

3β-Acetoxy-17-(5(6)-nitrile-1H-benzimidazol-1-yl)-androsta-5,16-diene (18b)

Compound 18b prepared by following general method B, refluxing 18a (0.15 g, 0.31 mmol) 10% Pd/C (0.075 g) in dry benzonitrile (2 mL) for 24 h. Purification by FCC gave 0.09 g (63.5%) of pure 18b: mp 204-206° C.; IR (Neat) 2939, 2222, 1731, 1487, 1247, 1030, 822, cm$^{-1}$; $^1$H NMR (400 MHz, CDCl$_3$) δ 1.07 (s, 3H, 18-CH$_3$), 1.18 (s, 3H, 19-CH$_3$), 2.04 (s, 3H, 3β-OCOCH$_3$), 4.62 (m, 1H, 3α-H), 5.44 (m, 1H, 6-H), 6.03 (m, 1H, 16-H), 7.54-8.15 (m, 4H, aromatic-H).

3β-Acetoxy-17-(6-methoxy-1H-benzimidazol-1-yl)-androsta-5,16-diene (19b)

Compound 19b prepared by following general method B, refluxing 19a1 (0.15 g, 0.307 mmol), with 10% Pd/C (0.075 g) in dry benzonitrile (2 mL) for 72 h, then about 0.030 g of Pd/C added and further refluxed for 12 h. Purification by FCC gave 0.05 g (35%) of pure sticky compound 19b: IR (Neat) 2940, 1713, 1496, 1363, 1237, 1216, 1030, 816, cm$^{-1}$; $^1$H NMR (400 MHz, CDCl$_3$) δ 1.01 (s, 3H, 18-CH$_3$), 1.07 (s, 3H, 19-CH$_3$), 2.04 (s, 3H, 3β-OCOCH$_3$), 3.88 (s, 3H, —OCH$_3$), 4.63 (m, 1H, 3α-H), 5.44 (s, 1H, 6-H), 5.96 (br, 1H, 16-H), 6.92 (m, 2H, aromatic-Hs), 7.69 (d, 1H, J=8.7 Hz, aromatic-H), and 7.85 (s, 1H, 2'-H).

3β-Acetoxy-17-(1H-benzo[f]benzimidazol-1-yl)-androsta-5,16-diene (20b)

Compound 20b prepared by following general method B, refluxing 20a (0.2 g, 4.45 mmol), with 10% Pd/C (0.1 g) in dry benzonitrile (4 mL) for 5 h. Purification by FCC gave 0.14 g (73.8%) of pure 20b: mp 144-146° C.; IR (CHCl$_3$) 3687, 2947, 2854, 2358, 2340, 1725, 1633, 1609, 1557, 1489, 1454, 1373, 1291, 1253, 1195, 1136, 1031, 985, 910, 839, 735, 665, 590, 544, 533, 513, 502, 488 cm$^{-1}$; 1H NMR (500 MHz, CDCl$_3$) δ 1.08 (s, 3H, 18-CH$_3$), 1.10 (s, 3H, 19-CH$_3$), 2.01 (s, 3H, 3β-OCH$_3$), 4.62 (m, 1H, 3α-H), 5.45 (br, s, 6-H), 6.11 (s, 1H, 16-H), 7.42 (m, 2H, aromatic-Hs), 7.92 (m, 2H, aromatic-H), 8.04 (m, 1H, aromatic-H), 8.15 (s, 1H, aromatic-H) and 8.29 (s, 1H, 2'-H).

3β-Acetoxy-17-(6-Chloro-9H-purin-9-yl)-androsta-5,16-diene (21b)

Compound 21b prepared by following general method B, refluxing 21a (0.4 g, 0.81 mmol), with 10% Pd/C (0.4 g, i.e., equal weight of 21a) in dry benzonitrile (7.5 mL) for 4 h. Cooled to room temperature, the catalyst was removed by filtration through a Celite pad. The filtrate was evaporated, and carried to next step without purification.

3β-Acetoxy-17-(2-chloro-1H-benzimidazol-1-yl)-androsta-5,16-diene (22b)

A solution of 3β-Acetoxy-17-(2-chlorobenzimidazol-1-yl)-16-formylandrosta-5,16-diene (22a), (0.15 g, 0.304 mmol) in dry toluene (3 mL) was refluxed in the presence of chlorotris (triphenylphosphine) rhodium (I) (0.29 g, 0.311 mmol) for 60 h. After cooling to room temperature, the catalyst was removed by filtration through a Celite pad. The filtrate was evaporated, and the residue was purified by FCC [petroleum ether/EtOAc (8:2)] to give 0.04 g (28%) of pure 22b: mp 161-165° C.; IR (Neat) 2926, 2853, 1629, 1403, 1462, 1369, 1233, 1035, 847 cm$^{-1}$; $^1$H NMR (500 MHz, CDCl$_3$) δ 1.05 (d, 6H, 18 and 19-CH$_3$), 2.04 (s, 3H, 3β-OCOCH$_3$), 4.62 (m, 1H, 3α-H), 5.44 (m, 1H, 6-H), 6.06 (s, 1H, 16-H), 7.33 (m, 1H, aromatic-H), 7.52 (m, 1H, aromatic-H), and 7.68 (m, 2H, aromatic-H).

General method C: Synthesis of 3β-Hydroxy-17-(1H-heteroaryl-1-yl)-androsta-5,16-diene (5, 16-22) and 3β-Hydroxy-17-(1H-benzimidazol-1-yl)-16-((alkyl/arylamino)methyl)-androsta-5,16-diene (25, 28 and 31)

The acetate (15, 16b-22b, 24, 27, 30) (1 g) was dissolved in methanol (15 mL) under an inert Ar atmosphere, and the resulting solution was treated with 10% methanolic KOH (5 mL). The mixture was stirred at room temperature, monitored by TLC. Reaction mixture concentrated under vacuum, ice water (100 mL) added, and the resulting white precipitate was filtered, washed with water and dried. FCC on a short silica gel column, eluting with petroleum ether/EtOAc (6:4) to obtain pure target compounds. Above listed final compounds were synthesized (using reactants, reagent and solvent ratio), isolated and purified by using this method unless otherwise stated.

3β-Hydroxy-17-(1H-benzimidazol-1-yl)-androsta-5,16-diene (5)[24]

Compound 5 prepared by following general method C, treating acetate solution of 15 (1 g 3.02 mmol) in methanol (15 mL) with 10% methanolic KOH (5 mL) for 1.5 h. Purification by FCC over short column provided pure 5 with identical spectral and analytical data as we previously reported.

3β-Hydroxy-17-(1H-indol-1-yl)-androsta-5,16-diene (16)

Compound 16 prepared by slightly modifying general method C. The acetate solution of 16b (0.09 g 0.2 mmol) in methanol (1.5 mL) was refluxed with 10% methanolic KOH (1 mL) for 3 h. Purification by FCC over short column short column gave pure 16 (0.076 g, 98.7%), mp 142-145° C.; IR (Neat) 3305, 2931, 2836, 1625, 1455, 1327, 1225, 10598, 1042, 740 cm$^{-1}$; $^1$H NMR (500 MHz, CDCl$_3$) δ 1.00 (s, 3H, 18-CH$_3$), 1.06 (s, 3H, 19-CH$_3$), 3.54 (m, 1H, 3α-H), 5.41 (br, 1H, 6-H), 5.85 (s, 1H, 16-H), 6.55 (m, 1H, 3'-H), 7.11 (m, 1H, 2'-H), 7.19 (dd, J=8.4, 5.7 Hz, 2H, aromatic-Hs), 7.51 (d, 1H, J=8.3 Hz, aromatic-H), and 7.60 (d, 1H, J=7.8 Hz, aromatic-H); $^{13}$C NMR (500 MHz, CDCl$_3$) δ 149.6, 141.2, 137.2, 128.4, 126.9, 122.0, 121.7, 120.6, 119.6, 111.3, 102.4, 71.7, 55.9, 50.6, 47.3, 42.0, 37.2, 36.8, 35.1, 31.6, 30.2, 20.8, 19.4, 16.0; HRMS calcd 410.2454 (C$_{27}$H$_{33}$ON.Na$^+$), found 410.2460.

3β-Hydroxy-17-(5,6-dimethyl-1H-benzimidazol-1-yl)-androsta-5,16-diene (17)

Compound 17 prepared by following general method C by treating acetate solution of 17b (0.1 g 0.22 mmol) in methanol (2 mL) with 10% methanolic KOH (1 mL) for 3 h. Purification by FCC over short column provided pure 17 (0.05 g, 55%), mp 194-196° C.; IR (Neat) 3262, 2925, 2896, 2848, 1628, 1493, 1481, 1371, 1058, 834, cm$^{-1}$; $^1$H NMR (500 MHz, CDCl$_3$) δ 1.02 (s, 3H, 18-CH$_3$), 1.06 (s, 3H, 19-CH$_3$), 2.38 (s, 6H, 2×aromatic-CH$_3$), 3.55 (m, 1H, 3α-H), 5.41 (m, 1H, 6-H), 5.95 (t, J=2.6 Hz, 16-H), 7.25 (s, 1H, aromatic-H), 7.57 (s, 1H, aromatic-H), and 7.87 (s, 1H, 2'-H); $^{13}$C NMR (500 MHz, CDCl$_3$) δ 147.3, 141.3, 132.7, 131.6, 123.4, 121.1, 119.9, 111.3, 71.6, 55.9, 50.5, 47.2, 42.3, 37.2, 34.9, 31.6, 30.37, 20.6, 19.3, 16.0; HRMS calcd 439.2719 (C$_{28}$H$_{36}$ON$_2$.Na$^+$), found 439.2726.

3β-Hydroxy-17-(5(6)-nitrile-1H-benzimidazol-1-yl)-androsta-5,16-diene (18)

Compound 18 prepared according to general method C by treating acetate solution of 18b (0.075 g 0.165 mmol) in methanol (1.5 mL) with 10% methanolic KOH (1 mL) for 2 h. Purification by FCC over short column provided pure 18 (0.055 g, 80.8%), mp 192-193° C.; IR (Neat) 3409, 3285, 2928, 2226, 1654, 1614, 1469, 1229, 1059, 801, cm$^{-1}$; $^1$H NMR (500 MHz, CDCl$_3$) δ 1.01 (d, 3H, 18-CH$_3$), 1.06 (d, 3H, 19-CH$_3$), 3.55 (tdq, J=9.0, 4.7, 2.6 Hz, 1H, 3α-H), 5.40 (dp, J=4.8, 1.7 Hz, 6-H), 6.02 (m, 1H, 16-H), 7.52-8.15 (m, 4H, aromatic-H); $^{13}$C NMR (500 MHz, CDCl$_3$) δ 146.7, 144.8, 141.5, 127.0, 126.4, 125.5, 121.5, 119.8, 116.4, 112.4, 106.8, 106.1, 71.7, 56.1, 50.6, 47.5, 42.4, 37.3, 36.9, 34.9, 31.7, 30.6, 20.8, 19.5, 16.2, 15.0; HRMS calcd 414.2539 (C$_{27}$H$_{31}$ON$_3$.H$^+$), found 414.2532.

3β-Hydroxy-17-(6-methoxy-1H-benzimidazol-1-yl)-androsta-5,16-diene (19)

Compound 19 prepared according to general method C by treating acetate solution of 19b (0.05 g 0.11 mmol) in methanol (1 mL) with 10% methanolic KOH (1 mL) for 3 h. Purification by FCC over short column provided pure 19 (0.03 g, 55%), mp 169-179° C.; IR (Neat) 3339, 2933, 1614, 1501, 1450, 1283, 1068, 906, 813, 728 cm$^{-1}$; $^1$H NMR (400 MHz, CDCl$_3$) δ 1.01 (s, 3H, 18-CH$_3$), 1.06 (s, 3H, 19-CH$_3$), 3.58 (m, 1H, 3α-H), 3.86 (s, 3H, —OCH$_3$), 5.41 (t, 1H, J=2.42 Hz, 6-H), 5.95 (t, 1H, J=1.48 Hz, 16-H), 6.92 (m, 2H, aromatic-H), 7.67 (m, 1H, aromatic-H), and 7.58 (s, 1H, 2'-H); $^{13}$C NMR (500 MHz, CDCl$_3$) δ 157.32, 147.6, 141.5, 137.9, 135.4, 124.0, 121.2, 120.7, 111.6, 95.2, 71.7, 56.2, 50.7, 47.5, 42.5, 37.4, 35.1, 31.8, 30.6, 20.9, 19.5, 16.2; HRMS calcd 441.2512 (C$_{27}$H$_{34}$O$_2$N$_2$.Na$^+$), found 441.2507.

3β-Hydroxy-17-(1H-benzo[f]benzimidazol-1-yl)-androsta-5,16-diene (20)

Compound 20 prepared according to general method C by treating acetate solution of 20b (0.1 g, 0.32 mmol) in methanol (5 mL) with 10% methanolic KOH (1 mL) for 1.5 h. Purification by crystallization from EtOAc/Methanol gave 20 (0.075 g, 74%), mp 150-152° C.; IR (CHCl$_3$) 2934, 2339, 1609, 1490, 1453, 1291, 1040, 837, 808, 705, 663, 608, 578, 550, 517 cm$^{-1}$; $^1$H NMR (500 MHz, CDCl$_3$) δ 1.09 (s, 6H, 18 and 19-CH$_3$), 3.57 (m, 1H, 3α-H), 5.44 (br, s, 6-H), 6.13 (s, 1H, 16-H), 7.44 (m, 2H, aromatic-Hs), 7.94 (m, 2H, aromatic-H), 8.03 (m, 1H, aromatic-H), 8.18 (s, 1H, aromatic-H) and 8.31 (s, 1H, 2'-H). HRMS calcd 461.2563 (C$_{30}$H$_{34}$N$_2$O.Na+), found 461.2570.

3β-Hydroxy-17-(6-Chloro-9H-purin-9-yl)-androsta-5,16-diene (21)

Compound 21 prepared according to general method C by treating acetate solution of 21b (0.04 g 0.085 mmol) in methanol (1 mL) with 10% methanolic KOH (1 mL) for 3 h. Purification by FCC over short column [DCM/methanol/TEA (9.7:0.3:0.05)] to obtain pure 21 (0.03 g, 82.6%), mp 272-274° C.; IR (Neat) 3385, 2928, 2604, 2498, 1664, 1516, 1433, 1346, 1040, 805, cm$^{-1}$; $^1$H NMR (500 MHz, CDCl$_3$) δ 1.12 (s, 3H, 18-CH$_3$), 1.23 (s, 3H, 19-CH$_3$), 3.50 (m, 1H, 3α-H), 5.41 (br, 1H, 6-H), 5.59 (s, 1H, 16-H), 8.11 (s, 1H, 2'-H), 8.40 (s, 1H, aromatic-H); $^{13}$C NMR (500 MHz, CDCl$_3$) δ 164.1, 153.4, 141.6, 139.4, 121.9, 120.8, 71.2, 56.3, 53.1, 50.1, 47.0, 46.0, 36.9, 31.2, 19.5, 15.0, 11.7, 8.9, 8.8; HRMS calcd 871.3952 (C$_{24}$H$_{29}$ClON$_4$)$_2$.Na$^+$. found 871.3972

3β-Hydroxy-17-(2-chloro-1H-benzimidazol-1-yl)-androsta-5,16-diene (22)

Compound 22 prepared according to general method C by treating acetate solution of 22b (0.03 g 0.064 mmol) in methanol (0.75 mL) with 10% methanolic KOH (1 mL) for 3 h. Purification by FCC over short column [petroleum ether/EtOAc (7:3)] to obtain pure 22 (0.025 g, 91.6%), mp 83-86° C.; IR (Neat) 3346, 2929, 1449, 1267, 1121, 1071, 1040, 742 cm$^{-1}$; $^1$H NMR (500 MHz, CDCl$_3$) δ 1.05 (br, 6H, 18 and 19-CH$_3$), 3.54 (m, 1H, 3α-H), 5.41 (br, 1H, 6-H), 6.04 (m, 1H, 16-H), 7.25 (m, 1H, aromatic-H), 7.31 (m, 1H, aromatic-H), and 7.68 (m, 2H, aromatic-H); $^{13}$C NMR (500 MHz, CDCl$_3$) δ 141.5, 133.2, 129.9, 123.3, 121.2, 111.5, 71.9, 55.9, 50.8, 42.5, 38.9, 37.3, 37.0, 34.0, 31.8, 30.6, 24.0, 23.2, 20.73, 19.5, 17.3, 16.4; HRMS calcd 445.2017 (C$_{28}$H$_{36}$ON$_2$.Na$^+$), found 445.2020.

General method D: Synthesis of 3β-Acetoxy-17-(1H-benzimidazol-1-yl)-16-((alkyl/arylimino)methyl)-androsta-5,16-diene (23, 26 and 29)

The title compounds were prepared by refluxing a solution of 3β-Acetoxy-17-(1H-benzimidazol-1-yl)-16-formylandrosta-5,16-diene (14) (1 equivalent), corresponding primary amine (2 equivalent), molecular sieves (~25% weight of 14) and ethanol under Ar for 3-12 h. Reaction mixture was filtered, concentrated under vacuum, residue stirred with water and resulting crude product filtered. Purification by the FCC on silica gel column [petroleum ether/EtOAc (1:1)] gave the desired pure compounds. Above listed compounds were synthesized (using reactants, reagent and solvent ratio), isolated and purified by using this method unless otherwise stated.

3β-Acetoxy-17-(1H-benzimidazol-1-yl)-16-((EZ)-(isopentylimino)methyl)-androsta-5,16-diene (23)

Compound 23 prepared by following general method D, refluxing 14 (0.4 g, 0.87 mmol), isopentylamine (0.15 g, 1.7 mmol), molecular sieves (0.2 g) in ethanol (5 mL) for 3 hours. Followed purification by FCC gave 0.41 g (89%) 23: mp sinters at 135° C., melts at 145° C.; IR (Neat) 2934, 2851, 1726, 1676, 1640, 1490, 1453, 1247, 1219, 1032, 744 cm$^{-1}$; $^1$H NMR (400 MHz, CDCl$_3$) δ 0.87 (d, 6H, aliphatic-CH$_3$), 1.07 (s, 3H, 18-CH$_3$), 1.16 (s, 3H, 19-CH$_3$), 2.06 (s, 3H, 3β-OCOCH$_3$), 4.64 (m, 1H, 3α-H), 5.46 (br. s, 1H, 6-H), 7.30 (s, 1H, imine-CH), 7.34 (m, 2H, aromatic-Hs), 7.72 (s, 1H, aromatic-H), 7.87 (s, 1H, aromatic-H), and 7.94 (s, 1H, 2'-H).

General method E: Synthesis of 3β-Acetoxy-17-(1H-benzimidazol-1-yl)-16-((alkyl/arylamino)methyl)-androsta-5,16-diene (24, 27 and 30)

To ice cold solution of 16-enamines (23/26/30) (1 mole equivalent) in methanol added NaBH$_4$ (0.5 mole equivalent) in three portions over 30 minutes. Reaction continued for 1.5-5 h then neutralized with acetic acid, evaporated, residue treated with water and filtered. Crude product carried to next step without purification.

3β-Acetoxy-17-(1H-benzimidazol-1-yl)-16-((isopentylamino)methyl)-androsta-5,16-diene (24)

Compound 24 prepared by following general method E, reacting 23 (0.1 g, 0.2 mmol) in methanol (1.5 mL) with NaBH$_4$ (0.0035 g, 0.09 mmol) at ° C. for 1.5 h. The crude product 24 (0.09 g, 89%) was carried to next step without purification.

3β-Hydroxy-17-(1H-benzimidazol-1-yl)-16-((isopentylamino)methyl)-androsta-5,16-diene (25)

Compound 25 prepared by following general method C, treating methanolic solution (1 mL) of crude acetate 24 (0.08 g 0.15 mmol) with 10% methanolic KOH (0.75 mL) for 3 h. Followed purification by passing through short silica bed [DCM/ethanol (9.5:0.5)] to give 25 (0.065 g, 88%), mp 111-113° C.; IR (Neat) 3281, 2927, 2850, 1487, 1454, 1374, 1224, 1061, 1007, 765, cm$^{-1}$; $^1$H NMR (500 MHz, CDCl$_3$) δ 0.81 (d, 6H, alphatic-CH$_3$), 1.04 (s, 6H, 18, 19-CH$_3$), 3.55 (m, 1H, 3α-H), 5.41 (br, 1H, 6-H), 7.19-7.43 (m, 3H, aromatic-Hs), 7.75-7.82 (m, 1H, aromatic-H), and 8.1 (s, 1H, 2'-H); $^{13}$C NMR (500 MHz, CDCl$_3$) δ 142.8, 140.0, 134.8, 123.4, 122.4, 120.2, 110.8, 71.5, 55.9, 50.7, 48.9, 42.3, 38.9, 36.8, 34.6-32.4, 31.6, 30.3, 26.0, 22.6, 20.5, 19.3, 16.0, 15.8; HRMS calcd 510.3454 (C$_{32}$H$_{45}$ON$_3$.Na$^+$), found 510.34509

3β-Acetoxy-17-(1H-benzimidazol-1-yl)-16-((EZ)-(phenylimino)methyl)-androsta-5,16-diene (26)

Compound 26 prepared by following synthetic method D, refluxing 14 (0.15 g, 0.33 mmol), aniline (0.06 g, 0.65 mmol), molecular sieves (0.04 g) in ethanol (2 mL) for 3 h. Purification by passing through a silica bed gave 0.15 g (85.9%) 26: mp sinters at 85-90° C., melts at 125° C.; IR (Neat) 2973, 2932, 2822, 1727, 1635, 1589, 1486, 1453, 1239, 1219, 1029, 764 cm$^{-1}$; $^1$H NMR (400 MHz, CDCl$_3$) δ 1.10 (s, 3H, 18-CH$_3$) 1.23 (s, 3H, 19-CH$_3$), 2.06 (s, 3H, 3β-OCOCH$_3$), 4.65 (m, 1H, 3α-H), 5.49 (br, 1H, 6-H), 6.96 (m, 2H, aromatic-Hs) 7.17 (m, 1H, aromatic-H) 7.26 (s, 1H, imine-CH), 7.35 (m, 4H, aromatic-Hs), 7.87 (m, 1H, aromatic-H), 7.94 (m, 1H, aromatic-H) and 7.99 (s, 1H, 2'-H).

3β-Acetoxy-17-(1H-benzimidazol-1-yl)-16-((phenylamino)methyl)-androsta-5,16-diene (27)

Compound 27 prepared by following General synthetic method E, reacting 26 (0.1 g, 0.19 mmol) in methanol (1.5 mL) with NaBH$_4$ (0.0035 g, 0.09 mmol) at ° C. for 1.5 h. The crude 27 carried to next step without purification.

3β-Hydroxy-17-(1H-benzimidazol-1-yl)-16-((phenylamino)methyl)-androsta-5,16-diene (28)

Compound 28 prepared by following General method C, treating methanolic solution (1 mL) of crude acetate 27 with 10% methanolic KOH (0.75 mL) for 3 h. Followed purification by passing through short silica bed [DCM/ethanol (9.5:0.5)] gave 28 (0.08 g, 86%), mp 130-132° C.; IR (Neat) 3329, 2928, 2852, 1602, 1418, 1375, 1217, 1058, 1007, 833, cm$^{-1}$; $^1$H NMR (500 MHz, CDCl$_3$) δ 1.03 (s, 3H, 18-CH$_3$), 1.04 (s, 3H, 19-CH$_3$), 3.54 (m, 1H, 3α-H), 3.65 (br. s, 2H, —CH$_2$), 5.38 (t, 1H, J=2.62 Hz, 6-H), 6.40 (t, 2H, J=8.8 Hz, aromatic-Hs), 6.69 (d, 1H, J=7.3 Hz, aromatic-H), 7.08 (m, 2H, aromatic-Hs), 7.20-7.33 (m, 3H, aromatic-Hs), 7.74-7.84 (m, 1H, aromatic-H), and 7.79 (s, 1H, 2'-H); $^{13}$C NMR (500 MHz, CDCl$_3$) δ 147.6, 141.3, 138.7, 123.7, 122.5, 129.9, 120.4, 118.0, 113.0, 110.8, 71.6, 54.7, 50.6, 48.0, 42.2, 36.8, 34.4, 32.4, 31.1, 30.3, 20.5, 19.3, 15.8. HRMS calcd 516.2985 (C$_{33}$H$_{39}$ON$_3$.Na$^+$), found 516.2981

3β-Acetoxy-17-(1H-benzimidazol-1-yl)-16-((EZ)-((3,4-dimethoxyphenyl)imino)methyl)-androsta-5,16-diene (29)

Compound 29 prepared by following general method D, refluxing 14 (0.3 g, 0.65 mmol), 3,4-dimethoxy aniline (0.2 g, 1.3 mmol), molecular sieves (0.075 g) in ethanol (2 mL) for overnight. Purification by FCC [petroleum ether/EtOAc (1:1)] gave 0.29 g (74.5%) 29: mp sinters at 115° C., melts at 130° C.; IR (Neat) 2937, 2904, 2852, 1729, 1586, 1509, 1451, 1372, 1233, 1125, 1026, 765 cm$^{-1}$; $^1$H NMR (400 MHz, CDCl$_3$) δ 1.10 (s, 3H, 18-CH$_3$) 1.23 (s, 3H, 19-CH$_3$), 2.06 (s, 3H, 3β-OCOCH$_3$), 3.84 (m, 6H, 2×OCH$_3$), 4.64 (m, 1H, 3α-H), 5.48 (br. s, 1H, 6-H), 6.56 (m, 2H, aromatic-Hs) 6.73 (m, 1H, aromatic-H) 7.36 (m, 3H, aromatic-2Hs and imine-CH), 7.88 (m, 1H, aromatic-H), 7.95 (m, 1H, aromatic-H), and 8.00 (s, 1H, 2$^1$-H).

3β-Acetoxy-17-(1H-benzimidazol-1-yl)-16-(((3,4-dimethoxyphenyl)amino)methyl)-androsta-5,16-diene (30)

Compound 30 prepared by following General synthetic method E, reacting 29 (0.15 g, 0.25 mmol) in methanol (2.5 mL) with NaBH$_4$ (0.05 g, 0.126 mmol) at ° C. for 5 h. The crude 30 carried to next step without purification.

3β-Hydroxy-17-(1H-benzimidazol-1-yl)-16-(((3,4-dimethoxyphenyl)amino)methyl)-androsta-5,16-diene (31)

Compound 31 prepared by following method C, treating methanolic solution of (2 mL) of crude acetate 30 with 10% methanolic KOH (0.75 mL). Subsequent purification by FCC [DCM/ethanol (9.7:0.3)] to give 31 (0.11 g, 79.6%), mp sinters at 120° C. melts 135° C.; IR (Neat) 3351, 2929, 2852, 1612, 1514, 1454, 1229, 1136, 1025, 765, cm$^{-1}$; $^1$H NMR (500 MHz, CDCl$_3$) δ 1.03 (s, 3H, 18-CH$_3$), 1.09 (s, 3H, 19-CH$_3$), 3.53 (m, 1H, 3α-H), 3.61 (br, 2H, N—CH$_2$), 3.74-3.77 (s, 6H, 2×OCH$_3$), 5.37 (br, 1H, 6-H), 5.95 (br, 1H, aromatic-1"-H), 6.04 (d, J=2.6 Hz, 1H, aromatic-5"-H), 6.64 (br, 1H, aromatic-6"-H), 7.21-7.31 (m, 3H, aromatic-Hs), 7.74-7.83 (m, 1H, aromatic-H), and 7.79 (s, 1H, 2'-H); $^{13}$C NMR (500 MHz, CDCl$_3$) δ 149.9, 142.2, 138.8, 123.7, 122.5, 120.9, 112.9, 110.3, 103.8, 99.4, 71.5, 56.6, 55.7, 50.6. 48.3, 42.8, 4.1, 34.7, 32.2, 31.1, 30.0, 20.5, 19.3, 15.8. HRMS calcd 576.3196 (C$_{35}$H$_{43}$O$_3$N$_3$.Na$^+$), found 576.3188.

17-(1H-Benzimidazol-1-yl)-androsta-4,16-dien-3-one (32)

This compound prepared from 5 as previously described, provided spectral and analytical data as reported.[24] $^{13}$C NMR (500 MHz, CDCl$_3$) δ 199.4, 170.5, 147.2, 143.5, 141.1, 134.7, 124.3, 124.3, 123.5, 122.6, 122.5, 111.3, 54.3, 54.2, 47.4, 38.9, 35.9, 35.8, 34.1, 33.8, 32.8, 31.4, 30.4, 17.5, 17.3, 16.3.

17-(1H-Benzimidazol-1-yl)-androsta-5,16-dien-3-one (33)

To a ice cold solution of 5 (0.05 g, 0.13 mmol) in dry DCM (3 mL) was added Dess-Martin periodinane (0.11 g, 0.26 mmol) and the mixture was stirred at ice cold temperature for 5 h. Then it was diluted with ether and was quenched with a mixture of saturated aqueous NaHCO$_3$/Na$_2$S$_2$O$_3$ (1:3). The organic layer was washed with brine and dried over Na$_2$SO$_4$, then solvent was evaporated under vacuum and the crude product was purified by FCC [DCM/ethanol/TEA (30:1:0.05)] to give the title compound 33 (0.035 g, 70%): mp 170-172° C.; IR (Neat) 2941, 1711, 1491, 1451, 1226, 751 cm$^{-1}$; $^1$H NMR (500 MHz, CDCl$_3$) δ 1.05 (s, 3H, 18-CH$_3$), 1.24 (s, 3H, 19-CH$_3$), 5.41 (t, 1H, J=2.5 Hz, 6-H), 5.99 (br, 1H, 16-H), 7.30 (m, 2H, aromatic-Hs), 7.49 (d, J=6.9 Hz, 1H, aromatic-H), 7.81 (m, 1H, aromatic-H), and 7.96 (s, 1H, 2'-H); $^{13}$C NMR (500 MHz, CDCl$_3$) δ 209.9, 147.3, 143.5, 139.2, 134.8, 124.3, 123.5, 122.8, 122.6, 122.0, 120.5, 111.3, 56.0, 49.9, 49.7, 47.5, 37.74, 37.4, 37.0, 31.3, 31.1, 30.4, 19.3, 19.2, 16.8, 16.2. HRMS calcd 409.2250 (C$_{26}$H$_{30}$ON$_2$.Na$^+$), found 409.2258.

3β-Mesyloxy-17-(1H-benzimidazol-1-yl)-androsta-5,16-dien (34)

To ice cold solution of 5 (0.4 g, 1.03 mmol) in pyridine (5 ml), was added methanesulfonyl chloride (0.68 g, 6 mmol). Reaction mixture stirred at 0° C. for 5 h, then room temperature for 8 h and quenched to 75 ml ice-water mixture. The resulting yellow solid was, filtered, washed, dried and the crude product was purified by FCC [DCM/ethanol (1.5%)] to give the title compound 34 (0.4 g, 83%), mp 177-179° C. (lit.[15] 149-150° C.); IR (Neat) 2944, 1486, 1452, 1326, 1170, 938, 765 cm$^{-1}$; $^1$H NMR (500 MHz, CDCl$_3$) δ 1.03 (s, 3H, 18-CH$_3$), 1.09 (s, 3H, 19-CH$_3$), 3.03 (s, 3H, mesyl-Hs), 4.56 (m, 1H, 3α-H), 5.49 (br, 1H, 6-H), 6.0 (m, 1H, 16-H), 7.30 (m, 2H, aromatic-Hs), 7.49 (m, 1H, aromatic-H), 7.82 (m, 1H, aromatic-H), and 7.97 (s, 1H, 2'-H); $^{13}$C NMR (500 MHz, CDCl$_3$) δ 147.1, 143.3, 141.6, 139.1, 134.6, 123.4, 120.2, 81.6, 55.7, 50.3, 47.2, 39.2, 36.8, 34.8, 31.1, 28.9, 20.6, 19.1, 16.0. HRMS calcd 955.4472 (C$_{26}$H$_{30}$ON$_2$)$_2$Na$^+$. found 955.4468.

3β-Tosyloxy-17-(1H-benzimidazol-1-yl)-androsta-5,16-dien (35)

To a cold (0° C.) solution of 5 (0.1 g, 0.26 mmol) in pyridine (3 ml), was added tosyl chloride (0.06 g, 0.31 mmol). Reaction mixture stirred at 0° C. for 5 h, then room temperature for 3 h and quenched to 30 ml ice-water mixture. The resulting yellow solid was filtered, washed, dried and the crude product was purified by FCC [DCM/Ethanol (1.0%)]. Resulting sticky solid was dissolved in 1.5 ml of EtOAc and about 10 ml of petroleum ether added slowly with stirring, the resulting turbid solution stirred at room temperature for 30 min, to give free flowing solid of title compound 35 (0.115 g, 84.5%), mp 139-141° C.; IR (Neat) 2948, 2850, 1490, 1451, 1329, 1171, 917, 740 cm$^{-1}$; $^1$H NMR (500 MHz, CDCl$_3$) δ 0.99 (s, 3H, 18-CH$_3$), 1.01 (s, 3H, 19-CH$_3$), 2.44 (s, 3H, 4"-CH$_3$), 4.35 (m, 1H, 3α-H), 5.37 (m, 1H, 6-H), 5.97 (m, 1H, 16-H), 7.25-7.34 (m, 3H, aromatic-Hs), 7.35-7.37 (m, 2H, 2", 6"-Hs), 7.48 (m, 1H, aromatic-H), 7.79 (m, 3H, aromatic-H and 3", 5"-H), and 7.95 (s, 1H, 2'-H); $^{13}$C NMR (500 MHz, CDCl$_3$) δ 147.0, 144.5, 141.6, 139.3, 134.6, 129.8, 127.6, 123.5, 122.5, 120.6, 111.1, 82.1, 55.7, 50.3, 47.2, 38.9, 36.8, 34.8, 30.3, 28.5, 21.7, 20.57, 19.1. HRMS calcd 565.2495 (C$_{33}$H$_{38}$O3N$_2$S.Na$^+$), found 565.2506.

General method F: Synthesis of 3-(Substituted-oximino)-17-(1H-Benzimidazol-1-yl)-androsta-4,16-diene (36-39)

To a refluxing solution of ketone 32 (1 mole equivalent) in ethanol-methanol (2:1) solvent mixture, add a solution of sodium acetate (9.4 mole equivalent), corresponding substituted-oxamine hydrochloride (10.5 mole equivalent) in distilled water (10 mole equivalent). Reflux continued for 2-3 h, then concentrated, residue treated with water and crude product filtered. Purification FCC over silica using 5% ethanolic DCM gave pure oximes.

3-((EZ)-Hydroximino)-17-(1H-Benzimidazol-1-yl)-androsta-4,16-diene (36)

Compound 36 prepared by following general method F. To a refluxing solution of 32 (0.08 g, 0.194 mmol) in ethanol-methanol (2 mL) added a solution of sodium acetate (0.15 g, 1.83 mmol), hydroxylamine .HCl (0.07 g, 2.04 mmol) in 0.75 ml distilled water. The reflux continued for 2 h and subsequent purification by FCC gave compound (mixture of EZ isomers) 36 (0.06 g, 77%): mp sinters at 145° C., melts 155-160° C.; IR (Neat) 3181, 2929, 2853, 1609, 1453, 1226, 847 cm$^{-1}$; $^1$H NMR (500 MHz, CDCl$_3$) δ 1.02 (s, 3H, 18-CH$_3$), 1.11-1.15 (s, 3H, 19-CH$_3$), 5.81 and 6.52 (~57% and 33% for E and Z isomers respectively) of (s, 1H, 4-H), 5.95 (br, 1H, 16-H), 7.30 (m, 2H, aromatic-Hs), 7.47 (m, 1H, aromatic-H), 7.81 (m, 1H, aromatic-H), and 7.95 (s, 1H, 2'-H); $^{13}$C NMR (500 MHz, CDCl$_3$) δ 158.64, 156.6, 154.5, 147.0, 142.9, 134.5, 124.3, 122.6, 117.8, 111.2, 55.3, 54.2, 47.3, 38.1, 34.6, 32.8, 30.3, 24.6, 20.9, 18.7, 17.9, 16.1. HRMS calcd 424.2359 (C$_{26}$H$_{31}$ON$_3$.Na$^+$), found 424.2363.

Separation of E and Z Isomers of 36:

Initially EZ mixture was purified by FCC using petroleum ether and EtOAc (1:1) mixture. This provided better purity of individual isomers with slight contamination of each in one another. The major product 36E was further purified by crystallization with hot EtOAc which resulted into pure single isomer 36E: mp 218-221° C.; $^1$H NMR (400 MHz, CDCl$_3$) δ ppm 1.02 (s, 3H, 18-CH$_3$), 1.11 (s, 3H, 19-CH$_3$), 5.85 (s, 1H, 4-H), 5.98 (s, 1H, 16-H), 7.28-7.36 (m, 2H, aromatic-Hs), 7.44-7.55 (m, 1H, aromatic-H), 7.79-7.88 (m, 1H, aromatic-H), 7.97 (s, 1H, 2'-H), 9.04 (br. s., 1H, —OH); $^{13}$C NMR (101 MHz, CDCl$_3$) δ ppm 156.7, 154.4, 147.1, 143.1, 141.6, 134.5, 124.1, 123.5, 122.5, 120.2, 117.9, 111.1, 55.3, 54.0, 47.3, 38.1, 34.8, 34.6, 34.2, 32.2, 31.5, 30.2, 21.1, 18.7, 17.6, 16.1. Where, 36Z was further purified by preparative TLC using petroleum-ether, EtOAc (1:1) as solvent system: mp 158-162° C.; $^1$H NMR (400 MHz, CDCl$_3$) δ ppm 1.02 (s, 3H, 18-CH$_3$), 1.15 (s, 3H, 19-CH$_3$), 5.97 (br s., 1H, 16-H), 6.53 (s, 1H, 4-H), 7.27-7.34 (m, 2H, aromatic-Hs), 7.44-7.52 (m, 1H, aromatic-H), 7.76-7.87 (m, 1H, aromatic-H), 7.7 (s, 1H, 2'-H), 8.87 (br. s., 1H, —OH); $^{13}$C NMR (101 MHz, CDCl$_3$) δ ppm 158.5, 147.0, 143.1, 141.6, 134.5, 124.2, 123.5, 122.6, 120.2, 117.7, 111.1, 55.2, 54.2, 47.3, 39.0, 38.1, 36.1, 34.8, 34.2, 32.8, 31.8, 30.2, 24.7, 20.9, 17.9, 16.1.

3-((EZ)—O-Phenyloxime)-17-(1H-Benzimidazol-1-yl)-androsta-4,16-diene (37)

Compound 37 prepared by following general method F. To a refluxing solution of 32 (0.05 g, 0.13 mmol) in ethanol-methanol (2 ml) added a solution of sodium acetate (0.1 g, 1.22 mmol), phenoxamine .HCl (0.2 g, 1.35 mmol) in 0.5 ml distilled water. The reflux continued for 2 h and subsequent purification by FCC gave compound (mixture of EZ isomers) 37 (0.04 g, 64%): mp 96-98° C.; IR (Neat) 2935, 2854, 1627, 1590, 1487, 1216, 897 cm$^{-1}$; $^1$H NMR (500 MHz, CDCl$_3$) δ 1.05 (s, 3H, 18-CH$_3$), 1.16-1.20 (s, 3H, 19-CH$_3$), 6.00 (s, 1H, 4-H and 16-H), 6.00 and 6.67 (~55% and 45% for E and Z isomers respectively) (s, 1H, 4-H), 7.01 (m, 1H, aromatic-H), 7.22 (m, 2H, aromatic-Hs), 7.32 (m, 4H, aromatic-Hs), 7.52 (m, 1H, Aromatic-H), 7.83 (m, 1H, aromatic-Hs) and 7.97 (s, 1H, 2'-H); $^{13}$C NMR (500 MHz, CDCl$_3$) δ 160.6, 159.5, 158.0, 156.0, 147.1, 129.2, 124.2, 123.5, 121.7, 120.2, 117.4, 114.7, 111.2, 55.3, 55.0, 47.3, 38.2, 36.0, 34.1, 32.4, 30.2, 24.6, 21.0, 20.0, 17.6, 16.1. HRMS calcd 500.2672 ($C_{32}H_{35}ON_3.Na^+$), found 500.2677.

3-((EZ)-O-Methyloxime)-17-(1H-Benzimidazol-1-yl)-androsta-4,16-diene (38)

Compound 38 prepared by following general method F. To a refluxing solution of 32 (0.075 g, 0.194 mmol) in ethanol-methanol (2 ml) added a solution of sodium acetate (0.15 g, 1.83 mmol), methoxyamine.HCl (0.17 g, 2.04 mmol) in 0.75 ml distilled water. The reflux continued for 3 h and subsequent purification by FCC gave compound (mixture of EZ isomers) 38 (0.072 g, 89%): mp 94-96° C.; IR (Neat) 2935, 2854, 1628, 1489, 1452, 1226, 1050, 743 cm$^{-1}$; $^1$H NMR (500 MHz, CDCl$_3$) δ 1.04 (s, 3H, 18-CH$_3$), 1.11 (s, 3H, 19-CH$_3$), 3.89 (s, 3H, OCH$_3$), 5.83 and 6.44 (~69% and 31% for E and Z isomers respectively) (s, 1H, 4-H), 6.03 (m, 1H, 16-H), 7.35 (m, 2H, aromatic-Hs), 7.53 (m, 1H, aromatic-H), 7.87 (m, 1H, aromatic-H), and 8.06 (s, 1H, 2'-H); $^{13}$C NMR (500 MHz, CDCl$_3$) δ 158.7, 156.0, 154.5, 153.1, 146.7, 125.2, 124.0, 123.3, 119.6, 117.7, 111.2, 61.6, 55.3, 54.2, 47.3, 38.0, 34.2, 32.2, 31.5, 30.3, 24.7, 21.0, 19.2, 17.6, 16.1. HRMS calcd 438.2515 ($C_{27}H_{33}ON_3.Na^+$), found 438.2520.

3-((EZ)-(O-Phenylmethyl)oxime)-17-(1H-Benzimidazol-1-yl)-androsta-4,16-diene (39)

Compound 39 prepared by following general method F. To a refluxing solution of 32 (0.075 g, 0.194 mmol) in ethanol-methanol (2 ml) added a solution of sodium acetate (0.15 g, 1.83 mmol), benzyloxyamine.HCl (0.33 g, 2.04 mmol) in 0.75 ml distilled water. The reflux continued for 3 h and subsequent purification by FCC gave compound (mixture of EZ isomers) 39 (0.092 g, 96%) which solidifies on storage: mp sinters 66-68° C., melts 77-79° C.; IR (Neat) 2935, 2854, 1627, 1609, 1489, 1452, 1225, 1015, 864 cm$^{-1}$; $^1$H NMR (500 MHz, CDCl$_3$) δ 1.03 (s, 3H, 18-CH$_3$), 1.10 (s, 3H, 19-CH$_3$), 5.10 (s, 2H, OCH$_2$), 5.83 and 6.52 (~69% and 31% for E and Z isomers respectively) (s, 1H, 4-H), 5.97 (s, 1H, 16-H), 7.25 (br, 3H, aromatic-Hs), 7.37 (m, 4H, aromatic-Hs), 7.48 (m, 1H, aromatic-H), 7.82 (m, 1H, aromatic-H) and 7.95 (s, 1H, 2'-H); $^{13}$C NMR (500 MHz, CDCl$_3$) δ 156.4, 154.6, 153.5, 147.0, 138.1, 127.9, 122.8, 120.0, 117.8, 111.3, 55.4, 54.0, 47.3, 38.0, 34.6, 32.2, 30.3, 24.7, 21.0, 19.6, 17.9, 16.1. HRMS calcd 514.2828 ($C_{33}H_{37}ON_3.Na^+$), found 514.2834.

3-Methyl-3-hydroxy-17-(1H-benzimidazol-1-yl)-androsta-4,16-diene (40)

To a solution of ketone (32) (0.1 g, 0.26 mmol) in dry THF (3 mL) was added MeLi (1.6 M solution in ether, 0.41 mL, 0.60 mmol) at −60° C., and the resulting mixture was stirred at 0° C. for 1 h then room temperature for 3 h. The reaction was quenched with saturated aqueous NH$_4$Cl and was extracted with EtOAc. The organic layer was washed with brine and dried over Na$_2$SO$_4$, and the solvent was removed under vacuum. The residue was purified by short FCC [petroleum ether, EtOAc, TEA (60:40:0.5)] to afford product 40 (0.05 g, 48%); mp 95-97° C.; IR (Neat) 3329, 2827, 2853, 1489, 1453, 1376, 1292, 1226, 1133, 918, 741 cm$^{-1}$; $^1$H NMR (500 MHz, CDCl$_3$) δ 1.00 (s, 3H, 18-CH$_3$), 1.07 (s, 3H, 19-CH$_3$), 1.27 (s, 3H, C3-CH$_3$), 5.25 (t, J=1.6 Hz, 1H, 6-H), 5.96 (t, 1H, J=1.52 Hz, 16-H), 7.29 (m, 2H, aromatic-Hs), 7.49 (m, 1H, aromatic-H), 7.82 (dd, J=7.0, 2.6 Hz, 1H, aromatic-H), and 7.95 (s, 1H, 2'-H); $^{13}$C NMR (500 MHz, CDCl$_3$) δ 145.3, 127.6, 124.4, 123.6, 122.7, 120.4, 111.4, 70.1, 55.7, 54.8, 37.8, 35.6, 35.3, 34.7, 32.5, 30.4, 28.5, 21.1, 18.8, 16.3. HRMS calcd 425.2563 ($C_{27}H_{34}ON_2.Na^+$), found 425.2570.

General Method G

Mixed anhydride method for the synthesis of aromatic/heteroaromatic esters (41-44): 2-Methyl-6-nitrobenzoic anhydride (0.39 mmol) was added to a solution of pyridinecaboxylic acid (0.386 mmol) and DMAP (0.29 mmol) in THF (1 ml), and the resulting mixture was allowed to stand at room temperature for 5 min. A solution of 5 (0.193 mmol) in THF (1 ml) was mixed with the above reagent mixture and then with TEA (0.1 ml). This reaction mixture was allowed to stand at room temperature for 2 h. Reaction mixture absorbed on silica and purified by FCC using 2% ethanol in DCM in presence of traces of TEA (0.06%). The picolinoyl, nicotinoyl, isonoctinoyl and 1,3-phenyldiacetic acid esters derivatives were synthesized in a manner similar to the above. TLC and $^1$H NMR and HRMS analyses revealed that the presence of other esters derived from 2-methyl-6-nitrobenzoic anhydride is absent.

3β-(Pyridine-2-carboxylate)-17-(1H-benzimidazol-1-yl)-androsta-5,16-diene (41)

Compound 41 prepared by following general method G, using 2-Methyl-6-nitrobenzoic anhydride (0.13 g, 0.39 mmol), picolinic acid (0.05 g, 0.39 mmol), 4-DMAP (0.04 g, 0.29 mmol), THF (1 ml), 5 (0.075 g, 0.19 mmol), THF (1 ml) and TEA (0.1 ml). FCC gave pure 41 (0.09 g, 90%): mp 243-44° C.; IR (Neat) 2942, 2852, 1729, 1496, 1286, 1227, 1139, 754 cm$^{-1}$; $^1$H NMR (400 MHz, CDCl$_3$) δ 1.03 (s, 3H, 18-CH$_3$), 1.12 (s, 3H, 19-CH$_3$), 4.99 (m, 1H, 3α-H), 5.49 (t, 1H, J=1.98 Hz, 6-H), 5.99 (t, 1H, J=1.42 Hz, 16-H), 7.32 (m, 2H, aromatic-Hs), 7.46-7.50 (m, 2H, picolinoyl-5-H and aromatic-H), 7.80-7.84 (m, 1H, aromatic-H), and (1H, picolinoyl-4-H), 7.96 (s, 1H, 2'-H), 8.15 (br, 1H, picolinoyl-3-H), 8.79 (m, 1H, picolinoyl-6-H); $^{13}$C NMR (500 MHz, CDCl$_3$) δ 164.9, 150.1, 148.7, 143.4, 141.8, 140.2, 137.2, 134.7, 127.0, 125.4, 124.4, 123.6, 122.7, 120.3, 111.4, 75.6, 56.0, 50.6, 47.4, 38.2, 37.2, 35.0, 31.3, 30.5, 27.8, 20.82, 19.5, 17.0. HRMS calcd 516.2621 ($C_{32}H_{35}O_2N_3.Na^+$), found 516.2614.

3β-(Pyridine-3-carboxylate)-17-(1H-benzimidazol-1-yl)-androsta-5,16-diene (42)

Compound 42 prepared by following general method G, using 2-Methyl-6-nitrobenzoic anhydride (0.13 g, 0.39 mmol), nicotinic acid (0.05 g, 0.39 mmol), 4-DMAP (0.035 g, 0.29 mmol), THF (1 ml), 5 (0.075 g, 0.19 mmol), THF (1 ml) and TEA (0.1 ml). FCC gave pure 42 (0.85 g, 89%): mp 206-207° C.; IR (Neat) 3435, 2942, 2851, 1710, 1496, 1285, 1120, cm$^{-1}$; $^1$H NMR (400 MHz, CDCl$_3$) δ 1.03 (s, 3H, 18-CH$_3$), 1.13 (s, 3H, 19-CH$_3$), 4.93 (m, 1H, 3α-H), 5.49 (br, 1H, 6-H), 5.99 (t, 1H, J=1.46 Hz, 16-H), 7.32 (m, 2H, aromatic-Hs), 7.41 (m, 1H, nicotinoyl-5-H), 7.50 (m, 1H, aromatic-H), 7.83 (m, 1H, aromatic-H), 7.98 (s, 1H, 2'-H), 8.33 (m, 1H, nicotinoyl-4-H), 8.79 (m, 1H, nicotinoyl-6-H), 9.23 (br. s, 1H, nicotinoyl-2-H); $^{13}$C NMR (500 MHz, CDCl$_3$) δ 164.9, 153.5, 151.1, 147.3, 141.8, 140.0, 137.3, 126.8, 124.4, 123.6, 122.7, 120.4, 111.4, 75.2, 55.0, 50.6, 47.4, 38.3, 37.1, 35.0, 31.3, 30.5, 20.8, 19.5, 16.2. HRMS calcd 516.2621 ($C_{32}H_{35}O_2N_3.Na^+$), found 516.2617.

3β-(Pyridine-4-carboxylate)-17-(1H-benzimidazol-1-yl)-androsta-5,16-diene (43)

Compound 43 prepared by following general method G, using 2-Methyl-6-nitrobenzoic anhydride (0.13 g, 0.39 mmol), isonicotinic acid (0.05 g, 0.39 mmol), 4-DMAP (0.035 g, 0.29 mmol), THF (1 ml), 5 (0.075 g, 0.19 mmol), THF (1 ml) and TEA (0.1 ml). FCC gave pure 43 (0.064 g, 67%): mp 184-85° C.; IR (Neat) 2944, 2953, 1719, 1489, 1282, 1124, 745 cm$^{-1}$; $^1$H NMR (400 MHz, CDCl$_3$) δ 1.03 (s, 3H, 18-CH$_3$), 1.13 (s, 3H, 19-CH$_3$), 4.90 (m, 1H, 3α-H), 5.49 (br, 1H, 6-H), 5.99 (s, 1H, 16-H), 7.30 (m, 2H, aromatic-Hs), 7.49 (m, 1H, aromatic-H), 7.81 (m, 1H, aromatic-H), 7.85 (m, 2H, isonicotinoyl-3, 5-Hs), 7.96 (s, 1H, 2'-H), and 8.78 (m, 2H, isonicotinoyl-2, 6-Hs); $^{13}$C NMR (500 MHz, CDCl$_3$) δ 164.7, 150.8, 147.4, 143.5, 141.8, 139.9, 138.1, 134.8, 124.3, 123.6, 122.7, 120.4, 111.3, 75.6, 56.0, 50.6, 47.4, 38.2, 37.0, 35.0, 31.3, 30.5, 27.9, 19.5, 16.2. HRMS calcd 516.2621 ($C_{32}H_{35}O_2N_3.Na^+$), found 516.2615.

3β-(3-(Oxycarbonyl)phenylacetic acid)-17-(1H-benzimidazol-1-yl)-androsta-5,16-diene (44)

Compound 41 prepared by following general method G, using 2-Methyl-6-nitrobenzoic anhydride (0.18 g, 0.51 mmol) was added to a solution of 1,3-phenyldiacetic acid (0.1 g, 0.51 mmol) and DMAP (0.05 g, 0.39 mmol) in THF (2 ml), 5 (0.1 g, 0.26 mmol), THF (1 ml) and TEA (0.15 ml). FCC gave pure 44 (0.055 g, 39.81%): mp 222-23° C.; IR (Neat) 2944, 1734, 1610, 1454, 1337, 1204, 1165, 1003 749 cm$^{-1}$; $^1$H NMR (500 MHz, CDCl$_3$) δ 0.99 (s, 3H, 18-CH$_3$), 1.05 (s, 3H, 19-CH$_3$), 3.59 (s, 2H, CH$_2$—Hs), 3.64 (s, 2H, CH$_2$—Hs), 4.63 (m, 1H, 3α-H), 5.40 (br, 1H, 6-H), 5.98 (m, 1H, 16-H), 7.18-7.23 (m, 3H, aromatic-Hs), 7.27-7.31 (m, 3H, aromatic-H), 7.47 (m, 1H, aromatic-H), 7.81 (m, 1H, aromatic-H) 8.01 (s, 1H, 2'-H); $^{13}$C NMR (400 MHz, CDCl$_3$) δ 171.2, 147.1, 141.8, 140.3, 135.0, 134.6, 130.5, 128.9, 128.0, 125.0, 123.9, 122.16, 120.0, 111.5, 74.4, 56.0, 50.5, 47.4, 45.6, 41.8, 38.2, 37.0, 37.0, 31.3, 30.5, 27.82, 20.8, 19.4, 16.1, 8.7. HRMS calcd 587.2880 ($C_{36}H_{40}O_4N_2.Na^+$), found 587.2876

3β-(6-(Cyclohex-3-enecaboxylic acid)carboxylate)-17-(1H-benzimidazol-1-yl)-androsta-5,16-diene (45)

A mixture of 5 (0.1 g, 0.26 mmol), DMAP (0.035 g, 0.28 mmol), 1,2,3,6-tetrahydrophthalic anhydride (0.13 g, 0.85 mmol) and pyridine (3 mL) was refluxed for 3 hrs. Cooled to room temperature and quenched to water. Precipitate was extracted with EtOAc, dried with Na$_2$SO$_4$, evaporated and the residue was purified by FCC [petroleum ether/EtOAc/TEA (9.5:0.3:0.2)] to give 0.1 g (71.9%) of pure compound 45: mp 178-179° C.; IR (Neat) 2931, 1724, 1453, 1225, 1195 and 743 cm$^{-1}$; $^1$H NMR (400 MHz, CDCl$_3$) δ 0.99-1.04 (m, 6H, 18-CH$_3$ and 19-CH$_3$), 4.64 (m, 1H, 3α-H), 5.40 (br, 1H, 6-H), 5.69 (m, 2H, c-hexyl-4, c-hexyl-5, Hs), 5.96 (s, 1H, 16-H), 7.30 (m, 2H, aromatic-Hs), 7.50 (d, 1H, aromatic-H), 7.84 (1H, m, aromatic-H) 8.05 (s, 1H, 2'-H); $^{13}$C NMR (500 MHz, CDCl$_3$) δ 177.3, 173.5, 1401.0, 126.0, 125.3, 124.8, 123.8, 123.0, 121.9, 120.0, 111.4, 73.8, 55.9, 50.5, 47.4, 45.4, 40.7, 38.2, 37.1, 34.9, 31.3, 30.5, 27.7, 26.4, 19.4, 16.2, 8.8. HRMS calcd 563.2880 ($C_{34}H_{40}N_2O_4.Na^+$), found 563.2879.

3β-(Oxycarbonyl-(methoxy) acetic acid)-17-(1H-benzimidazol-1-yl)-androsta-5,16-diene (46):

A mixture of 5 (0.1 g, 0.26 mmol), DMAP (0.035 g, 0.28 mmol), diglycolic anhydride (0.1 g, 0.85 mmol) and pyridine (3 mL) was refluxed for 3 hrs. Cooled to room temperature and quenched to water. Precipitate was extracted with EtOAc, dried with Na$_2$SO$_4$, evaporated and the residue was purified by FCC [petroleum ether/EtOAc/TEA (9.5:0.3:0.2)] to give 0.05 g (28.6%) of pure compound 46: mp 214-215° C.; IR (Neat) 2934, 1722, 1456, 1225, 1147 and 745 cm$^{-1}$; $^1$H NMR (500 MHz, CDCl$_3$) δ 1.01 (s, 3H, 18-CH$_3$), 1.07 (s, 3H, 19-CH$_3$), 4.25 (s, 2H, CH$_2$), 4.26 (s, 2H, CH$_2$), 4.74 (m, 1H, 3α-H), 5.45 (br, 1H, 6-H), 6.00 (m, 1H, 16-H), 7.32 (m, 2H, aromatic-Hs), 7.49 (m, 1H, aromatic-H), 7.82 (m, 1H, aromatic-H), 8.06 (s, 1H, 2' aromatic-H); $^{13}$C NMR (500 MHz, CDCl$_3$); δ 172.9, 169.9, 147.0, 141.7, 140.0, 134.4, 125.4, 124.2, 123.4, 119.7, 111.6, 75.0, 69.1, 68.8, 56.0, 50.5, 47.4, 38.2, 37.0, 34.9, 31.3, 31.1, 30.5, 27.8, 20.8, 19.4, 16.2. HRMS calcd 527.2516 ($C_{30}H_{36}N_2O_5.Na^+$), found 527.2516.

3β-(1H-Imidazole-1-carboxylate)-17-(1H-benzimidazol-1-yl)-androsta-5,16-diene (47)

A solution of 5 (0.15 g, 0.38 mmol), CDI (0.125 g, 0.77 mmol) in anhydrous acetonitrile (2 mL) and DCM (1 mL) stirred at room temperature for 2 h. Then solvent evaporated, residue treated with water, and extracted with DCM. The crude white product obtained on evaporation of solvent was purified by FCC using 1.7% methanol in DCM in presence of traces of TEA (0.06%) to give 47 (0.135 g, 72%): mp 194-96° C.; IR (Neat) 2965, 2923, 2839, 1754, 1488, 1452, 1392, 1292, 834, 773 cm$^{-1}$; $^1$H NMR (500 MHz, CDCl$_3$) δ 1.03 (s, 3H, 18-CH$_3$), 1.12 (s, 3H, 19-CH$_3$), 4.85 (m, 1H, 3α-H), 5.51 (br, 1H, 6-H), 5.99 (s, 1H, 16-H), 7.07 (s, 1H, 4"-H), 7.30 (m, 2H, aromatic-Hs), 7.43 (s, 1H, aromatic-H), 7.49 (m, 1H, 5"-H) 7.81 (m, 1H, aromatic-H), 7.96 (s, 1H, 2'-H) and 8.13 (s, 1H, 2"-H); $^{13}$C NMR (500 MHz, CDCl$_3$) δ 148.1, 147.1, 143.3, 141.3, 139.1, 137.1, 134.6, 130.6, 124.1, 123.1, 120.2, 117.1, 111.1, 78.4, 55.7, 50.6, 47.2, 37.9, 36.8, 34.8, 31.1, 30.3, 27.6, 20.6, 19.3, 16.0. HRMS calcd 505.2573 ($C_{30}H_{34}O_2N_4.Na^+$), found 505.2577.

3β-(2-Methyl-1H-imidazole-1-carboxylate)-17-(1H-benzimidazol-1-yl)-androsta-5,16-diene (48)

A solution of 5 (0.075 g, 0.193 mmol), 1,1-carbonylbis (2-methylimidazole) (0.05 g, 0.214 mmol) in anhydrous acetonitrile (1.5 mL) and DCM (0.75 mL) was refluxed over-night. The solvent evaporated, residue treated with water, and extracted with DCM. The crude white product obtained on evaporation of solvent was purified by FCC using 4% ethanol in DCM in presence of traces of TEA (0.06%). The product was triturated with petroleum ether to give 48 (0.065 g, 67%): mp 186-187° C.; IR (Neat) 2935, 2855, 1749, 1452, 1394, 1291, 1146, 983 cm$^{-1}$; $^1$H NMR (500 MHz, CDCl$_3$) δ 1.03 (s, 3H, 18-CH$_3$), 1.12 (s, 3H, 19-CH$_3$), 2.64 (s, 3H, 2"-CH$_3$), 4.80 (m, 1H, 3α-H), 5.51 (m, 1H, 6-H), 5.99 (m, 1H, 16-H), 6.84 (s, 1H, 5"-H), 7.29 (m, 2H, aromatic-Hs), 7.35 (s, 1H, aromatic-H), 7.48 (m, H, aromatic-H) 7.81 (m, 1H, 4"-H), and 7.96 (s, 1H, 2'-H); $^{13}$C NMR (500 MHz, CDCl$_3$) δ 149.0, 147.9, 147.1, 143.3, 141.6, 139.2, 134.6, 127.8, 123.4, 122.5, 120.2, 118.1, 111.1, 78.0, 55.7, 50.3, 47.2, 38.0, 36.8, 34.8, 31.1, 30.3, 27.7, 20.6, 19.3, 16.9, 16.0. HRMS calcd 519.2730 ($C_{31}H_{36}O_2N4.Na^+$), found 519.2730.

3β-(1H-1,2,4-Triazole-1-carboxylate)-17-(1H-benzimidazol-1-yl)-androsta-5,16-diene (49)

A solution of 5 (0.15 g, 0.386 mmol), CDT (0.19 g, 1.16 mmol) in anhydrous acetonitrile (3 mL) and DCM (1.5 mL) was refluxed for 3 h. The solvent evaporated, residue treated with water, and extracted with DCM. The crude white product obtained on evaporation of solvent was purified by FCC using 4% Ethanol in DCM in presence of traces of TEA (0.06%). The product was triturated with petroleum ether to give 49 (0.15 g, 80%): mp 205-206° C.; IR (Neat) 2950, 2855, 1776, 1489, 1375, 1289, 978, 750 cm$^{-1}$; $^1$H NMR (500 MHz, CDCl$_3$) δ 1.03 (s, 3H, 18-CH$_3$), 1.12 (s, 3H, 19-CH$_3$), 4.96 (m, 1H, 3α-H), 5.52 (m, 1H, 6-H), 5.99 (s, 1H, 16-H), 7.30 (m, 2H, aromatic-Hs), 7.50 (t, 1H, J=3.8 Hz, aromatic-H), 7.81 (m, H, aromatic-H), 7.96 (s, 1H, 2'-H), 8.07 (s, 1H, 5"-H), and 8.83 (s, 1H, 3"-H); $^{13}$C NMR (500 MHz, CDCl$_3$) δ 153.8, 147.3, 145.8, 143.5, 141.8, 139.2, 134.7, 124.3, 123.6, 122.7, 120.4, 111.3, 80.0, 55.9, 50.5, 47.4, 37.9, 37.0, 35.0, 31.3, 30.5, 27.6, 20.8, 19.4, 16.2. HRMS calcd 506.2526 (C$_{29}$H$_{33}$O$_2$N$_5$.Na$^+$), found 506.2525.

What is claimed is:

1. A method of inhibiting androgen receptor (AR) activity in a cell, the method comprising a step of:
   down-regulating androgen receptor (AR) level in a cell, wherein the step of down-regulating comprises administering a composition that delivers to the cell a steroidal compound and wherein the compound is characterized by an ability to inhibit growth of CWR22Rv1 cells with a GI50 below about 15 μM.

2. The method of claim 1, wherein the compound is not an androgen synthesis inhibitor more potent than a reference compound selected from abiraterone acetate, TAK-700, or galeterone.

3. The method of claim 1, wherein the compound is not an AR antagonist more potent than a reference compound selected from abiraterone acetate, TAK-700, or galeterone.

4. The method of claim 1, wherein the compound is characterized in that exposure of a cell comprising AR to the compound results in down-regulation of AR, inhibition of AR mediated transcription and inhibition of cell growth.

5. The method of claim 4, wherein the down-regulation of AR and inhibition of AR mediated transcription occur before the cell growth inhibition.

6. The method of claim 1, wherein the compound is characterized by an ability to inhibit CYP17 with an IC50 below 1 μM.

7. The method of claim 1, wherein the cell has both full-length and splice variant androgen receptor.

8. The method of claim 7, wherein the splice variant androgen receptor is lacking the ligand binding domain.

9. The method of claim 7, wherein the splice variant androgen receptor is AR-V7.

10. The method of claim 1, wherein the cell is not responsive to AR anti-androgens or androgen deprivation therapy.

11. A method of claim 1, wherein the cell is resistant to abiraterone acetate.

12. A method of claim 1, wherein the cell is resistant to enzalutamide.

13. The method of claim 1, wherein the cell is an androgen-related disease cell.

* * * * *

UNITED STATES PATENT AND TRADEMARK OFFICE
CERTIFICATE OF CORRECTION

Page 1 of 1

PATENT NO. : 9,884,067 B2
APPLICATION NO. : 14/759555
DATED : February 6, 2018
INVENTOR(S) : Vincent C. O. Njar et al.

It is certified that error appears in the above-identified patent and that said Letters Patent is hereby corrected as shown below:

On the Title Page

<u>Item (72)</u>:
Change the third inventor's name from:
"Puranik Purushottamachar, Gaithersburg, MD (US)"
To be:
-- Purushottamachar Puranik, Gaithersburg, MD (US) --

Signed and Sealed this
Thirty-first Day of August, 2021

Drew Hirshfeld
*Performing the Functions and Duties of the*
*Under Secretary of Commerce for Intellectual Property and*
*Director of the United States Patent and Trademark Office*